US011013771B2

(12) United States Patent
Yoshida

(10) Patent No.: US 11,013,771 B2
(45) Date of Patent: May 25, 2021

(54) METHODS FOR THE STORAGE OF WHOLE BLOOD, AND COMPOSITIONS THEREOF

(71) Applicant: Hemanext Inc., Lexington, MA (US)

(72) Inventor: Tatsuro Yoshida, West Newton, MA (US)

(73) Assignee: Hemanext Inc., Lexington, MA (US)

( * ) Notice: Subject to any disclaimer, the term of this patent is extended or adjusted under 35 U.S.C. 154(b) by 0 days.

(21) Appl. No.: 15/575,249

(22) PCT Filed: May 18, 2016

(86) PCT No.: PCT/US2016/033151
§ 371 (c)(1),
(2) Date: Nov. 17, 2017

(87) PCT Pub. No.: WO2016/187353
PCT Pub. Date: Nov. 24, 2016

(65) Prior Publication Data
US 2018/0133255 A1  May 17, 2018

Related U.S. Application Data

(60) Provisional application No. 62/163,269, filed on May 18, 2015.

(51) Int. Cl.
A61K 35/18 (2015.01)
A61K 35/14 (2015.01)
A61P 7/00 (2006.01)
A61P 43/00 (2006.01)
A61M 1/02 (2006.01)

(52) U.S. Cl.
CPC .............. *A61K 35/18* (2013.01); *A61K 35/14* (2013.01); *A61P 7/00* (2018.01); *A61P 43/00* (2018.01); *A61M 1/0272* (2013.01)

(58) Field of Classification Search
None
See application file for complete search history.

(56) References Cited

U.S. PATENT DOCUMENTS

| 3,064,647 | A | 11/1962 | Earl |
| 3,361,041 | A | 1/1968 | Grob |
| 3,668,837 | A | 6/1972 | Gross |
| 3,668,838 | A | 6/1972 | McNeil et al. |
| 3,803,810 | A | 4/1974 | Rosenberg |
| 3,910,841 | A | 10/1975 | Esmond |
| 3,942,529 | A | 3/1976 | Waage |
| 4,075,091 | A | 2/1978 | Bellhouse |
| 4,086,924 | A | 5/1978 | Latham, Jr. |
| 4,093,515 | A | 6/1978 | Kolobow |
| 4,131,200 | A | 12/1978 | Rinfret |
| 4,162,676 | A | 7/1979 | Talcott |
| 4,222,379 | A | 9/1980 | Smith |
| 4,225,439 | A | 9/1980 | Spranger |
| 4,228,032 | A | 10/1980 | Talcott |
| 4,253,458 | A | 3/1981 | Bacehowski et al. |
| 4,256,692 | A | 3/1981 | Cover |
| 4,262,581 | A | 4/1981 | Ferrell |
| 4,300,559 | A | 11/1981 | Gajewski et al. |
| 4,314,480 | A | 2/1982 | Becker |
| 4,342,723 | A | 8/1982 | Sado et al. |
| 4,366,179 | A | 12/1982 | Nawata et al. |
| 4,370,160 | A | 1/1983 | Ziemelis |
| 4,381,775 | A | 5/1983 | Nose' et al. |
| 4,386,069 | A | 5/1983 | Estep |
| 4,398,642 | A | 8/1983 | Okudaira et al. |
| 4,440,815 | A | 4/1984 | Zomorodi et al. |
| 4,455,299 | A | 6/1984 | Grode |
| 4,540,416 | A | 9/1985 | Hattori et al. |
| 4,568,328 | A | 2/1986 | King et al. |
| 4,572,899 | A | 2/1986 | Walker et al. |
| 4,579,223 | A | 4/1986 | Otsuka et al. |
| 4,585,735 | A | 4/1986 | Meryman et al. |
| 4,609,383 | A | 9/1986 | Bonaventura et al. |
| 4,629,544 | A | 12/1986 | Bonaventura et al. |
| 4,639,353 | A | 1/1987 | Takemura et al. |
| 4,654,053 | A | 3/1987 | Sievers et al. |
| 4,659,549 | A | 4/1987 | Hamada et al. |
| 4,670,013 | A | 6/1987 | Barnes et al. |
| 4,701,267 | A | 10/1987 | Watanabe et al. |
| 4,713,176 | A | 12/1987 | Schoendorfer et al. |
| 4,731,978 | A | 5/1988 | Martensson |
| 4,748,121 | A | 5/1988 | Beaver et al. |
| 4,749,551 | A | 6/1988 | Borgione |

(Continued)

FOREIGN PATENT DOCUMENTS

| AU | 2012279043 | 7/2016 |
| CA | 2477946 | 9/2003 |

(Continued)

OTHER PUBLICATIONS

Gardner et al. (Problems of Multiple Transfusions. Official Journal of the California Medical Association. 1958. pp. 93-97).*
Steurer etal. (Trauma and Massive Blood Transfusions. Curr Anesthesiol Red. Published online May 1, 2014; 4:200-208).*
Strandenes et al. (Emergency Whole-Blood Use InThe Field: A Simplified Protocol For Collection And Transfusion. SHOCK, vol. 41, Supplement 1, pp. 76-83, 2014).*
Yoshida et al. (Anaerobic storage of red blood cells. Blood Transfus 2010:8:220-36).*
Strandenes et al. Emergency Whole-Blood Use In The Field: A Simplified Protocol For Collection And Transfusion. SHOCK, vol. 41, Supplement 1, pp. 76-83, 2014 (Year: 2014).*
U.S. Appl. No. 10/295,781, filed Nov. 15, 2002, Bitensky et al.
U.S. Appl. No. 62/131,130, filed Mar. 15, 2015, Wolf et al.
U.S. Appl. No. 62/151,957, filed Apr. 23, 2015, Yoshida et al.
U.S. Appl. No. 12/901,350, filed Oct. 8, 2010, Yoshida et al.

(Continued)

*Primary Examiner* — Susan M Hanley
(74) *Attorney, Agent, or Firm* — Arnold & Porter Kaye Scholer LLP

(57) ABSTRACT

Methods and compositions for improved clinical outcomes for trauma patients receiving whole blood transfusion. Methods and compositions for improved clinical outcomes for blood transfusions for cancer patients are also provided.

11 Claims, 19 Drawing Sheets

(56) References Cited

U.S. PATENT DOCUMENTS

| | | |
|---|---|---|
| 4,769,175 A | 9/1988 | Inoue |
| 4,769,318 A | 9/1988 | Hamasaki et al. |
| 4,798,728 A | 1/1989 | Sugisawa |
| 4,828,561 A | 5/1989 | Woodroof |
| 4,837,047 A | 6/1989 | Sato et al. |
| 4,859,360 A | 8/1989 | Suzuki et al. |
| 4,861,867 A | 8/1989 | Estep |
| 4,880,548 A | 11/1989 | Pall et al. |
| 4,880,786 A | 11/1989 | Sasakawa et al. |
| 4,902,701 A | 2/1990 | Batchelor et al. |
| 4,925,572 A | 5/1990 | Pall |
| 4,986,837 A | 1/1991 | Shibata |
| 4,998,990 A | 3/1991 | Richter et al. |
| 5,000,848 A | 3/1991 | Hodgins et al. |
| 5,023,054 A | 6/1991 | Sato et al. |
| 5,037,419 A | 8/1991 | Valentine et al. |
| 5,120,659 A | 6/1992 | King et al. |
| 5,137,531 A | 8/1992 | Lee et al. |
| 5,139,668 A | 8/1992 | Pan et al. |
| 5,143,763 A | 9/1992 | Yamada et al. |
| 5,152,905 A | 10/1992 | Pall et al. |
| 5,192,320 A | 3/1993 | Anazawa et al. |
| 5,194,158 A | 3/1993 | Matson |
| 5,208,335 A | 5/1993 | Ramprasad et al. |
| 5,229,012 A | 7/1993 | Pall et al. |
| 5,254,248 A | 10/1993 | Nakamura et al. |
| 5,286,407 A | 2/1994 | Inoue et al. |
| 5,328,268 A | 7/1994 | LaFleur |
| 5,353,793 A | 10/1994 | Bornn |
| 5,356,375 A | 10/1994 | Higley |
| 5,360,734 A | 11/1994 | Chapman et al. |
| 5,362,442 A | 11/1994 | Kent |
| 5,368,808 A | 11/1994 | Koike et al. |
| 5,382,526 A | 1/1995 | Gajewski et al. |
| 5,386,014 A | 1/1995 | Nho et al. |
| 5,387,624 A | 2/1995 | Morita et al. |
| 5,417,986 A | 5/1995 | Reid et al. |
| 5,427,663 A | 6/1995 | Austin et al. |
| 5,443,743 A | 8/1995 | Gsell |
| 5,449,617 A | 9/1995 | Falkenberg et al. |
| 5,476,764 A | 12/1995 | Bitensky |
| 5,506,141 A | 4/1996 | Weinreb et al. |
| 5,529,821 A | 6/1996 | Ishikawa et al. |
| 5,605,934 A | 2/1997 | Giertych |
| 5,617,873 A | 4/1997 | Yost et al. |
| 5,624,794 A | 4/1997 | Bitensky et al. |
| 5,635,358 A | 6/1997 | Wilding et al. |
| 5,686,304 A | 11/1997 | Codner |
| 5,691,452 A | 11/1997 | Gawryl et al. |
| 5,693,122 A | 12/1997 | Berndt |
| 5,693,230 A | 12/1997 | Asher |
| 5,698,250 A | 12/1997 | DelDuca et al. |
| 5,709,472 A | 1/1998 | Prusik et al. |
| 5,744,056 A | 4/1998 | Venkatcshwaran et al. |
| 5,730,989 A | 5/1998 | Wright |
| 5,750,115 A | 5/1998 | Van Den Bosch |
| 5,783,094 A | 7/1998 | Kraus et al. |
| 5,783,148 A | 7/1998 | Cottingham et al. |
| 5,789,151 A | 8/1998 | Bitensky et al. |
| 5,789,152 A | 8/1998 | Black et al. |
| 5,811,142 A | 9/1998 | DelDuca et al. |
| 5,846,427 A | 12/1998 | Kessler et al. |
| 5,858,015 A | 1/1999 | Fini |
| 5,858,643 A | 1/1999 | Ben-Hur et al. |
| 5,863,460 A | 1/1999 | Slovacek et al. |
| 5,895,810 A | 4/1999 | Light et al. |
| 5,902,747 A | 5/1999 | Nemser et al. |
| 5,906,285 A | 5/1999 | Slat |
| 5,928,178 A | 7/1999 | Samolyk |
| 5,955,519 A | 9/1999 | Neri |
| 5,962,650 A | 10/1999 | Osterberg et al. |
| 5,972,710 A | 10/1999 | Weigl et al. |
| 6,007,529 A | 12/1999 | Gustafsson et al. |
| 6,027,623 A | 2/2000 | Ohkawa |
| 6,042,264 A | 3/2000 | Prusik et al. |
| 6,045,701 A | 4/2000 | Ung-Chhun et al. |
| 6,047,203 A | 4/2000 | Sackner et al. |
| 6,068,152 A | 5/2000 | Meiners et al. |
| 6,076,664 A | 6/2000 | Yeager |
| 6,080,322 A | 6/2000 | Deniega |
| 6,090,062 A | 7/2000 | Sood et al. |
| 6,097,293 A | 8/2000 | Galloway et al. |
| 6,148,536 A | 11/2000 | Iijima |
| 6,150,085 A | 11/2000 | Hess et al. |
| 6,156,231 A | 12/2000 | McKedy |
| 6,162,396 A | 12/2000 | Bitensky et al. |
| 6,164,821 A | 12/2000 | Randall |
| 6,187,572 B1 | 2/2001 | Platz et al. |
| 6,210,601 B1 | 4/2001 | Hottle et al. |
| 6,231,770 B1 | 5/2001 | Bormann et al. |
| 6,248,690 B1 | 6/2001 | McKedy |
| 6,254,628 B1 | 7/2001 | Wallace et al. |
| 6,287,284 B1 | 9/2001 | Woarburton-Pitt |
| 6,315,815 B1 | 11/2001 | Spadaccini |
| 6,337,026 B1 | 1/2002 | Lee et al. |
| 6,358,678 B1 | 3/2002 | Bakaltcheva et al. |
| 6,368,871 B1 | 4/2002 | Christel et al. |
| 6,387,461 B1 | 5/2002 | Ebner et al. |
| 6,402,818 B1 | 6/2002 | Sengupta et al. |
| 6,403,124 B1 | 6/2002 | Dottori |
| 6,413,713 B1 | 7/2002 | Serebrennikov |
| 6,436,872 B2 | 8/2002 | McKedy |
| 6,439,577 B2 | 8/2002 | Jorgensen et al. |
| 6,447,987 B1 | 9/2002 | Hess et al. |
| 6,468,732 B1 | 10/2002 | Malin et al. |
| 6,475,147 B1 | 11/2002 | Yost et al. |
| 6,479,252 B1 | 11/2002 | Barbera-Guillem et al. |
| 6,482,585 B2 | 11/2002 | Dottori |
| 6,494,909 B2 | 12/2002 | Greenhalgh |
| 6,527,957 B1 | 3/2003 | Denienga et al. |
| 6,558,571 B1 | 5/2003 | Powers |
| 6,564,207 B1 | 5/2003 | Abdoh |
| 6,582,496 B1 | 6/2003 | Cheng et al. |
| 6,610,772 B1 | 8/2003 | Clauberg et al. |
| 6,626,884 B1 | 9/2003 | Dillon et al. |
| 6,688,476 B2 | 2/2004 | Breillatt, Jr. et al. |
| 6,695,803 B1 | 2/2004 | Robinson et al. |
| 6,697,667 B1 | 2/2004 | Lee et al. |
| 6,709,492 B1 | 3/2004 | Spadaccini |
| 6,723,051 B2 | 4/2004 | Davidson et al. |
| 6,761,695 B2 | 7/2004 | Yost et al. |
| 6,773,407 B2 | 8/2004 | Yost et al. |
| 6,808,675 B1 | 10/2004 | Coelho et al. |
| 6,817,979 B2 | 11/2004 | Nihtilä |
| 6,866,783 B2 | 3/2005 | Baurmeister et al. |
| 6,878,335 B2 | 4/2005 | Britten et al. |
| 6,899,822 B2 | 5/2005 | McKedy |
| 6,955,648 B2 | 10/2005 | Mozayeni et al. |
| 6,977,105 B1 | 12/2005 | Fujieda et al. |
| 7,041,800 B1 | 5/2006 | Gawryl et al. |
| 7,097,690 B2 | 8/2006 | Usher et al. |
| 7,104,958 B2 | 9/2006 | Crutchfield et al. |
| 7,125,498 B2 | 10/2006 | McKedy |
| 7,208,120 B2 | 4/2007 | Bitensky et al. |
| 7,347,887 B2 | 3/2008 | Bulow et al. |
| 7,361,277 B2 | 4/2008 | Bormann et al. |
| 7,431,995 B2 | 10/2008 | Smith et al. |
| 7,452,601 B2 | 11/2008 | Ebner et al. |
| 7,517,146 B2 | 4/2009 | Smith et al. |
| 7,666,486 B2 | 2/2010 | Sato et al. |
| 7,713,614 B2 | 5/2010 | Chow et al. |
| 7,721,898 B2 | 5/2010 | Yagi et al. |
| 7,723,017 B2 | 5/2010 | Bitensky et al. |
| 7,754,798 B2 | 7/2010 | Ebner et al. |
| 7,763,097 B2 | 7/2010 | Federspiel |
| 7,775,376 B2 | 8/2010 | Bonaguidi et al. |
| 7,784,619 B2 | 8/2010 | Jacobson |
| 8,070,664 B2 | 12/2011 | Rochat |
| 8,071,282 B2 | 12/2011 | Bitensky et al. |
| 8,535,421 B2 | 9/2013 | Yoshida et al. |
| 8,569,052 B2 | 10/2013 | Federspiel et al. |
| 8,864,735 B2 | 10/2014 | Sano et al. |
| 8,877,508 B2 | 11/2014 | Hyde et al. |
| 8,887,721 B2 | 11/2014 | Zapol et al. |

(56) References Cited

U.S. PATENT DOCUMENTS

| | | |
|---|---|---|
| 9,005,343 B2 | 4/2015 | Yoshida et al. |
| 9,067,004 B2 | 6/2015 | Yoshida et al. |
| 9,199,016 B2 | 12/2015 | Yoshida et al. |
| 9,296,990 B2 | 3/2016 | Federspiel et al. |
| 9,539,375 B2 | 1/2017 | Yoshida et al. |
| 9,801,784 B2 | 10/2017 | Yoshida et al. |
| 9,844,615 B2 | 12/2017 | Yoshida et al. |
| 2001/0027156 A1 | 10/2001 | Egozy et al. |
| 2001/0037078 A1 | 11/2001 | Lynn et al. |
| 2001/0049089 A1 | 12/2001 | Dottori |
| 2002/0062078 A1 | 5/2002 | Crutchfield et al. |
| 2002/0066699 A1 | 6/2002 | Boggs et al. |
| 2002/0085952 A1 | 7/2002 | Ellingboe et al. |
| 2002/0086329 A1 | 7/2002 | Shvets et al. |
| 2002/0099570 A1 | 7/2002 | Knight |
| 2002/0176798 A1 | 11/2002 | Linker et al. |
| 2002/0182241 A1 | 12/2002 | Borenstein et al. |
| 2003/0003575 A1 | 1/2003 | Vacanti et al. |
| 2003/0039582 A1 | 2/2003 | Chambers et al. |
| 2003/0040835 A1 | 2/2003 | Ng et al. |
| 2003/0062299 A1 | 4/2003 | Lee et al. |
| 2003/0106861 A1 | 6/2003 | Gibbs et al. |
| 2003/0124504 A1 | 7/2003 | Bitensky et al. |
| 2003/0153074 A1 | 8/2003 | Bitensky et al. |
| 2003/0183801 A1 | 10/2003 | Yang et al. |
| 2003/0189003 A1 | 10/2003 | Kraus et al. |
| 2003/0190272 A1 | 10/2003 | Raine et al. |
| 2003/0201160 A1 | 10/2003 | Goodrich et al. |
| 2003/0215784 A1 | 11/2003 | Dumont et al. |
| 2003/0233934 A1 | 12/2003 | Wijmans et al. |
| 2004/0013566 A1 | 1/2004 | Myrick et al. |
| 2004/0026341 A1 | 2/2004 | Hogberg et al. |
| 2004/0097862 A1 | 5/2004 | Lampeter et al. |
| 2004/0126880 A1 | 7/2004 | Manders et al. |
| 2004/0146671 A1 | 7/2004 | Szabo et al. |
| 2004/0168982 A1 | 9/2004 | Bitensky et al. |
| 2004/0254560 A1 | 12/2004 | Coelho et al. |
| 2005/0038342 A1 | 2/2005 | Mozayeni et al. |
| 2005/0085785 A1 | 4/2005 | Shang et al. |
| 2005/0137517 A1 | 6/2005 | Blickhan et al. |
| 2005/0139806 A1 | 6/2005 | Havens et al. |
| 2005/0208462 A1 | 9/2005 | Bitensky et al. |
| 2005/0210141 A1 | 9/2005 | Oyama et al. |
| 2005/0230856 A1 | 10/2005 | Parekh et al. |
| 2005/0233302 A1 | 10/2005 | Hess et al. |
| 2006/0081524 A1 | 4/2006 | Sengupta et al. |
| 2006/0118479 A1 | 6/2006 | Shevkoplyas et al. |
| 2006/0160724 A1 | 7/2006 | Gawryl et al. |
| 2006/0169138 A1 | 8/2006 | Schmidt |
| 2006/0226087 A1 | 10/2006 | Robinson et al. |
| 2006/0278073 A1 | 12/2006 | McHugh |
| 2007/0078113 A1 | 4/2007 | Roth et al. |
| 2007/0099170 A1 | 5/2007 | Goodrich et al. |
| 2007/0207186 A1 | 9/2007 | Scanlon et al. |
| 2007/0240569 A1 | 10/2007 | Ooya |
| 2007/0276508 A1 | 11/2007 | Fischer et al. |
| 2008/0027368 A1 | 1/2008 | Kollar et al. |
| 2008/0098894 A1 | 5/2008 | Sabatino |
| 2008/0160107 A1 | 7/2008 | McCaney et al. |
| 2008/0234327 A1 | 9/2008 | Cadieux et al. |
| 2008/0243045 A1 | 10/2008 | Pasqualini |
| 2008/0276803 A1 | 11/2008 | Molaison et al. |
| 2008/0299538 A1 | 12/2008 | Goodrich et al. |
| 2009/0017128 A1 | 1/2009 | Monzyk et al. |
| 2009/0084720 A1 | 4/2009 | Dannenmaier et al. |
| 2009/0235619 A1 | 9/2009 | Ostler et al. |
| 2009/0269837 A1 | 10/2009 | Shevkoplyas et al. |
| 2010/0021879 A1 | 1/2010 | Delgado et al. |
| 2010/0133203 A1 | 6/2010 | Walker et al. |
| 2010/0221697 A1 | 9/2010 | Sehgal |
| 2010/0282662 A1 | 11/2010 | Lee et al. |
| 2010/0294128 A1 | 11/2010 | Schmidt |
| 2010/0313755 A1 | 12/2010 | Koros et al. |
| 2010/0331767 A1 | 12/2010 | Frankowski |
| 2011/0092875 A1 | 4/2011 | Beck |
| 2012/0024156 A1 | 2/2012 | Yoshida et al. |
| 2012/0077182 A1 | 3/2012 | Bitensky et al. |
| 2012/0100523 A1 | 4/2012 | Federspiel et al. |
| 2012/0115124 A1 | 5/2012 | Yoshida et al. |
| 2012/0129148 A1 | 5/2012 | Hess et al. |
| 2012/0129149 A1 | 5/2012 | Federspiel et al. |
| 2012/0146266 A1 | 6/2012 | Oda et al. |
| 2012/0219633 A1 | 8/2012 | Sowemimo-Coker |
| 2013/0004937 A1 | 1/2013 | Yoshida et al. |
| 2013/0144266 A1 | 6/2013 | Borenstein et al. |
| 2013/0197420 A1 | 8/2013 | Fissell, IV et al. |
| 2013/0259744 A1* | 10/2013 | Yoshida ............. A61M 1/0272 422/44 |
| 2013/0327677 A1 | 12/2013 | McDorman |
| 2014/0012185 A1 | 1/2014 | Ishizuka et al. |
| 2014/0134503 A1 | 5/2014 | Lockett et al. |
| 2014/0146266 A1 | 5/2014 | Zhang |
| 2014/0158604 A1 | 6/2014 | Chammas et al. |
| 2014/0248005 A1 | 9/2014 | David et al. |
| 2015/0306288 A1 | 10/2015 | Delorme et al. |
| 2016/0007588 A1 | 1/2016 | Levesque et al. |
| 2016/0242410 A9 | 8/2016 | Yoshida et al. |

FOREIGN PATENT DOCUMENTS

| | | |
|---|---|---|
| CN | 1195965 A | 10/1998 |
| CN | 2502700 Y | 7/2002 |
| CN | 1642628 A | 7/2005 |
| CN | 2780207 Y | 5/2006 |
| CN | 2894710 Y | 5/2007 |
| CN | 101039737 A | 9/2007 |
| CN | 103732056 | 4/2014 |
| DE | 3722984 | 1/1989 |
| DE | 10327988 A1 | 7/2004 |
| EP | 0 100 419 A2 | 2/1984 |
| EP | 0 217 759 A1 | 4/1987 |
| EP | 0 299 381 A2 | 1/1989 |
| EP | 0 890 368 A1 | 1/1999 |
| EP | 1109447 | 10/2003 |
| EP | 1 891 999 A1 | 2/2008 |
| EP | 2389064 | 11/2011 |
| EP | 2635114 | 9/2013 |
| EP | 2459247 A2 | 3/2016 |
| EP | 3 285 711 A1 | 10/2016 |
| EP | 3 268 015 A1 | 1/2018 |
| FR | 2 581 289 A1 | 11/1986 |
| FR | 2 996 413 A1 | 4/2014 |
| GB | 1 044 649 A2 | 10/1966 |
| GB | 2283015 A1 | 4/1995 |
| JP | 58-194879 | 11/1983 |
| JP | 59-115349 | 7/1984 |
| JP | 61-109577 A | 5/1986 |
| JP | 63-63616 A | 3/1988 |
| JP | 01-104271 A | 4/1989 |
| JP | 3-284263 | 12/1991 |
| JP | 5-503075 A | 5/1993 |
| JP | 5-503304 A | 6/1993 |
| JP | H05-148151 A | 6/1993 |
| JP | 5-305123 A | 11/1993 |
| JP | H05-317413 | 12/1993 |
| JP | 06-121920 A | 5/1994 |
| JP | 2668446 | 7/1997 |
| JP | 2700170 B2 | 1/1998 |
| JP | 10-501443 A | 2/1998 |
| JP | H10-507395 | 7/1998 |
| JP | 11-216179 | 8/1999 |
| JP | 2000-516963 A | 12/2000 |
| JP | 2001-500053 | 1/2001 |
| JP | 2001-523225 | 11/2001 |
| JP | 2002-087971 | 3/2002 |
| JP | 2002-253936 A | 9/2002 |
| JP | 2002-541941 | 12/2002 |
| JP | 2004-089495 A | 3/2004 |
| JP | 2005-533041 A | 11/2005 |
| JP | 2005-535279 A | 11/2005 |
| JP | 2005-535289 A | 11/2005 |
| JP | 2006-502078 A | 1/2006 |
| JP | 2006-515279 | 5/2006 |
| JP | 2006-213923 | 8/2006 |

(56) References Cited

FOREIGN PATENT DOCUMENTS

| | | |
|---|---|---|
| JP | 2007-260393 A | 10/2007 |
| JP | 2008-86996 | 4/2008 |
| JP | 2008-528066 | 7/2008 |
| JP | 2008-529550 A | 8/2008 |
| JP | 2008-253452 | 10/2008 |
| JP | 10/501443 | 2/2010 |
| JP | 2010-503501 A | 2/2010 |
| JP | 2010-116626 | 5/2010 |
| JP | 2010-535235 | 11/2010 |
| JP | 2010-538735 | 12/2010 |
| JP | 2011 000132 A | 1/2011 |
| JP | 2011-92905 | 5/2011 |
| JP | 2013-500794 | 1/2013 |
| JP | 2014-518283 | 7/2014 |
| JP | 2014-527436 | 10/2014 |
| JP | 2007-509206 A | 4/2017 |
| KR | 10-0721054 | 5/2006 |
| SU | 1718766 A1 | 1/1990 |
| WO | WO 1981/02239 A1 | 8/1981 |
| WO | WO 1986/00809 A1 | 2/1986 |
| WO | WO 1989/02274 A1 | 3/1989 |
| WO | WO 1991/04659 A1 | 4/1991 |
| WO | WO 1992/08348 A1 | 5/1992 |
| WO | WO 1995/29662 A2 | 11/1995 |
| WO | WO 1996/29103 A1 | 9/1996 |
| WO | WO 1996/29346 A1 | 9/1996 |
| WO | WO 1996/29864 A1 | 10/1996 |
| WO | WO 1996/39026 A1 | 12/1996 |
| WO | WO 1997/37628 A1 | 10/1997 |
| WO | WO 1998/046073 A1 | 10/1998 |
| WO | WO 1998/51147 A1 | 11/1998 |
| WO | WO 1999/25726 A1 | 5/1999 |
| WO | WO 1999/29346 A1 | 6/1999 |
| WO | WO 1999/48963 A2 | 9/1999 |
| WO | WO 2000/011946 A2 | 3/2000 |
| WO | WO 2000/0062891 | 10/2000 |
| WO | WO 2003/043419 A1 | 5/2003 |
| WO | WO 2003/043571 A2 | 5/2003 |
| WO | WO 2003/086577 A1 | 10/2003 |
| WO | WO 03/103390 A1 | 12/2003 |
| WO | WO 2004/043381 A2 | 5/2004 |
| WO | WO 2006/050328 A1 | 5/2006 |
| WO | WO 2006/057473 A1 | 6/2006 |
| WO | WO 2006/088455 A1 | 8/2006 |
| WO | WO 2009/126586 A2 | 10/2009 |
| WO | WO 2009/132839 A1 | 11/2009 |
| WO | WO 2011/014855 A2 | 2/2011 |
| WO | WO 2011/046841 A1 | 4/2011 |
| WO | WO 2011/046963 | 4/2011 |
| WO | WO 2011/068897 | 6/2011 |
| WO | WO 2012/027582 A1 | 3/2012 |
| WO | WO-2012027582 A1 * | 3/2012 ........... C12N 5/0641 |
| WO | WO 2012/061731 A1 | 5/2012 |
| WO | WO 2012/120927 A1 | 9/2012 |
| WO | WO 2013/006631 A1 | 1/2013 |
| WO | WO 2013/022491 A1 | 2/2013 |
| WO | WO 2013/023156 A1 | 2/2013 |
| WO | WO 2013/043658 A1 | 3/2013 |
| WO | WO 2013/153441 A1 | 10/2013 |
| WO | WO 2013/177339 A1 | 11/2013 |
| WO | WO 2014/134503 A1 | 9/2014 |
| WO | WO 2014/194931 A1 | 12/2014 |
| WO | WO 2016/145210 A1 | 9/2016 |
| WO | WO 2016/172645 A1 | 10/2016 |

OTHER PUBLICATIONS

Alcantar et al., "Polyethylene glycol-coated biocompatible surfaces," *Journal of Biomedical Materials Research*, 51(3):343-351 (2000).

Anderson et al., "Microfabrication and microfluidics for tissue engineering: state of the art and future opportunities," *Lab Chip*, 4:98-103 (2004).

Barbee et al., "The Fahraeus Effect," *Microvascular Research*, 3:6-16 (1971).

Barclay et al., "A Method for Detecting Chaos in Canine Myocardial Microcirculatory Red Cell Flux," *Microcirculation*, 7(5):335-346 (2000).

Bardy et al., "Technetium-99m Labeling by Means of Stannous Pyrophosphate: Application to Bleomycin and Red Blood Cells," *Journal of Nuclear Medicine*, 16(5):435-437 (1975).

Barras et al., "Influence of Rejuvenation on the Rheological Properties of Stored Erythrocytes," *VASA*, 23(4):305-311 (1994).

Bensinger et al., "Prolonged maintenance of 2,3-DPG in liquid blood storage: Use of an internal $CO_2$ trap to stabilize pH," *J. Lab. Clin. Med.*, 89(3):498-503 (1977).

Benson et al., "Accumulation of Pro-Cancer Cytokines in the Plasma Fraction of Stored Packed Red Cells," *J Gastrointest Surg.*, 16:460-468 (2012).

Beutler et al., "Storage of red cell concentrates in CPD-A2 for 42 and 49 days," *The Journal of Laboratory and Clinical Medicine*, 102(1):53-62 (1983).

Borenstein et al., "Microfabrication Technology for Vascularized Tissue Engineering," *Biomedical Microdevices*, 4(3):167-175 (2002).

Brody et al., "Deformation and Flow of Red Blood Cells in a Synthetic Lattice: Evidence for an Active Cytoskeleton," *Biophysical Journal*, 68:2224-2232 (1995).

Burns et al., "Artificial microvascular network: a new tool for measuring rheologic properties of stored red blood cells," *Transfusion*, 52(5):1010-1023 (2012).

Buskirk et al., "Accumulation of Biologic Response Modifiers During Red Blood Cell Cold Storage," *Transfusion*, 49(Suppl3):102A-103A (2009).

Carmen, "The Selection of Plastic Materials for Blood Bags," *Transfusion Medicine Reviews*, 7(1):1-10 (1993).

Carr et al., "Nonlinear Dynamics of Microvascular Blood Flow," *Annals of Biomedical Engineering*, 28:641-652 (2000).

Cell Deformability, RheoSCAN (RheoScan-AnD300/RheoScan-D300), obtained on Dec. 11, 2012, from: http://www.rheoscan.com/products/products/products-01.html.

Chaplin et al., "The Proper Use of Previously Frozen Blood Cells for Transfusion," *Blood*, 59:1118-1120 (1982).

Chilton et al., "Privacy Protection of Health Information: Patient Rights and Pediatrician Responsibilities," *Pediatrics*, 104(4):973-977 (1999).

Cognasse et al., "The role of microparticles in inflammation and transfusion: A concise review," *Transfus. Apher. Sci.* 53(2):159-167 (2015).

Cokelet et al., "Fabrication of in Vitro Microvascular Blood Flow Systems by Photolithography," *Microvascular Research*, 46:394-400 (1993).

Dale et al., "Human Vaccination with *Escherichia coli* J5 Mutant Induces Cross-Reactive Bactericidal Antibody against *Neisseria gonorrhoeae* Lipooligosaccharide," *The Journal of Infectious Diseases*, 166:316-325 (1992).

De Angelis et al., "Erythrocyte Shape Control in Stored Blood: The Effect of Additive Solutions on Shape Recovery," *Haematologica*, 73:7-12 (1988).

Deible et al., "Molecular barriers to biomaterial thrombosis by modification of surface proteins with polyethylene glycol," *Biomaterials*, 19:1885-1893 (1998).

De Korte et al., "Prolonged maintenance of 2,3-diphosphoglycerate acid and adenosine triphosphate in red blood cells during storage," *Transfusion*, 48:1081-1089 (2008).

De Venuto et al., "Rejuvenation of Human Red Blood Cells During Liquid Storage," *Transfusion*, 14(4):338-344 (1974).

Dumaswala et al., "Studies in Red Blood Cell Preservation: 9. The Role of Glutamine in Red Cell Preservation," *Vox Sang*, 67:255-259 (1994).

Dumaswala et al., "Glutamine- and Phosphate-Containing Hypotonic Storage Media Better Maintain Erythrocyte Membrane Physical Properties," *Blood*, 88(2):697-704 (1996).

Dumaswala et al., "Improved Red Blood Cell Preservation Correlates With Decreased Loss of Bands 3, 4.1, Acetylcholinestrase, and Lipids in Microvesicles," *Blood*, 87(4):1612-1616 (1996).

(56) References Cited

OTHER PUBLICATIONS

Dumont et al., "Anaerobic storage of red blood cells in a novel additive solution improves in vivo recovery," *Transfusion*, 49(3):458-464 (2009).
Dumont et al., "$CO_2$-dependent metabolic modulation in red cells stored under anaerobic conditions," *Transfusion* 56(2): 392-403 (2016)(epub 2015).
Durapore® Membrane Filters—Filter Discs and Membranes, retrieved on Aug. 26, 2014, from: www.emdmillipore.com/US/en/product/Durapore.
Effenhauser et al., "Integrated Capillary Electrophoresis on Flexible Silicone Microdevices: Analysis of DNA Restriction Fragments and Detection of Single DNA Molecules on Microchips," *Anal. Chem.*, 69:3451-3457 (1997).
European Search Report completed on Feb. 11, 2005, in European Patent Application No. 02 78 2307.9.
Extended European Search Report, dated Aug. 29, 2014 for European Patent Application No. 10823965.8.
Extended European Search Report dated Oct. 30, 2014 in European Patent Application No. 11838889.1.
Extended European Search Report dated Oct. 24, 2014 in European Patent Application No. 12807324.4.
Extended European Search Report dated Mar. 5, 2015, in European Patent Application No. 12821624.9.
Extended European Search Report dated Jun. 15, 2015, in European Patent Application No. 11820660.6.
Fahraeus et al., "The Viscosity of the Blood in Narrow Capillary Tubes," *Am. J Physiol.*, 96(3):562-568 (1931).
Fage et al., "On transition from laminar to turbulent flow in the boundary layer," The gamma-ray transition of radio-bromine, *Proceedings of the Royal Society*, 178(973):205-227 (1940).
Fang et al., "Inhibition of Lipopolysaccharide-Associated Endotoxin Activities In Vitro and In Vivo by the Human Anti-Lipid A Monoclonal Antibody SdJ5-1.17.15," *Infection and Immunity*, 61(9):3873-3878 (1993).
Fatouros et al., "Recombinant factor VII SQ—influence of oxygen, metal ions, pH and ionic strength on its stability in aqueous solution," *International Journal of Pharmaceutics*, 155(1):121-131 (1997).
Frame et al., "A System for Culture of Endothelial Cells in 20-50-µm Branching Tubes," *Microcirculation*, 2(4):377-385 (1995).
"Friction Factor for Flow in Coils and Curved Pipe," Neutrium Available on the world wide web at neutrium.net/fluid_flow/friction-factor-for-flow-in-coils-and-curved-pipe/. (2017).
Fung et al., "High-Resolution Data on the Geometry of Red Blood Cells", *Biorheology*, 18:369-385 (1981).
Gañán-Calvo et al., "Current and Droplet Size in the Electrospraying of Liquids. Scaling Laws," *J. Aerosol Sci.*, 28(2):249-275 (1997).
Gifford et al, "Parallel Microchannel-Based Measurements of Individual Erythrocyte Areas and Volumes," *Biophysical Journal*, 84:623-633 (2003).
Gifford et al, "A detailed study of time-dependent changes in human red blood cells: from reticulocyte maturation to erythrocyte senescence," *British Journal of Haematology*, 135:395-404 (2006).
Green et al., "10. Liposomal Vaccines," Immunobiology of Proteins and Peptides VII, Plenum Press, New York, pp. 83-92 (1995).
Greenwalt et al., "Studies in Red Blood Cell Preservation. 7. In vivo and in Vitro Studies with a Modified Phosphate-Ammonium Additive Solution," *Vox Sang*, 65:87-94 (1993).
Greenwalt et al., "Studies in Red Blood Cell Preservation. 8. Liquid Storage of Red Cells in Glycerol-Containing Additive Solution," *Vox. Sang*, 67:139-143 (1994).
Greenwalt et al., "Studies in red blood cell preservation. 10. $^{51}Cr$ Recovery of Red Cells after Liquid Storage in a Glycerol-Containing Additive Solution," *Vox Sang*, 70:6-10 (1996).
Greenwalt et al., "The effect of hypotonicity, glutamine, and glycine on red cell preservation," *Transfusion*, 37:269-276 (1997).
Griffith, "Temporal chaos in the microcirculation," *Cardiovascular Research*, 31:342-358 (1996).
Grigioni et al., "A discussion on the threshold limited for nemo lysis related to Reynolds shear stress," *J. Biomech.*, 32:1107-1112 (1999).
Gulliksson et al., "Storage of whole blood overnight in different blood bags preceding preparation of blood components: in vitro effects on red blood cells," *Blood Transfus* 7:210-215 (2009).
Hamasaki et al., "Acid-citrate-dextrose-phosphoenolpyruvate medium as a rejuvenant for blood storage," *Transfusion*, 23(1):1-7 (1983).
Heaton et al., "Use of Adsol preservation solution for prolonged storage of low viscosity AS-1 red blood cells," *Br J. Haematol*, 57(3):467-478 (1984).
Hess, "Extended Liquid Storage of Red Blood Cells," Blood Donors and the Supply of Blood and Blood Products, National Academy Press, Washington, D.C., pp. 99-102 (1996).
Hess et al., "Successful storage of RBCs for 9 weeks in a new additive solution," *Transfusion*, 40:1007-1011 (2000).
Hess, "Storage of red blood cells under anaerobic conditions," *Vox Sanguinis*, 93:183 (2007).
Hess et al., "Alkaline CPD and the preservation of RBC 2,3-DPG," *Transfusion*, 42:747-752 (2002).
Hess et al., "Storage of Red Blood Cells: New Approaches," *Transfusion Medicine Reviews*, 16(4):283-295 (2002).
Hodgson et al., "Prophylactic use of human endotoxin-core hyperimmune gammaglobulin to prevent endotoxaemia in colostrum-deprived, gnotobiotic lambs challenged orally with *Escherichia coli*," *FEMS Immunology and Medical Microbiology*, 11:171-180 (1995).
Högman et al., "Cell Shape and Total Adenylate Concentration as Important Factors for Posttransfusion Survival of Erythrocytes," *Biomed. Biochim. Acta*, 42:S327-S331 (1983).
Högman et al., " Effects of Oxygen on Red Cells during Liquid Storage at +4° C," *Vox Sang.*, 51:27-34 (1986).
Högman et al., "Effects of oxygen and mixing on red cells stored in plastic bags at +4° C," *Biomed. Biochim. Acta.*, 46:S290-S294 (1987).
Högman et al., "Shall Red Cell Units Stand Upright, Lie Flat or be Mixed During Storage? In Vitro Studies of Red Cells Collected in 0.5 CPD and Stored in RAS2 (Erythrosol®)," *Transfus. Sci.*, 16(2):193-199 (1995).
Högman, "Preparation and Preservation of Red Cells," *Vox Sanguinis* 74(Suppl. 2):177-187 (1998).
Holme et al., "Current Issues Related to the Quality of Stored RBCs," *Transfusion and Apheresis Science*, 33(1):55-61 (2005).
Huang et al., "Continuous Particle Separation Through Deterministic Lateral Displacement," *Science*, 304:987-990 (2004).
International Committee for Standardization in Hematology, "Recommended Methods for Radioisotope Red Cell Survival Studies," *Blood* 38(3):378-386 (1971).
International Preliminary Report on Patentability dated Feb. 18, 2011 (completed on Feb. 8, 2012), in International Patent Application No. PCT/US2010/52084.
International Preliminary Report on Patentability dated May 24, 2012 (completed on May 21, 2012), in International Patent Application No. PCT/US2010/52376.
International Search report Completed on Feb. 8, 2011, in International Patent Application No. PCT/US10/52084.
International Preliminary Report on Patentability completed on Oct. 18, 2011, in International Patent Application No. PCT/US2010/031055.
International Search Report completed on Jul. 8, 1996, in International Patent Application No. PCT/US96/09005.
International Search Report completed on Nov. 10, 2003, in International Patent Application No. PCT/US02/36735.
International Search Report completed on May 20, 2010, in International Patent Application No. PCT/US2010/31055.
International Search Report and Written Opinion dated Dec. 6, 2010 for corresponding International Patent Application No. PCT/US2010/052376.
International Search Report dated Apr. 27, 2011(completed on Apr. 26, 2011), in International Patent Application No. PCT/US2010/044045.
International Search Report completed on Dec. 21, 2011, in International Patent Application No. PCT/US11/49168.

(56) References Cited

OTHER PUBLICATIONS

International Search Report completed on Feb. 12, 2012, in International Patent Application No. PCT/US11/59372.
International Search Report completed on Jun. 18, 2012, in International Patent Application No. PCT/US12/30930.
International Search Report completed on Sep. 24, 2012, in International Patent Application No. PCT/US12/50380.
International Search Report and Written Opinion issued in International Application PCT/US2014/019537 dated Jul. 10, 2014.
International Search Report completed on Nov. 9, 2012 issued in International Patent Application No. PCT/US12/045426 (dated Nov. 26, 2012).
International Search Report for PCT/US2016/021794 dated Jul. 18, 2016.
International Search Report for PCT/US2016/051115 dated Nov. 21, 2016.
International Search Report for PCT/US2017/034410 dated Dec. 22, 2017.
Irsch et al., "Pathogen inactivation of platelet and plasma blood components for transfusion using the INTERCEPT Blood System™," *Transfusion Medicine and Hemotherapy*, 38:19-31 (2011).
Jain, et al., "Determinants of Leukocyte Margination in Rectangular Microchannels," *PLoS One*, 4(9):1-8 (2009).
Jarus et al., "Barrier Properties of polypropylene/polyamide blends produced by microlayer coextrusion," *Polymer* 43:2401-2408 (2002).
Jayasinghe et al., "Controlled deposition of nanoparticle clusters by electrohydrodynamic atomization," *Nanotechnology*, 15:1519-1523 (2004).
Jiang et al., "Microfluidic synthesis of monodisperse PDMS microbeads as discrete oxygen sensors," *Soft Matter*, 8:923-926 (2011).
Jo et al., "Surface modification using silanated poly(ethylene glycol)s," *Biomaterials*, 21:605-616 (2000).
Johnson et al., "Regulation of blood flow in single capillaries," *American Journal of Physiology*, 212:1405-1415 (1967).
Kaihara et al., "Silicon Micromachining to Tissue Engineer Branched Vascular Channels for Liver Fabrication," *Tissue Engineering*, 6(2):105-117 (2000).
Kaiser-Guignard et al., "The clinical and biological impact of new pathogen inactivation technologies on platelet concentrates," *Blood Reviews* 28:235-241 (2014).
Kakaiya et al., "Platelet preservation in large containers," *Vox Sanguinis*, 46(2):111-118 (1984).
Kiani et al., "Fluctuations in microvascular blood flow parameters caused by hemodynamic mechanisms," *American Journal of Physiology*, 266(5):H1822-H1828 (1994).
Kikuchi et al., "Modified Cell-Flow Microchannels in a Single-Crystal Silicon Substrate and Flow Behavior of Blood Cells," *Microvascular Research*, 47:126-139 (1994).
Kilkson et al., "Platelet metabolism during storage of platelet concentrates at 22° C.," *Blood* 64(2):406-414 (1984).
Koch et al., "Peripheral blood leukocyte NO production and oxidative stress in multiple sclerosis," *Multiple Sclerosis*, 14:159-165 (2008).
Koch et al., "Duration of Red-Cell Storage and Complications After Cardiac Surgery," *The New England Journal of Medicine*, 358:1229-1239 (2008).
Krogh, "Studies on the physiology of capillaries. II. The reactions to local stimuli of the blood-vessels in the skin and web of the frog," *The Journal of Physiology*, 55:412-422 (1921).
Kuraoka, et al., "Ship-in-a-bottle synthesis of a cobalt phthalocyanine/porous glass composite membrane for oxygen separation," *Journal of Membrane Science*, 286(1-2):12-14 (2006).
Kynar Flex Product Catalog, downloaded May 20, 2015 from Kynar.com.
Lowndes, "Blood Interference in fluorescence spectrum: Experiment, analysis and comparison with intraoperative measurements on brain tumor," *Bachelor Thesis*, Linköping University, pp. 1-42 (2010).
Lugowski et al., "Anti-endotoxin antibodies directed against *Escherichia coli* R-1 oligosaccharide core-tetanus toxoid conjugate bind to smooth, live bacteria and smooth lipopolysaccharides and attenuate their tumor necrosis factor stimulating activity," *FEMS Immunology and Medical Microbiology*, 16:31-38 (1996).
Lundblad, "Factor VIII—Reducing agents, copper ions, and stability," http://lundbladbiotech.com.
Mazor et al., "Prolonged Storage of Red Cells: The Effect of pH, Adenine Phosphate," *Vox Sanguinis*, 66:264-269 (1994).
McDonald et al., "Poly(dimethylsiloxane) as a Material for Fabricating Microfluidic Devices," *Accounts of Chemical Research*, 35(7):491-499 (2002).
Meryman et al., "Prolonged storage of red cells at 4° C," *Transfusion*, 26(6):500-505 (1986).
Meryman et al., "Extending the storage of red cells at 4° C," *Transfus. Sci.*, 15(2):105-115 (1994).
Moll et al., "Dean vortices applied to membrane process. Part II: Numerical approach," *Journal of Membrane Science*, 288:321-335 (2007).
Moroff et al., "Factors Influencing Changes in pH during Storage of Platelet Concentrates at 20-24° C," *Vox Sanguinis*, 42(1):33-45 (1982).
Moroff et al., "Proposed standardization of methods for determining the 24-hour survival of stored red cells," *Transfusion*, 24:109-114 (1984).
Moroff et al., "Concepts about current conditions for the preparation and storage of platelets," *Transfus Med Rev* V(1):48-59 (1991).
Murphy et al., "Platelet storage at 22° C: role of gas transport across plastic containers in maintenance of viability," *Blood* 46(2):209-218 (1975).
Murphy et al., "Increased Mortality, Postoperative Morbidity, and Cost After Red Blood Cell Transfusion in Patients Having Cardiac Surgery," *Circulation*, 116:2544-2552 (2007).
Musante et al., "Active Focal Segmental Glomerulosclerosis is Associated with Massive Oxidation of Plasma Albumin," *Journal of the American Society of Nephrology*, 18(3):799-810 (2007).
Ng et al., "Components for integrated poly(dimethylsiloxane) microfluidic systems," *Electrophoresis*, 23:3461-3473 (2002).
Ohkuma et al., "The preservative-exchange method using a sextuple-bag system for a 10-week storage period of red blood cells," *Transfusion Medicine*, 1:257-262 (1991).
Parkkinen et al., "Plasma ascorbate protects coagulation factors against photooxidation," *Thromb Haemost* 75(2):292-297 (1996).
Picker et al., "Current methods for the reduction of blood-borne pathogens: a comprehensive literature review," *Blood Transfusion* 11:343-348 (2013).
Pidcoke et al., "Primary hemostatic capacity of whole blood: a comprehensive analysis of pathogen reduction and refrigeration effects over time," *Transfusion* 53:137S-149S (2013).
Poncelet et al., "Tips and tricks for flow cytometry-based analysis and counting of microparticles," *Transfus. Apher. Sci.* 53(2):110-126 (2015).
Poxton, "Antibodies to lipopolysaccharide," *Journal of Immunological Methods*, 186:1-15 (1995).
Prefiltration before membrane filtration, hydrophobic, 25 μm 142 mm, retrieved on Aug. 26, 2014, from: www.emdmillipore.com/US/en/product/Prefiltration-before-membrane-filtration.
Pries et al., "Biophysical aspects of blood flow in the microvasculature," *Cardiovascular Research*, 32:654-667 (1996).
Ramstack et al., "Shear-induced activation of platelets," *J. Biomech.*, 12:113-125 (1979).
Rock et al., "Nutricel as an additive solution for neonatal transfusion," *Transfusion Science*, 20:29-36 (1999).
Sambuceti et al., "Why should we study the coronary microcirculation?," *Am J Physiol Heart Circ Physiol*, 279:H2581-H2584 (2000).
Schubert et al., "Whole blood treated with riboflavin and ultraviolet light: Quality assessment of all blood components produced by the buffy coat method," *Transfusion* 55(4):815-823 (2014).
Sheffield et al., "Changes in coagulation factor activity and content of di(2-ethylhexyl) phthate in frozen plasma units during refrigerated storage for up to 5 days after thawing," *Transfusion*, 52:494-502 (2012).
Shevkoplyas et al., "Direct measurement of the impact of impaired erythrocyte deformability on microvascular network perfusion in a microfluidic device," *Lab Chip*, 6:914-920 (2006).

(56) References Cited

OTHER PUBLICATIONS

Shimizu et al., "Multicenter Clinical Evaluation of Red Cell Concentrates Stored up to 6 Weeks in MAP, a new additive solution," *Japanese Journal of Clinical Hematology*, 33(2):148-156 (1992).
Skalak et al., "Deformation of Red Blood Cell in Capillaries," *Science*, 164(3880):717-719 (1969).
Sohmer et al., "Phosphoenolypyruvate (PEP) Effects on Fresh and Stored Red Blood Cells," *Proceedings of the Society for Experimental Biology and Medicine*, 171:24-33 (1982).
Su et al., "Impermeable barrier films and protective coatings based on reduced graphene oxide," *Nature Communications* 5 Article No. 4843 (2014).
Supplementary European Search Report dated Jan. 20, 2015 in European Patent Application No. 12822378.2.
Sutera et al., "Deformation and Fragmentation of Human Red Blood Cells in Turbulent Shear Flow," *Biophys. J.*, 15:1-10 (1975).
Sutton et al., "A Novel Instrument for Studying the Flow Behaviour of Erythrocytes through Microchannels Simulating Human Blood Capillaries," *Microvascular Research*, 53:272-281 (1997).
Szymanski et al., "Effect of rejuvenation and frozen storage on 42-day-old AS-1 RBCs," *Transfusion*, 41:550-555 (2001).
Tinmouth et al., "The Clinical Consequences of the Red Cell Storage Lesion," *Transfusion Medicine Reviews*, 15(2):91-107 (2001).
Tracey et al., "A Silicon Micromachined Device for Use in Blood Cell Deformability Studies," *IEEE Transactions on Biomedical Engineering*, 42(8):751-761 (1995).
"Transition and Turbulence," https://www.princeton.edu/~asmits/Bicycle_web/transition.html . Adapted from The Engine and the Atmosphere: An Introduction to Engineering by Z. Warhaft, Cambridge University Press, (1997).
Tsukada et al., "Direct Measurement of Erythrocyte Deformability in Diabetes Mellitus with a Transparent Microchannel Capillary Model and High-Speed Video Camera System," *Microvascular Research*, 61:231-239 (2001).
Valeri et al., "The survival, function, and hemolysis of human RBCs stored at 4° C in additive solution (AS-1, AS-3, or AS-5) for 42 days and then biochemically modified, frozen, thawed, washed, and stored at 4° C in sodium chloride and glucose solution for 24 hours," *Transfusion*, 40:1341-1345 (2000).
Wallvik et al., "Platelet Concentrates Stored at 22° C Need Oxygen the Significance of Plastics in Platelet Preservation," *Vox Sanguinis*, 45(4):303-311 (1983).
Wallvik et al., "The platelet storage capability of different plastic containers," *Vox Sanguinis*, 58(1):40-44 (1990).
Wang et al., "Fabrication of PLGA microvessel scaffolds with circular microchannels using soft lithography," *Journal of Micromechanics and Microengineering*, 17(10):2000-2005 (2007).
Weinberg et al., "Transfusions in the Less Severely Injured: Does Age of Transfused Blood Affect Outcomes?," *The Journal of TRAUMA*, 65(4):794-798 (2008).
Wilding et al., "Manipulation and Flow of Biological Fuids in Straight Channels Micromachined in Silicon," *Clinical Chemistry*, 40(1):43-47 (1994).
Wood et al., "The Viability of Human Blood Stored in Phosphate Adenine Media," *Transfusion* 7, 401-408 (1967).
Wu et al., "Polymer microchips bonded by $O_2$-plasma activation," *Electrophoresis*, 23:782-790 (2002).
Yazer et al., "Coagulation factor levels in plasma frozen within 24 hours of phlebotomy over 5 days of storage at 1 to 6° C," *Transfusion*, 48:2525-2530 (2008).
Yoshida et al., "Extended storage of red blood cells under anaerobic conditions," *Vox Sanguinis*, 92:22-31 (2007).
Yoshida et al., "Storage of red blood cells under anaerobic conditions: reply," *Vox Sanguinis*, 93:184 (2007).
Yoshida et al., "The effects of additive solution pH and metabolic rejuvenation on anaerobic storage of red cells," *Transfusion*, 48:2096-2105 (2008).
Zhang et al., "Modification of Si(100) surface by the grafting of poly(ethylene glycol) for reduction in protein adsorption and platelet adhesion," *J Biomed Mater Res*, 56:324-332 (2001).
Zimrin et al., "Current issues relating to the transfusion of stored red blood cells," *Vox Sanguinis*, 96:93-103 (2009).
Zimring et al., "Established and theoretical factors to consider in assessing the red cell storage lesion," *Blood*, 125:2185-2190 (2015).
Cardo et al., "Pathogen inactivation of *Leishmania donovani* infantum in plasma and platelet concentrates using riboflavin and ultraviolet light," *Vox Sanguinis* 90:85-91 (2006).
Cardo et al., "Pathogent inactivation of *Trypanosoma cruzi* in plasma and platet concentrates using riboflavin and ultraviolet light," *Transfusion and Apheresis Science* 37:131-137 (2007).
Corbin, "Pathogen Inactivation of Blood Components: Current Status and Introduction of an Approach Using Riboflavin as a Photosensitizer," International Journal of Hematology Supplement II 76:253-257 (2002).
Erickson et al., "Evaluation of in vitro Quality of Stored RBC after Treatment with S303 Pathogen Inactivation at Varying Hematocrits," Transfusion DUP—General Collection 48(2) Supplement (2008).
Fast et al., "Inactivation of Human White Blood Cells in Red Blood Cell Products Using the Mirasol® System for Whole Blood," Blood Abstract #2897 110(11)(pt. 1) (2007).
Goodrich, "The Use of Riboflavin for the Inactivation of Pathogens in Blood Products," Vox Sanguinis Suppl. 2 78:211-215 (2000).
International Search Report for PCT/US2016/033151 dated Oct. 13, 2016.
Janetzko et al., "Pathogen reduction technology (Mirasol®) treated singledonor platelets resuspended in a mixture of autologous plasma and PAS," Vox Sanguinis 97:234-239 (2009).
Vrielink et al., "Transfusion-transmissible infections," Current Opinion in Hematology 5:396-405 (1998).
International Search Report dated Oct. 13, 2016 in International Appln. No. PCT/US2016/033151.
Reynolds et al., "S-nitrosohemoglobin deficiency: A mechanism for loss of physiological activity in banked blood," Proceedings of the National Academy of Sciences, 104(43):17058-17062 (2007).
Yoshida et al., "Anaerobic storage of red blood cells," *Blood Transfusion* 8:220-236 (2010).
Extended European Search Report dated Oct. 9, 2018, in European Patent Application No. 16784043.8.
Mollison, "The Introduction of Citrate as an Anticoagulant for Transfusion and of Glucose as a Red Cell Preservative," *British Journal of Haematology* 108:1318 (2000).
Agarwal et al., "Effect of pre-storage gamma irradiation on red blood cells," *Indian Journal of Medical Research* 122(5):385 (2005).
Apstein, et al., "Effect of erythrocyte storage and oxyhemoglobin affinity changes on cardiac function," *Am J. Physiol* 248: H508-15 (1985).
Aydogan, et al., "Impaired erythrocytes deformability in $H(2)O(2)$-induced oxidative stress: protective effect of L-carnosine," *Clin Hemorheol Microcirc* 39: 93-8 (2008).
Babic, "In vitro function and phagocytosis of galactosylated platelet concentrates after long-term refrigeration," *Transfusion* 47: 442-51 (2007).
Becker, et al., "Studies of platelet concentrates stored at 22 C nad 4 C," *Transfusion* 13: 61-8 (1973).
Benesch, et al., "The effect of organic phosphates from the human erythrocyte on the allosteric properties of hemoglobin," *Biochem Biophys Res Commun* 26: 162-7 (1967).
Bersin. et al., "Importance of oxygen-haemoglobin binding to oxygen transport in congestive heart failure," *Br Heart J* 70: 443-7 (1993).
Bordbar, et al., "Identified metabolic signature for assessing red blood cell unit quality is associated with endothelial damage markers and clinical outcomes," *Transfusion* 56: 852-62 (2016).
Browne, et al., "The molecular pathobiology of cell membrane iron: the sickle red cell as a model" *Free Radic Biol Med* 24: 1040-8 (1998).
Browne, et al., "Removal of erythrocyte membrane iron in vivo ameliorates the pathobiology of murine thalassemia," *J Clin Invest* 100: 1459-64 (1997).
Burns, et al., "Anaerobic Storage Improves the Mechanical Properties of Stored Red Blood Cells," *Transfusion* 52: 83A (2012).
Burns, et al., "Deterioration of red blood cell mechanical properties is reduced in anaerobic storage," *Blood Transfus* 14: 80-8 (2016).

(56) References Cited

OTHER PUBLICATIONS

Cabrales, et al., "Microvascular pressure and functional capillary density in extreme hemodilution with low-and high-viscosity dextran and a low-viscosity Hb-based 02 carrier," *American Journal of Physiology-Heart and Circulatory Physiology* 287: H363-H73 (2004).
Cabrales, et al., "Plasma viscosity regulates systemic and microvascular perfusion during acute extreme anemic conditions," *Am J. Physiol Heart Circ Physiol* 291: H2445-52 (2006).
Cannon et al., "Damage control resuscitation in patients with severe traumatic hemorrhage: A practice management guideline from the Eastern.Association for the Surgery of Trauma," *J Trauma Acute Care Surg* 82: 605-17 (2017).
Cap et al., "Whole Blood Transfusion," *Military Medicine* 183, 9/10:44 (2018).
Chanutin, et al., "Effect of organic and inorganic phosphates on the oxygen equilibrium of human erythrocytes," *Arch Biochem Biophys* 121: 96-102 (1967).
Chatpun, et al., "Cardiac mechanoenergetic cost of elevated plasma viscosity after moderate hemodilution," *Biorheology* 47: 225-37 (2010).
Chatpun, et al., "Cardiac systolic function recovery after hemorrhage determines survivability during shock," *J Trauma* 70: 787-93 (2011).
Chatpun, et al., "Effects of plasma viscosity modulation on cardiac function during moderate hemodilution," *Asian J Transfus Sci* 4: 102-8 (2010).
Choi, et al., "Influence of storage temperature on the responsiveness of human platelets to agonists," *Ann Clin Lab Sci* 33: 79-85 (2003).
Chouchani, et al., "Ischaemic accumulation of succinate controls reperfusion injury through mitochondrial ROS," *Nature* 515: 431-5 (2014).
Coene. "Paired analysis of plasma proteins and coagulant capacity after treatment with three methods of pathogen reduction," *Transfusion* 54: 1321-31 (2014).
Cotton et al., "A Randomized Controlled Pilot Trial of Modified Whole Blood Versus Component Therapy in Severely Injured Patients Requiring Large Volume Transfusions," *Annals of Surgery* 258(4) (2013).
D'Alessandro, et al., "Heterogeneity of blood processing and storage additives in different centers impacts stored red blood cell metabolism as much as storage time: lessons from REDS-11I-Omics," *Transfusion* 59: 89-100 (2019).
D'Alessandro, et al., "Time-course investigation of SAGM-stored leukocyte-filtered red bood cell concentrates: from metabolism to proteomics," *Haematologica* 97: 107-15 (2012).
D'Alessandro, et al., "Red blood cell metabolism under prolonged anaerobic storage," *Mol Biosyst* 9: 1196-209 (2013).
D'Alessandro, et al., "Red blood cell metabolic responses to refrigerated storage, rejuvenation, and frozen storage," *Transfusion* 57: 1019-30 (2017).
D'Alessandro, et al., "Metabolomics of AS-5 RBC supernatants following routine storage," *Vox Sang* (2014).
D'Alessandro, et al., "An update on red blood cell storage lesions, as gleaned through biochemistry and omics technologies," *Transfusion* 55: 205-19 (2015).
D'Alessandro, et al., "Red blood cell storage and clinical outcomes: new insights," *Blood Transfus* 15: 101-3 (2017).
D'Alessandro, et al., "Plasma succinate is a predictor of mortality in critically injured patients," *Journal of Trauma and Acute Care Surgery* 83: 491-5 (2017).
D'Alessandro, et al., "Plasma First Resuscitation Reduces Lactate Acidosis, Enhances Redox Homeostasis, Amino Acid and Purine Catabolism in a Rat Model of Profound Hemorrhagic Shock," *Shock* 46: 173-82 (2016).
D'Alessandro, et al., "Anaerobic storage Condition enhances GSH Levels while Maintaining Pentose Phosphate Pathway Activity," *Transfusion* 56: 51A (2016).
D'Alessandro, et al., "Red blood cell storage in additive solution-7 preserves energy and redox metabolism: a metabolomics approach," *Transfusion* 55: 2955-66 (2015).
D'Alessandro, et al., "Routine storage of red blood cell (RBC) units in additive solution-3: a comprehensive investigation of the RBC metabolome," *Transfusion* 55: 1155-68 (2015).
D'Alessandro, et al., "Omics markers of the red cell storage lesion and metabolic linkage," *Blood Transfus* 15: 137-44 (2017).
D'Alessandro, et al., "AltitudeOmics: Red Blood Cell Metabolic Adaptation to High Altitude Hypoxia," *J Proteome Res* 15: 3883-95 (2016).
D'Alessandro, et al., "Citrate metabolism in red blood cells stored in additive solution-3," *Transfusion* 57: 325-36 (2017).
D'Alessandro, et al., "Metabolic effect of alkaline additives and guanosine/gluconate in storage solutions for red blood cells," *Transfusion* 58: 1992-2002 (2018).
D'Alessandro, et al., "Effects of aged stored autologous red blood cells on human plasma metabolome," *Blood Adv* 3: 884-96 (2019).
D'Alessandro, et al., "Hitchhiker's guide to the red cell storage galaxy: Omics technologies and the quality issue," *Transfus Apher Sci* 56: 248-53 (2017).
D'Amici, et al., "Red blood cell storage in SAGM and AS3: a comparison through the membrane two-dimensional electrophoresis proteome," *Blood Transfusion* = *Trasfusione del sangue* 10 Suppl 2: s46-54 (2012).
De Wolski, et al., "Metabolic pathways that correlate with post-Transfusion circulation of stored murine red blood cells," *Haematologica* 101: 578-86 (2016).
Delgado, et al., "Platelet Function in Stored Whole Blood Measured by a Shear- and Von Willebrand Factor-Dependent Methodology is Retained During Storage at 4° C for up to 7 Days," *Transfusion* 51: 65A (2011).
Dennis, et al., "Transfusion of 2,3 DPG-enriched red blood cells to improve cardiac function," *Ann Thorac Surg* 26: 17-6 (1978).
Dennis, et al., "Improved myocardial performance following high 2-3 diphosphoglycerate red cell transfusions," *Surgery* 77: 741-7 (1975).
Dumont, et al., "Randomized cross-over in vitro and in vivo evaluation of a prototype anaerobic conditioning and storage system vs. standard aerobic storage," *Vox Sang* 103: 123 (2012).
Dumont et al., "Performance Of Anaerobic Stored Red Blood Cells Prepared Using A Prototype 02 & $CO_2$ Depletion And Storage System," *Transfusion* 51s: SP89 (2011).
European Search Report dated Jun. 18, 2019, in European Patent Application No. 19163305.6.
Extended European Search Report dated Apr. 16, 2019, in European Patent Application No. 16845192.0.
Extended European Search Report dated Jun. 5, 2019, in European Patent Application No. 19158815.1.
Ezuki et al., "Survival and recoery of apheresis platelets stored in a polyolefin container with high oxygen permeability," *Vox Sanguinis* 94:292-298 (2008).
Farber, et al., "Effect of decreased 02 affinity of hemoglobin on work performance during exercise in healthy humans," *J Lab Clin Med* 104: 166-75 (1984).
Feys. "Oxygen removal during pathogen inactivation with riboflavin and UV light preserves protein function in plasma for Transfusion," *Vox Sang* 106: 307-15 (2013).
Friesenecker, et al., "Arteriolar vasoconstrictive response: comparing the effects of arginine vasopressin and norepinephrine," *Crit Care* 10: R75 (2006).
Gehrke, et al., "Metabolomics evaluation of early-storage red blood cell rejuvenation at 4 degrees C and 37 degrees C," *Transfusion* 58: 1980-91 (2018).
Gevi, et al., "Alterations of red blood cell metabolome during cold liquid storage of erythrocyte concentrates in CPD-SAGM," *J Proteomics* 76 Spec No. 168-80 (2012).
Golan, et al., "Transfusion of fresh whole blood stored (4 degrees C) for short period fails to improve platelet aggregation on extracellular matrix and clinical hemostasis after cardiopulmonary bypass," *J Thorac Cardiovasc Surg* 99: 354-60 (1990).
Haddaway, et al., "Hemostatic properties of cold-stored whole blood leukoreduced using a platelet-sparing versus a non-platelet-sparing filter," *Transfusion* (2019).
Hebbel, et al., Oxidation-induced changes in microrheologic properties of the red blood cell membrane. *Blood* 1990;76: 1015-20.

(56) References Cited

OTHER PUBLICATIONS

Hebbel. "Auto-oxidation and a membrane-associated 'Fenton reagent': a possible explanation for development of membrane lesions in sickle erythrocytes," *Clin Haematol* 14: 129-40 (1985).
Hershko. "Mechanism of iron toxicity and its possible role in red cell membrane damage," *Semin Hematol* 26: 277-85 (1989).
Hess, et al., "Advances in military, field, and austere Transfusion medicine in the last decade," *Transfus Apher Sci* 49: 380-6 (2013).
Hornsey, et al., "Cold storage of pooled, buffy-coat-derived, leucoreduced platelets in plasma," *Vox Sang* 95: 26-32 (2008).
Jagannathan, et al., "Oxidative stress under ambient and physiological oxygen tension in tissue culture," *Curr Pharmacol Rep* 2: 64-72 (2016).
Jarman, et al., "Rural risk: Geographic disparities in trauma mortality," *Surgery* 160: 1551-9 (2016).
Jarolim, et al., "Effect of hemoglobin oxidation products on the stability of red cell membrane skeletons and the associations of skeletal proteins: correlation with a release of them in," *Blood* 76: 2125-31 (1990).
Jenkins, et al., "Trauma hemostasis and oxygenation research position paper on remote damage control resuscitation: definitions, current practice, and knowledge gaps," *Shock* 41 Suppl 1: 3-12 (2014).
Jesch, et al., "Oxygen dissociation after Transfusion of blood stored in ACD or CPD solution," *J Thorac Cardiovasc Surg* 70: 35-9 (1975).
Jobes, et al., "Toward a definition of "fresh" whole blood: an in vitro characterization of coagulation properties in refrigerated whole blood for Transfusion," *Transfusion* 51: 43-51 (2011).
Jy, et al., "Release of Microparticles During Blood Storage Is Influenced by Residual Platelets, Leukocytes and Oxygen Levels," *Blood* 120: 3435 (2012).
Kerger, et al., "Systemic and subcutaneous microvascular $pO_2$ dissociation during 4-h hemorrhagic shock in conscious hamsters," *Am J. Physiol* 270: H827-H36 (1996).
Khorana, et al, "Blood Transfusions, thrombosis, and mortality in hospitalized patients with cancer," *Arch Intern Med* 168: 2377-81 (2008).
Kohli et al., "Packed red cells versus whole blood transfusion for severe paediatric anaemia, pregnancy-related anaemia and obstetric bleeding: an analysis of clinical proactice buidelines from sub-Saharan Africa and evidence underpinning recommendments," *Tropical Medicine and International Health* 24(1):11-22 (2019).
Korsten, et al., "Determination of%502 in More Than 1300 Fresh Erythrocyte Concentrates by Resonance Raman Spectroscopy," *Transfusion* 58: 215A (2018).
Kotwal, et al., "The Effect of a Golden Hour Policy on the Morbidity and Mortality of Combat Casualties," *JAMA Surg* 151: 15-24 (2016).
Kreuger, et al., "A clinical evaluation of citrate-phosphate-dextrose-adenine blood," *Vox Sang* 29: 81-9 (1975).
Kwan,et al., "Microfluidic analysis of cellular deformability of normal and oxidatively damaged red blood cells," *Am J Hematol* 88: 682-9 (2013).
Liu, et al., "Beneficial Role of Erythrocyte Adenosine A2B Receptor-Mediated AMP-Activated Protein Kinase Activation in High-Altitude Hypoxia," *Circulation* 134: 405-21 (2016).
Manno, et al., "Comparison of the hemostatic effects of fresh whole blood, stored whole blood, and components after open heart surgery in children," *Blood* 77: 930-6 (1991).
Miller. "New evidence in trauma resuscitation-is 1: 1: 1 the answer?" *Perioperative medicine* 2: 13 (2013).
Mussano et al., "Cytokine, chemokine and growth factor profile of Platelet Rich Plasma," *Universita Degli Studi Di Tornio* 2016.
Nair, et al., "Cold-Stored Platelets in PAS Exhibit Superior Hemostatic Potential" *Blood* 126: 772 (2015) Abstract.
Nemkov , et al., "Metabolomics in Transfusion medicine," *Transfusion* 56: 980-93 (2015).
Nemkov,et al., "Hypoxia modulates the purine salvage pathway and decreases red blood cell and supernatant levels of hypoxanthine during refrigerated storage," *Haematologica* 103: 361-72 (2018).
Nemkov, et al., "Metabolism of Citrate and Other Carboxylic Acids in Erythrocytes As a Function of Oxygen Saturation and Refrigerated Storage," *Front Med* (Lausanne) 4: 175 (2017).
Nessen et al., "Fresh whole blood use by forward surgical teams in Afghanistan is associated with improved survival compared to component therapy without platelets," *Transfusion* 53:107S-113S (2013).
Nilsson, et al., "Association between venous thromboembolism and perioperative allogeneic Transfusion," *Arch Surg* 142: 126-32; discussion 33 (2007).
Paglia,et al., "Biomarkers defining the metabolic age of red blood cells during cold storage," *Blood* 128: e43-50 (2016).
Paillous et al., "Mechanisms of photosensitized DNA cleavage," *J. Photochem. Photobiol. B: Biol.* 20:203-209 (1993).
Pallotta, et al., "Storing red blood cells with vitamin C and N-acetylcysteine prevents oxidative stress-related lesions: a metabolomics overview," *Blood Transfus* 12: 376-87 (2014).
Pallotta, et.al.,"Supplementation of anti-oxidants in leucofiltered erythrocyte concentrates: assessment of morphological changes through scanning electron microscopy," *Blood Transfus* 12: 421-4 (2014).
Peirce et al., "The Membrane Lung: Studies with a New High Permeability Co-Polymer Membrane," *Trans. Amer. Soc. Artif. Int. Organs* vol. XIV:220-226 (1968).
Pidcoke,et al "Tenyear analysis of Transfusion in Operation Iraqi Freedom and Operation Enduring Freedom: increased plasma and platelet use correlates with improved survival," *Journal of Trauma and Acute Care Surgery*;73: S445-S52 (2012).
Pelletier et al., "Pathogen inactivation techniques," *Best Practice & Research Clinical Haematology* 19(1):205-242 (2006).
Prudent, et al., "Oxygen in Red Blood Cell Concentrates Influence of Donor's Characteristics, Location and Blood Processing," *Vox Sang* 113: 116 (2018).
Reisz. et al., Red blood cells in hemorrhagic shock: a critical role for glutaminolysis in fueling alanine transamination in rats. *Blood Advances* 2017;1: 1296-305.
Reisz,et al Methylation of protein aspartates and deamidated asparagines as a function of blood bank storage and oxidative stress in human red blood cells, *Transfusion* 58: 2978-91 (2018).
Reisz, et al., "Metabolic Linkage and Correlations to Storage Capacity in Erythrocytes from Glucose 6-Phosphate Dehydrogenase-Deficient Donors," *Front Med* (Lausanne) 4: 248 (2017).
Reisz, et al., "Oxidative modifications of glyceraldehyde 3-phosphate dehydrogenase regulate metabolic reprogramming of stored red blood cells," *Blood* 128: e32-42 (2016).
Risbano, et al., "Effects of Aged Stored Autologous Red Blood Cells on Human Endothelial Function," *Am J Respir Crit Care Med* 192: 1223-33 (2015).
Rolfsson, et al., "Metabolomics comparison of red cells stored in four additive solutions reveals differences in citrate anticoagulant permeability and metabolism," *Vox Sang* (2017).
Scott, et al., "Effect of excess alpha-hemoglobin chains on cellular and membrane oxidation in model beta-thalassemic erythrocytes," *J Clin Invest* 91: 1706-12 (1993).
Seghatchian et al., "Pathogen-reduction systems for blood components: The current position and future trends," *Transfusion and Apheresis Science* 35:189-196 (2006).
Seok, et al., "Genomic responses in mouse models poorly mimic human inflammatory diseases," *Proceedings of the National Academy of Sciences* 110: 3507-12 (2013).
Shalev, et al., "Extremely high avidity association of Fe(III) with the sickle red cell membrane," *Blood* 88: 349-52 (1996).
Shapiro, "To filter blood or universal leukoreduction: what is the answer?," *Critical Care* 8(Suppl 2): S27-draftS30 (2004).
Sivertsen, et al., "Preparation of leucoreduced whole blood for Transfusion in austere environments; effects of forced filtration, storage agitation, and high temperatures on hemostatic function," *J Trauma Acute Care Surg* 84: S93-S103 (2018).

(56) References Cited

OTHER PUBLICATIONS

Snyder, et al., "In vitro and in vivo evaluation of a whole blood platelet-sparing leukoreduction filtration system," *Transfusion* 50: 2145-51 (2010).

Spinella, et al., "Prehospital hemostatic resuscitation to achieve zero preventable deaths after traumatic injury," *Curr Opin Hematol* (2017).

Spinella,et al., "Whole blood: back to the future," *Curr Opin Hematol* 23: 536-42 (2016).

Spinella et al., "Whole blood for hemostatic resuscitation of major bleeding," *Transfusion* 56:S190-S202 (2016).

Strandenes et al., "Emergency Whole-Blood Use in the Field: a Simplified Protocol for Collection and Transfusion," *SHOCK* 41(Suppl 1):76-83 (2014).

Strandenes et al., "Low Titer Group O Whole Blood in Emergency Situations," *SCHOCK* 41(Suppl 1): 70-75 (2014).

Sun, et al., "Purinergic control of red blood cell metabolism: novel strategies to improve red cell storage quality," *Blood Transfus* 15: 535-42 (2017).

Sun, et al., "Sphingosine-1-phosphate promotes erythrocyte glycolysis and oxygen release for adaptation to high-altitude hypoxia," *Nat Commun* 7: 12086 (2016).

Tannahill, et al., "Succinate is an inflammatory signal that induces IL-lbeta through HIF-1alpha" *Nature* 496: 238-42 (2013).

Teisseire, et al., "Induced low P50 in anesthetized rats: blood gas, circulatory and metabolic adjustments," *Respir Physiol* 58: 335-44 (1984).

Tolinski, "Getting the Most out of Polypropylene, Polythylene and TPO," *Additives for Polyolefins*, Second Edition 2015.

Tsai, et al., "Microvascular perfusion upon exchange Transfusion with stored red blood cells in normovolemic anemic conditions," *Transfusion* 44: 1626-34 (2004).

Tsantes, et al., "Redox imbalance, macrocytosis, and RBC homeostasis," *Antioxid Redox Signal* 8: 1205-16 (2006).

Valeri, et al., "Improved oxygen delivery to the myocardium during hypothermia by perfusion with 2,3 DPG-enriched red blood cells," *Am Thorac Surg* 30: 527-35 (1980).

Valeri. "Circulation and hemostatic effectiveness of platelets stored at 4 C or 22 C: studies in aspirin-treated normal volunteers," *Transfusion* 16: 20-3 (1976).

Valeri. "Hemostatic effectiveness of liquid-preserved and previously frozen human platelets," *N Engl J Med* 290: 353-8 (1974).

Van Buskirk, et al., "Comparison of Cytokine, Cell-free Hemoglobin, and Isoprostane Accumulations in Packed Red Blood Cells During Novel Anaerobic and Conventional Cold Storage," *Transfusion* 54S: SP53 (2014).

Van Buskirk, et al., "Comparison of microparticles production in packed red blood cells stored under anaerobic and conventional cold storage condition," *Vox Sang* 105 (S1): 150 (2007).

Van Buskirk, et al., "Evaluation of Select Red Blood Cell Biochemical and Coagulation Properties in Whole Blood Stored Using a Novel Anaerobic Storage Platform," *Transfusion* 56: 54A (2016).

Van Slyke, "An Apparatus for Determination of the Gases in Blood and Other Solutions," *Chemistry* 7:229-231 _1921.

Voigt, et al., "Effects of a restrictive Blood Transfusion protocol on acute pediatric burn care: Transfusion threshold in pediatric burns," *J Trauma Acute Care Surg* 85: 1048-54 (2018).

Williams, "Blood Transfusion on Cruise Ships; A 36 Month Review of Preliminary Data," *THOR Trauma Hemostasis & Oxygenation Research Network*, RDCR Symposium, Bergen (2013).

Williams, et al., "Transfusion of Anaerobically Stored Red Blood Cells Improves Recovery in Experimental Rat Hemorrhagic Shock Model," *Transfusion* 57: 33A (2017).

Williams, et al., "Transfusion of Anaerobically Stored Red Blood Cells Improves Recovery in Experimental Rat Hemorrhagic Shock Model," *Shock* Abstract (2019).

Wolfe, et al., "Molecular defect in the membrane skeleton of blood bank-stored red cells. Abnormal spectrin-protein 4.1-actin complex formation," *J Clin Invest* 78: 1681-6 (1986).

Wolfe. "Oxidative injuries to the red cell membrane during conventional blood preservation," *Semin Hematol* 26: 307-12 (1989).

Woodson. "Functional consequences of altered blood oxygen affinity," *Acta Biol Med Ger* 40: 733-6 (1981).

Yalcin, et al., "Increased hemoglobin 02 affinity protects during acute hypoxia," *Am J. Physiol Heart Circ Physiol* 303: H271-81 (2012).

Yhap,et al., "Decreased oxygen uptake with stored blood in the isolated hindlimb" *J Appl Physiol* 38: 882-5 (1975).

Yoshida, et al., "Oxygen content—uncontrolled and overlooked parameter associated with stored red cell concentrate: Unexpectedly wide distribution," *Vox Sang* 112: P-244 (2017) Abstract.

Yoshida, et al., "Enhancing uniformity and overall quality of red cell concentrate with anaerobic storage," *Blood Transfus* 15: 172-81 (2017).

Yoshida, et al., "Toward a comprehensive biochemical model of human erythrocyte: relationship between metabolic and osmotic state of the cell and the state of hemoglobin," *Prog Clin Biol Res* 319: 179-93; discussion 94-6 (1989).

Yoshida, et al., "Unexpected Variability of Hemoglobin Oxygen Saturation in Packed Red Blood Cells upon Donation Suggests Uncontrolled and Overlooked Parameter Associated with the Development of the Storage Lesion," *Transfusion* 57 (2017).

Yoshida, et al., "Red blood cell storage lesion: causes and potential clinical consequences" *Blood Transfus* 17: 27-52 (2019).

Yoshida, et al., "Reduction of Microparticle Generation During Anaerobic Storage of Red Blood Cells," *Transfusion* 52: 83A (2012).

Yuasa et al., "Improved extension of platelet storage in a polyolefin container with higher oxygen permeability," *British Journal of Hematology* 126:153-159 (2004).

Zaroulis, et al., "Lactic acidemia in baboons after Transfusion of red blood cells with improved oxygen transport function and exposure to severe arterial hypoxemia," *Transfusion* 19: 420-5 (1979).

Zavizion et al., "Inactivation of mycoplasma species in blood by INACTINE PEN110 process," *Transfusion* 44:286-293 (2004).

Zielinski et al., "Back to the future: The renaissance of whole-blood transfusions for massively hemorrhaging patients," *Surgery* 155(5) 883-886 (2014).

Zielinski, et al., "Prehospital Blood Transfusion programs: Capabilities and lessons learned," *J Trauma Acute Care Surg* 82: S70-s8 (2017).

Zingarelli, et al., "Part I. Minimum Quality Threshold in Preclinical Sepsis Studies (MQTiPSS) for study design and humane modeling endpoints," *Shock* 51: 10-22 (2019).

Zink, et al., "Noninvasive Evaluation of Active Lower Gastrointestinal Bleeding. Comparison Between Contrast-Enhanced MDCT and 99mTc-Labeled RBC Scintigraphy," *American Journal of Roentgenology* 191: 1107-14 (2008).

Zinkham, et al., "Carboxyhemoglobin levels in an unstable hemoglobin disorder (Hb Zurich): effect on phenotype expression," *Science* 209: 406-8 (1980).

Henschler et al., "Development of the S-303 Pathogen Inactivation Technology for Red Blood Cell Concentrates," *Transfusion Medicine and Hemotherapy* 38(1):33-42 (2011).

Bryant et al., "Pathogen Inactivation The Definitive Safeguard for the Blood Supply," *Arch Pathol Lab Med* 131:719-733 (2007).

Lozono et al., "Pathogen inactivation: coming of age," *Curr Opin Hematol* 20(6):540-545 (2013).

Prowse, C.V. et al., "Commercially available blood storage containers" Vox Sanguines. 106(1): 1-13 (2014).

Przepiorka et al. "Use of Irradiated Blood components: Practice Parameter," Am J Clin Pathol 106(1):6-11 (1996).

Van der Meer, P. and de Korte, D., "Platelet preservation: Agitation and containers" Transfusion and Apheresis Science. 44:297-304 (2011).

Wang, L. et al., "The contribution of oxidative stress to platelet senescence during storage" Transfusion. (2019).

Zolla et al., "Classic and alternative red blood cell storage strategies: seven years of'-omics' investigations," *Blood Transfus* 13:21-31 (2015).

\* cited by examiner

METHODS FOR THE STORAGE OF WHOLE BLOOD, AND COMPOSITIONS THEREOF

CROSS-REFERENCE TO RELATED APPLICATIONS

This application is a U.S. national phase application of International Application No. PCT/US216/033151 filed May 18, 2016, which claims benefit of U.S. Provisional Application No. 62/163,269 filed May 18, 2015, each of which are incorporated herein in their entireties.

FIELD OF THE INVENTION

The present disclosure relates to methods for improving the quality of whole blood useful for transfusion to patients. Anaerobic storage of whole blood provides for reduced levels of cytokines and improved levels of 2,3-diphosphoglycerate (2,3-DPG) and adenosine triphosphate (ATP). The improved blood compositions are useful for blood transfusions to cancer and trauma patients.

BACKGROUND OF THE INVENTION

When stored conventionally, stored blood undergoes a steady deterioration which is associated with various storage lesions including, among others, hemolysis, hemoglobin degradation, and reduced ATP and 2,3-DPG concentrations. When transfused into a patient, the effects of the steady deterioration during storage manifest, for example, as a reduction in the 24-hour in vivo recovery. Because of these and other medical sequelae of transfusion of stored blood, a variety of approaches have been developed to minimize the effects of storage on blood and to improve medical outcomes. See, for example, Zimring et al., "Established and theoretical factors to consider in assessing the red cell storage lesion" in *Blood*, 125:2185-90 (2015).

A number of approaches have been developed aimed at minimizing storage lesions and improving transfusion outcomes. One approach has been the development of additive solutions included during storage. Examples of this approach include U.S. Pat. No. 4,769,318 to Hamasaki et al. and U.S. Pat. No. 4,880,786 to Sasakawa et al. which are directed to additive solutions for blood preservation and activation. For example, Rejuvesol® (available from Citra Lab LLC, Braintree, Mass.) is added to blood after cold storage (i.e., 4° C.) just prior to transfusion or prior to freezing (i.e., at −80° C. with glycerol) for extended storage. U.S. Pat. No. 6,447,987 to Hess et al. is directed to additive solutions for the refrigerated storage of human red blood cells. An alternative approach is to freeze the blood and prevent the development of storage lesions. Storage of frozen blood is known in the art, but such frozen blood has limitations. U.S. Pat. No. 6,413,713 to Serebrennikov is directed to a method of storing blood at temperatures below 0° C. See Chaplin et al., "Blood Cells for Transfusion," *Blood*, 59: 1118-20 (1982), and Valeri et al., "The survival, function, and hemolysis of human RBCs stored at 4 degrees C. in additive solution (AS-1, AS-3, or AS-5) for 42 days and then biochemically modified, frozen, thawed, washed, and stored at 4 degrees C. in sodium chloride and glucose solution for 24 hours," *Transfusion*, 40:1341-5 (2000). Another approach relates to the containers for blood storage as provided by U.S. Pat. No. 4,837,047 to Sato et al.

One approach that has proven successful in improving blood quality and extending its utility is through the depletion of oxygen and storage under anaerobic conditions. U.S. Pat. No. 5,624,794 to Bitensky et al., U.S. Pat. No. 6,162,396 to Bitensky et al., and U.S. Pat. No. 5,476,764 to Bitensky are directed to the storage of red blood cells under oxygen-depleted conditions. U.S. Pat. No. 5,789,151 to Bitensky et al. is directed to blood storage additive solutions. Among the benefits of storing blood under oxygen depleted conditions are improved levels of ATP and 2,3-DPG, and reduced hemolysis. Storing blood under oxygen depleted conditions can also result in reduced microparticle levels, reductions in the loss of deformability, reduced lipid and protein oxidation and higher post transfusion survival when compared to blood stored under conventional conditions.

U.S. Pat. No. 6,162,396 to Bitensky et al. (the '396 patent) discloses anaerobic storage bags for blood storage that comprise an oxygen impermeable outer layer, a red blood cell (RBC) compatible inner layer that is permeable to oxygen having an oxygen scrubber placed between the inner and outer layers.

While the effects of oxygen depletion on packed red blood cells has been explored, the effects of oxygen depletion on whole blood has not been reported. In part, the lack of studies on the deoxygenation of whole blood may be due to the expectation that deleterious effects are expected when platelets are deprived of oxygen. More specifically, given the critical role of platelets in the coagulation process, there were concerns that decreases in platelet function would result in coagulopathies and negative consequences to clinical outcomes.

Storage of platelets has been extensively studied to identify the most favorable conditions including temperature, pH, $O_2$ and $CO_2$ concentrations. The result of this work is the conclusion that for stored platelets to persist in a recipient after transfusion, platelets require access to oxygen and storage at room temperature. Murphy and Gardner noted in 1975 that unwanted morphological changes were associated with reduced oxygen consumption. See, Murphy et al., "Platelet storage at 22 degrees C.: role of gas transport across plastic containers in maintenance of viability," *Blood* 46(2):209-218 (1975). The authors observed that increased access to oxygen allows for aerobic metabolism (oxidative phosphorylation) resulting in a reduced rate of lactate production. At low $PO_2$ levels lactic acid production is increased consistent with the Pasteur effect. Moroff et al. noted that continuous oxygen consumption is required to maintain the pH of stored platelets at pH 7. See Moroff et al., "Factors Influencing Changes in pH during Storage of Platelet Concentrates at 20-24° C.," *Vox Sanguinis* 42(1): 33-45 (1982). Specially tailored container systems allow permeability to carbon dioxide as well as oxygen to prevent a lethal drop in pH. As shown by Kakaiya et al., "Platelet preservation in large containers," *Vox Sanguinis* 46(2):111-118 (1984), maintaining platelet quality was the result of improved gas exchange conditions obtained with increased surface area available for gas exchange. The importance of maintaining oxygen levels during platelet storage led to the development of gas permeable containers and storage of platelets in oxygen enriched atmospheres. See U.S. Pat. No. 4,455,299, issued Jun. 19, 1984, to Grode. The importance of oxygen to the viability of stored platelets was reinforced by the observation that in an oxygen poor environment, the lactate levels increased 5-8 fold. See Kilkson et al., "Platelet metabolism during storage of platelet concentrates at 22 degrees C.," *Blood* 64(2):406-14 (1984). Wallvik et al., "Platelet Concentrates Stored at 22° C. Need Oxygen The Significance of Plastics in Platelet Preservation," *Vox Sanguinis* 45(4):303-311 (1983), reported that maintaining oxygen during the first five days of storage was critical for platelet preservation. Wallvik and co-workers also showed that the maximum platelet number that can be successfully stored for five days is predictable based on the determination of the oxygen diffusion capacity of the storage bag. See Wallvik et al, "The platelet storage capability of different plastic containers," *Vox Sanguinis* 58(1):40-4 (1990). By providing blood bags with adequate gas exchange properties, pH is maintained, the loss of ATP and the release of alpha-granular platelet Factor 4 (PF4) was prevented. Each of the foregoing references are hereby incorporated in their entireties.

These findings, among others, led to practice standardization ensuring the oxygenation of platelets during room temperature storage to maximize post-transfusion viability. When platelets are stored at refrigerated temperature, post-transfusion viability is lost, making such platelets unsuitable for prophylactic transfusion to oncology patients unable to produce their own platelets. On the other hand, platelets stored at refrigerated temperature maintain hemostatic functions when transfused to recipient. Thus, when giving platelets to patients suffering from traumatic bleeding, viability is less important than hemostatic activity. We demonstrate that anaerobic storage of refrigerated whole blood up to 3 weeks yields hemostatic activity consistent with refrigerated conventionally stored whole blood, clearly indicating that hemostatic activity of platelets is maintained with hypothermic storage, even though they are oxygen starved.

Though the depletion of oxygen in whole blood has been mentioned in the literature, the effects of anaerobic storage of whole blood has not been disclosed. As discussed above, it is well established that room temperature storage as well as oxygen is required during storage for long-term survival of platelets (PLT) (more than 24 hours) in recipients. However, for hemorrhagic trauma resuscitation, the long-term survival of PLT is not critical compared to its hemostatic potential. Recently, it became apparent that patients transfused with stored or fresh whole blood, as well as reconstituted whole blood (a mixture of plasma, red blood cells and platelets), have significantly lower post-trauma mortality. We recently discovered that cold storage enables anaerobic storage of PLT and also provides known advantages of anaerobically stored RBCs observed in packed red blood cells, in the whole blood. More specifically, while unexpectedly preserving the coagulability without introducing negative effects, deoxygenated whole blood provides for improved 2,3,-DPG levels. Over a storage period, the deformability of RBCs is maintained under deoxygenated conditions.

Oxidative damage during storage has been implicated as a major contributor to packed red blood cell (pRBC) membrane damage, as suggested by the accumulation of markers of lipid peroxidation, such as isoprostane. Increasing amounts of cytokines during storage duration may also play a role in storage lesion development with potential clinical implications for a negative transfusion outcome.

Certain patient populations are more susceptible to storage lesions than others. Among these more sensitive populations are, as non-limiting examples, trauma patients and cancer patients. Associated with the adverse clinical outcomes is the accumulation of biologic response modifiers (BRMs) that include cytokines that mediate inflammation, regulate cell growth, regulate angiogenesis and modulate t-helper cell function. Among these BRMs are interleukin 17 (IL-17), eotaxin (CCL11), basic FGF (bFGF), macrophage inflammatory protein 1a (MIP-1a), monocyte chemotactic protein 1 (MCP-1), platelet-derived growth factor (PDGF), tumor necrosis factor alpha (TNF-α), and vascular endothelial growth factor (VEGF). See Behrens et al., "Accumulation of biologic response modifiers during red blood cell cold storage," *Transfusion* 49 (*Suppl* 3):10A (2009). It has also been observed that cytokines accumulate during blood storage and these accumulated cytokines can be associated with negative outcomes when given perioperatively to cancer patients. See Benson et al., "Accumulation of Pro-Cancer Cytokines in the Plasma Fraction of Stored Packed Red Cells," *J Gastrointest Surg.* 16:460-468 (2012). There is a need for methods of blood storage that result in reduced levels of BRMs and cytokines, thereby improving patient outcomes.

Traumatic injury accounts for 30% of life years lost in the US, outpacing cancer (16% of life years) and heart disease (12%). Trauma is the leading cause of death among 1-46 year old patients. While death from hemorrhage often occurs within 24 hours of traumatic injury, early death (within 3-6 hours) due to massive hemorrhage is preventable with prompt and appropriate care.

Damage Control Resuscitation (DCR) protocols describe the concept of using balanced ratios of blood components. DCR is rapidly becoming a standard for arresting hemorrhage and reversing shock for rapidly hemorrhaging trauma victims. In the civilian setting, current blood banking practice does not include whole blood inventory and thus DCR is conducted with a sequential transfusion of separated components (RBC, plasma and platelets) such that blood is 'reconstituted' in the recipient. Earlier this year, a large scale randomized controlled trial (RCT), Pragmatic Randomized Optimal Platelet and Plasma Ratios (PROPPR), was completed comparing the efficacy of transfusing 'reconstituted blood' at a 1:1:1 unit ratio (plasma, platelets and RBC) vs. a 1:1:2 ratio to trauma patients with massive transfusion. In major trauma centers, massive transfusion kits combining pre-packaged blood products consisting of thawed fresh frozen plasma (FFP), platelets and RBC at 1:1:1 ratios are now readily available.

Recent studies suggest that whole blood may be superior when treating patients with severe bleeding to control hemorrhage and reverse shock for patients with life-threatening bleeding. The 2015 proceedings of the NHLBI State of the Science in Transfusion Medicine Symposium prioritized the study of whole blood for patients with severe bleeding. Likewise, the THOR Network, an international group focused on damage control resuscitation, has prioritized the comparison of the efficacy and safety of whole blood to components for hemorrhagic shock. Since modern blood banks do not routinely supply whole blood, over 80% of level 1 trauma centers surveyed attempt to mimic the hemostatic, shock-reversing properties needed in massive transfusion protocols with plasma, platelets and red blood cells units at ratios of 1:1:1 to 1:1:2 for both traumatic and non-traumatic life-threatening bleeding cases. Logistically providing all three blood components rapidly and safely is difficult, especially given the need to thaw plasma at centers where an inventory of thawed plasma is not immediately available. Recent data also indicates that storage of whole blood at 4° C. for up to 14 days maintains platelet function and global hemostatic efficacy that is superior to storage at 22° C.

In addition to a need for blood banks to provide whole blood for use in certain patient populations, the ability to conserve valuable blood resources is important. In particular, blood banks typically discard whole blood stocks after 2 weeks (even though FDA regulations allow for longer usable lifetimes), thus failing to take advantage of a valuable and often scarce resource. Such ability to maximize the value of the blood resource is particularly useful for small hospitals that serve as Level III and Level IV trauma centers where an oxygen depleted hemostatic whole blood product can be maintained under anaerobic conditions and then processed for packed red blood cells. The present specification provides for improved whole blood quality for use in trauma patients, and further provides for an additional source of packed red blood cells having improved properties and reduced storage lesions. The present specification overcomes concerns regarding the wasting of valuable O-negative RBCS (typically used for whole blood transfusions). Thus, the anaerobic RBCs may be obtained from the oxygen reduced whole blood and recycled into oxygen depleted RBC units suitable for storage for up to six weeks. As provided herein, deoxygenated packed red blood cells may be obtained from the unused oxygen depleted whole blood, used for transfusion, or stored for later use under anaerobic conditions.

SUMMARY OF THE INVENTION

The present disclosure provides for, and includes, a method for improving survival of a patient in need of multiple transfusions comprising providing stored red blood cells that have been oxygen reduced to a patient in need thereof receiving a medical procedure.

The present disclosure provides for, and includes, a method for improving survival of a cancer patient in need thereof following a perioperative blood transfusion comprising providing stored red blood cells that have been oxygen reduced to a cancer patient in need thereof receiving a surgical procedure.

The present disclosure provides for, and includes, a method for reducing pro-cancer cytokines in stored blood comprising depleting oxygen from the blood prior to storage comprising collecting blood in an anticoagulant solution, reducing the leukocytes from the collected blood, reducing the pre-storage oxygen saturation ($SO_2$) to 30% or less and a pre-storage partial pressure of carbon dioxide to less than 60 mmHg; and storing the oxygen and carbon dioxide reduced blood under anaerobic conditions.

The present disclosure provides for, and includes, a blood composition for transfusion to a trauma patient in need thereof comprising deoxygenated leukoreduced whole blood in an anticoagulant solution and having a pre-storage oxygen saturation ($SO_2$) of 20% or less and a pre-storage partial pressure of carbon dioxide of less than 60 mmHg wherein the deoxygenated leukoreduced whole blood has a 2,3-DPG level at 15 days that is greater than the initial 2,3-DPG level of the deoxygenated leukoreduced blood.

The present disclosure provides for, and includes, a method of reducing an inflammatory response in a patient receiving a blood transfusion comprising transfusing an oxygen depleted blood product to a patient in need thereof, wherein the oxygen depleted whole blood has reduced levels of inflammatory cytokines after storage under anaerobic conditions.

The present disclosure provides for, and includes, a method of reducing an immune response in a patient receiving a blood transfusion comprising transfusing an oxygen depleted blood product to a patient in need thereof, wherein the oxygen depleted blood product has reduced levels of a cytokine after storage under anaerobic conditions. In aspects according to the present disclosure, an immune response is an immune modulation or immune suppression. In other aspects, the immune response is an activation, including for example, inflammation.

The present disclosure provides for, and includes, a method for improving perfusion of oxygen in a patient in need thereof comprising transfusing an oxygen depleted blood product to a patient in need thereof, wherein the oxygen depleted blood product has higher RBC deformability compared to a conventionally stored blood product.

The present disclosure provides for, and includes, a method for managing a blood bank comprising maintaining an inventory of blood units comprising oxygen reduced whole blood and an anticoagulant, or oxygen reduced leukoreduced whole blood and an anticoagulant; providing one or more of the blood units from the inventory for treatment of a patient; and recycling blood units from the inventory to prepare component separated deoxygenated blood units. The present disclosure further provides for using recycled blood units to prepare reconstituted blood units for treatment of trauma patients requiring massive transfusions.

The present disclosure provides for, and includes, a method of providing a supply of blood products for transfusion medicine comprising depleting oxygen or oxygen and carbon dioxide from whole blood to prepare oxygen or oxygen and carbon dioxide reduced whole blood; and storing the oxygen or oxygen and carbon dioxide reduced whole blood for a time period and providing the stored blood to a patient in need thereof; or storing the oxygen or oxygen and carbon dioxide reduced whole blood for a time period, and preparing oxygen or oxygen and carbon dioxide reduced packed red blood cells.

BRIEF DESCRIPTION OF THE DRAWINGS

The present disclosure is disclosed with reference to the accompanying drawings, wherein:

FIG. 1C shows reduced levels of cell free hemoglobin compared to aerobically stored packed red blood cells. FIG. 1D shows reduced levels of isoprostane in anaerobically stored packed red blood cells. Dashed lines=aerobically stored blood; Solid lines=anaerobically stored blood.

FIG. 2A presents the levels 2,3-DPG. FIG. 2B presents the levels of ATP. FIG. 2C presents the pH. FIG. 2D presents the platelet count. FIG. 2E presents potassium levels. FIG. 2F presents the data of FIG. 2A re-plotted relative to the levels of 2,3-DPG at day 0 ($T_0$). FIG. 2G presents the data of FIG. 2B re-plotted relative to the levels of ATP at day 0 ($T_0$). Key: sample c68/80 is conventionally stored blood having an initial oxygen saturation of 68% and a partial pressure of $CO_2$ of 80 mmHg; sample c50/94 is conventionally stored blood having an initial oxygen saturation of 50% and a partial pressure of $CO_2$ of 94 mmHg; sample sc91/75 is conventionally stored blood having an initial oxygen saturation of 91% and a partial pressure of $CO_2$ of 75 mmHg; sample sc69/87 is conventionally stored blood having an initial oxygen saturation of 69% and a partial pressure of $CO_2$ of 87 mmHg; sample tc5/78 is oxygen depleted, anaerobically stored blood having an initial oxygen saturation of 5% and a partial pressure of $CO_2$ of 78 mmHg; sample tc7/64 is oxygen depleted, anaerobically stored blood having an initial oxygen saturation of 7% and a partial pressure of $CO_2$ of 64 mmHg; sample T5/28 is oxygen and carbon dioxide depleted, anaerobically stored blood having an initial oxygen saturation of 5% and a partial pressure of $CO_2$ of 28 mmHg; sample T4/26 is oxygen and carbon dioxide depleted, anaerobically stored blood having an initial oxygen saturation of 4% and a partial pressure of $CO_2$ of 26 mmHg.

FIG. 3A presents the levels 2,3-DPG. FIG. 3B presents the levels of ATP. FIG. 3C presents the data of FIG. 3A re-plotted relative to the levels of 2,3-DPG at day 0 ($T_0$). FIG. 3D presents the data of FIG. 3B re-plotted relative to the levels of ATP at day 0 ($T_0$). Key: sample c32/98 is conventionally stored blood having an initial oxygen saturation of 32% and a partial pressure of $CO_2$ of 98 mmHg; sample c56/86 is conventionally stored blood having an initial oxygen saturation of 56% and a partial pressure of $CO_2$ of 86 mmHg; sample sc59/95 is conventionally stored blood having an initial oxygen saturation of 59% and a partial pressure of $CO_2$ of 95 mmHg; sample sc82/84 is conventionally stored blood having an initial oxygen saturation of 82% and a partial pressure of $CO_2$ of 84 mmHg; sample tc7/80 is oxygen depleted, anaerobically stored blood having an initial oxygen saturation of 7% and a partial pressure of $CO_2$ of 80 mmHg; sample tc6/77 is oxygen depleted, anaerobically stored blood having an initial oxygen saturation of 6% and a partial pressure of $CO_2$ of 77 mmHg; sample T5/28 is oxygen and carbon dioxide depleted, anaerobically stored blood having an initial oxygen saturation of 5% and a partial pressure of $CO_2$ of 28 mmHg; sample T7/23 is oxygen and carbon dioxide depleted, anaerobically stored blood having an initial oxygen saturation of 7% and a partial pressure of $CO_2$ of 23 mmHg.

FIG. 4A presents the levels of ATP in OR-LRWB/CPDA1, OCR-LRWB/CPDA1 and conventionally stored LRWB/CPDA1. FIG. 4B presents the levels of 2,3-DPG in OR-LRWB/CPDA1, OCR-LRWB/CPDA1 and conventionally stored LRWB/CPDA1. FIG. 4C presents the percent hemolysis in OR-LRWB/CPDA1, OCR-LRWB/CPDA1 and conventionally stored LRWB/CPDA1. In graphs presented in FIGS. 4A to 4C, small dashed lines=OR-LRWB/CPDA1 stored blood, dashed lines=ORC-LRWB/CPDA1 stored blood, and solid lines=conventionally stored blood.

FIG. 5A presents activated Partial Thrombin Time in seconds (aPTT) in OCR-LRWB/CPDA1 and conventionally stored LRWB/CPDA1. FIG. 5B presents prothrombin time in seconds (PT) in OCR-LRWB/CPDA1 and conventionally stored LRWB/CPDA1. FIG. 5C presents the levels of Fibrinogen in OCR-LRWB/CPDA1 and conventionally stored LRWB/CPDA1. FIG. 5D presents the levels of D-dimer in OCR-LRWB/CPDA1 and conventionally stored LRWB/CPDA1. In graphs presenting plasma coagulation parameters, dashed lines=ORC-LRWB/CPDA1 stored blood, and solid lines=conventionally stored blood.

FIG. 6A presents levels of Factor V in OCR-LRWB/CPDA1 and conventionally stored LRWB/CPDA1. FIG. 6B presents levels of Factor VIII in OCR-LRWB/CPDA1 and conventionally stored LRWB/CPDA1. FIG. 6C presents Protein C activity in OCR-LRWB/CPDA1 and conventionally stored LRWB/CPDA1. FIG. 6D presents Protein S activity in OCR-LRWB/CPDA1 and conventionally stored LRWB/CPDA1. FIG. 6E presents levels of von Willebrand Factor (vWF) in OCR-LRWB/CPDA1 and conventionally stored LRWB/CPDA1. In graphs presenting plasma clotting factors, dashed lines=ORC-LRWB/CPDA1 stored blood, and solid lines=conventionally stored blood.

FIG. 7A presents the speed at which fibrin build up and crosslinking takes place (TEG Angle) in OCR-LRWB/CPDA1 and conventionally stored LRWB/CPDA1. FIG. 7B presents a comparison of blood kinetics (TEG K) in OCR-LRWB/CPDA1 and conventionally stored LRWB/CPDA1. FIG. 7C presents the maximum amplitude in OCR-LRWB/CPDA1 and conventionally stored LRWB/CPDA1. FIG. 7D presents the reaction time in OCR-LRWB/CPDA1 and conventionally stored LRWB/CPDA1. In graphs presenting thromboelastography (TEG) parameters, dashed lines=ORC-LRWB/CPDA1 stored blood, and solid lines=conventionally stored blood.

DETAILED DESCRIPTION

Figure 1A:
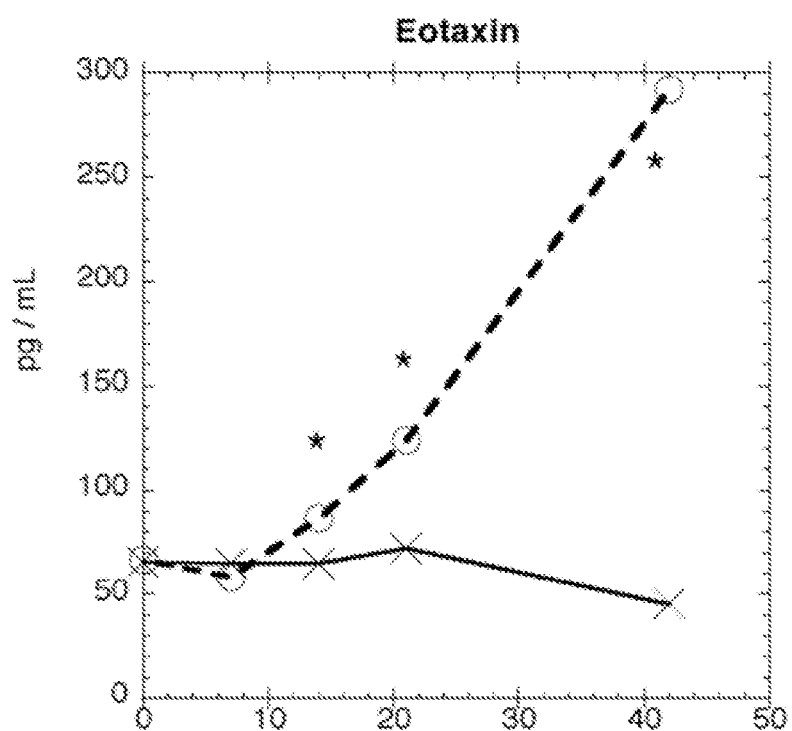
FIGS. 1A to 1D are graphs displaying the results of cytokine measurements showing reduced levels of eotaxin (1A) and RANTES (1B) in anaerobically stored packed red blood cells.

Unless defined otherwise, technical and scientific terms as used herein have the same meaning as commonly understood by one of ordinary skill in the art. One skilled in the art will recognize many methods can be used in the practice of the present disclosure. Indeed, the present disclosure is in no way limited to the methods and materials described. Any references cited herein are incorporated by reference in their entireties. For purposes of the present disclosure, the following terms are defined below.

As used herein, the term "patient" includes a person in need of a medical procedure receiving a blood product.

As used herein, the term "multiple transfusion" includes a patient receiving more than 195 units of blood. In another aspect, a multiple transfusion can include a patient receiving at least $1\times10^5$ mL of blood. In another aspect, multiple transfusion includes a patient receiving from 1 to $1\times10^5$ mL of blood. In another aspect, multiple transfusion includes a patient receiving from $1\times10^4$ to $1\times10^5$ mL of blood.

As used herein, the term "blood" refers to whole blood, leukoreduced RBCs, platelet reduced RBCs, and leukocyte and platelet reduced RBCs. The term blood further includes packed red blood cells, platelet reduced packed red blood cells, leukocyte reduced packed red blood cells (LRpRBC), and leukocyte and platelet reduced packed red blood cells. The temperature of blood can vary depending on the stage of the collection process, starting at the normal body temperature of 37° C. at the time and point of collection, but decreasing rapidly to about 30° C. as soon as the blood leaves the patient's body and further thereafter to room temperature in about 6 hours when untreated, and ultimately being refrigerated at between about 4° C. and 6° C.

As used herein, "blood product" includes separated platelets, plasma, or white blood cells.

As used herein, "recovered blood product" includes separated platelets, plasma, or white blood cells collected from a donor.

As used herein, "recovered blood" includes whole blood and red blood cells collected from a donor and previously stored under oxygen reduced conditions. In one aspect of the present disclosure, suitable blood for use in this method includes oxygen reduced leukoreduced packed red blood cells (OR-LRpRBC), oxygen reduced leukoreduced packed red blood cells with platelets (OR-LRpRBC+PLT), oxygen and carbon dioxide reduced leukoreduced packed red blood cells (OCR-LRpRBC), or oxygen and carbon dioxide reduced leukoreduced packed red blood cells with platelets (OCR-LRpRBC+PLT) obtained from oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), oxygen and carbon dioxide reduced leukoreduced whole blood with platelets (OCR-LRWB+PLT) after at least one week of storage. In another aspect, the suitable blood for use in this method is stored for up to 42 days. In another aspect, the suitable blood for use in this method is stored for up to 56 days. In another aspect, the suitable blood for use in this method is stored for up to 64 days.

As used herein, a method of obtaining "component separated blood products" includes obtaining recycled blood from a blood bank inventory and separating into platelets, plasma, and white blood cells. Suitable blood for use in this method comprises oxygen reduced whole blood having an anticoagulant and oxygen reduced leukoreduced whole blood having an anticoagulant. In an aspect of the present disclosure, a component separated oxygen reduced blood is stored for up to six weeks. In another aspect, a component separated oxygen reduced blood includes an additive solution. In certain aspects, the additive solution may be AS-1. In certain aspects, the additive solution is AS-3 (Nutricel®). In certain aspects, the additive solution is AS-5. In certain aspects, the additive solution is SAGM. In certain aspects, the additive solution is PAGG-SM. In certain aspects, the additive solution is PAGG-GM. In certain aspects, the additive solution is MAP. In certain aspects, the additive solution is SOLX. In certain aspects, the additive solution is ESOL. In certain aspects, the additive solution is EAS61. In certain aspects, the additive solution is OFAS1. In certain aspects, the additive solution is OFAS3. In certain aspects, the additive solution is a combination of AS-1, AS-3 (Nutricel®), AS-5, SAGM, PAGG-SM, PAGG-GM, MAP, SOLX, ESOL, EAS61, OFAS1, and OFAS3, alone or in combination.

As used herein, "reconstituted WB" includes providing platelets, RBC, and plasma in parallel to a patient during transfusion.

As used herein, "derived WB" includes oxygen reduced and oxygen and carbon dioxide reduced whole blood.

As used herein, "stored red blood cells" includes oxygen reduced or oxygen and carbon dioxide reduced red blood cells stored from 1 to 6° C. In an aspect, stored red blood cells include red blood cells (RBC) present in whole blood. In another aspect, stored red blood cells include RBC present in leukoreduced whole blood. In another aspect, stored red blood cells include red blood cells (RBC) present in leukoreduced RBC. In a further aspect, stored red blood cells include red blood cells (RBC) present in platelet reduced RBC. In yet another aspect, stored red blood cells include red blood cells (RBC) present in leukoreduced and platelet reduced RBC.

As used herein, "whole blood" includes white blood cells (WBCs), platelets suspended in plasma, and includes electrolytes, hormones, vitamins, antibodies, etc. In whole blood, white blood cells are normally present in the range of between 4.5 and $11.0 \times 10^9$ cells/L, and the normal RBC range at sea level is $4.6$-$6.2 \times 10^{12}$/L for men and $4.2$-$5.4 \times 10^{12}$/L for women. The normal hematocrit, or percent packed cell volume, is about 40-54% for men and about 38-47% for women. The platelet count is normally 150-$450 \times 10^9$/L for both men and women. Whole blood is collected from a blood donor, and is usually combined with an anticoagulant. Whole blood, when collected is initially at about 37° C. and rapidly cools to about 30° C. during and shortly after collection, but slowly cools to ambient temperature over about 6 hours. Whole blood may be processed according to methods of the present disclosure at collection, beginning at 30-37° C., or at room temperature (typically about 25° C.). As used herein, a "unit" of blood is about 450-500 ml including anticoagulant. Suitable anticoagulants include CPD, CPDA1, ACD, and ACD-A. As used herein, "time collected" (Tc) is the time at which blood is collected from the patient.

As used herein, "red blood cells" (RBCs), stored red blood cells, oxygen reduced red blood cells, and oxygen and carbon dioxide reduced red blood cells, include RBCs present in whole blood, leukoreduced RBCs, platelet reduced RBCs, leukocyte and platelet reduced RBCs, and packed red blood cells (pRBCs). Human red blood cells in vivo are in a dynamic state. The red blood cells contain hemoglobin, the iron-containing protein that carries oxygen throughout the body and gives red blood its color. The percentage of blood volume composed of red blood cells is called the hematocrit. As used herein, unless otherwise limited, RBCs also includes packed red blood cells (pRBCs). Packed red blood cells are prepared from whole blood using centrifugation techniques commonly known in the art. As used herein, unless otherwise indicated, the hematocrit of pRBCs is about 70%. As used herein, oxygen reduced RBC (OR-RBC) can include oxygen and carbon dioxide (OCR-) reduced RBC (OCR-RBC)

As used herein, "leukoreduced whole blood" (LRWB) includes whole blood having an anticoagulant that has been treated to remove white blood cells and platelets, usually by filtration or centrifugation. Leukoreduced whole blood has levels of white blood cells that are reduced by at least 5 logs.

As used herein, "oxygen reduced leukoreduced whole blood" (OR-LRWB) can include oxygen and carbon dioxide reduced leukoreduced whole blood (OCR-LRWB).

As used herein, "leukoreduced whole blood with platelets" (LRWB+PLT) includes oxygen reduced (OR-) whole blood having an anticoagulant and leukoreduced with a platelet-sparing filter. As used herein, oxygen reduced leukoreduced whole blood with platelets (OR-LRWB+PLT) can include oxygen and carbon dioxide reduced leukoreduced whole blood with platelets (OCR-LRWB+PLT).

As used herein, "leukoreduced packed red blood cells" (LRpRBC) includes packed red blood cells having oxygen reduced (OR-) whole blood having an anticoagulant that has been treated to remove white blood cells, usually by filtration or centrifugation. As used herein, oxygen reduced leukoreduced packed red blood cells (OR-LRpRBC) can include oxygen and carbon dioxide reduced leukoreduced packed red blood cells (OCR-LRpRBC).

As used herein, "leukoreduced packed red blood cells with platelets" (LRpRBC+PLT) includes packed red blood cells having platelets obtained from oxygen reduced whole blood having an anticoagulant that has been treated to remove white blood cells with a platelet-sparing filter. As used herein, oxygen reduced leukoreduced packed red blood cells with platelets (OR-LRpRBC+PLT) can include oxygen and carbon dioxide reduced leukoreduced packed red blood cells with platelets (OCR-LRpRBC+PLT).

In aspects of the present disclosure, the method and compositions may include adding an additive solution to the packed RBCs to form a suspension. A number of additive solutions are known in the art. In certain aspects, the additive solution may be selected from the group consisting of AS-1, AS-3 (Nutricel®), AS-5, SAGM, PAGG-SM, PAGG-GM, MAP, AS-7, ESOL-5, EAS61, OFAS1, and OFAS3, alone or in combination. Additive AS-1 is disclosed in Heaton et al., "Use of Adsol preservation solution for prolonged storage of low viscosity AS-1 red blood cells," *Br J Haematol.*, 57(3): 467-78 (1984). In a further aspect, the additive solution may have a pH of from 5.0 to 9.0. In another aspect, the additive may include an antioxidant. In some aspects according the present disclosure, the antioxidant may be quercetin, alpha-tocopherol, ascorbic acid, or enzyme inhibitors for oxidases.

As used herein the term "about" refers to ±10%.

The terms "comprises," "comprising," "includes," "including," "having," and their conjugates mean "including but not limited to."

The term "consisting of" means "including and limited to."

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular forms "a," "an," and "the" include plural references unless the context clearly dictates otherwise. For example, the term "a compound" or "at least one compound" may include a plurality of compounds, including mixtures thereof.

Throughout this application, various aspects of this disclosure may be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as "from 1 to 6" should be considered to have specifically disclosed subranges such as "from 1 to 3," "from 1 to 4," "from 1 to 5," "from 2 to 4," "from 2 to 6," "from 3 to 6," etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques, and procedures for accomplishing a given task including, but not limited to, those manners, means, techniques, and procedures either known to or readily developed from known manners, means, techniques, and procedures by practitioners of the chemical, pharmacological, biological, biochemical, and medical arts.

As used herein, the term "equivalent" means that the measured values of oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT), when compared the measured values of otherwise equivalently treated conventionally stored blood, are within 1 standard deviation of each other with a sample size of at least 5 for each compared measured condition.

As used herein, the term "greater" or "increased" means that the measured values of oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT), when compared OR-WB, when compared to the measured values of otherwise equivalently treated conventionally stored blood, are at least 1 standard deviation greater, with a sample size of at least 5 for each compared measured condition.

As used herein, the term "decreased" or "less" means that the measured values of oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT), when comparedOR-WB, when compared to the measured values of otherwise equivalently treated conventionally stored blood, are at least 1 standard deviation lower, with a sample size of at least 5 for each compared measured condition.

As used herein, the terms "conventionally stored," "conventional storage," and "conventional conditions" include whole blood, leukoreduced RBCs, platelet reduced RBCs, leukocyte and platelet reduced RBCs, packed red blood cells, platelet reduced packed red blood cells, leukocyte reduced packed red blood cells (LRpRBC), and leukocyte and platelet reduced packed red blood cells stored in oxygen and carbon dioxide permeable container at 1 to 6° C. without gas reduction steps prior to storage. In an aspect of the present disclosure, both oxygen and carbon dioxide increase to ambient levels over time in conventionally stored whole blood, leukoreduced RBCs, platelet reduced RBCs, leukocyte and platelet reduced RBCs, packed red blood cells, platelet reduced packed red blood cells, leukocyte reduced packed red blood cells (LRpRBC), and leukocyte and platelet reduced packed red blood cells, due to oxygen and carbon dioxide container permeability. While not traditionally considered conventional, for the purposes of the present disclosure, conventional storage can include storage at temperatures above 6° C. Also, while not traditionally considered conventional, for the purposes of the present disclosure, conventional storage can include storage at freezing temperatures.

The present disclosure provides for, and includes, methods to provide desirable characteristics to blood products for transfusion. It has been discovered that depletion of oxygen from packed red blood cells results in reduced accumulations of unbound cytokine, particularly RANTES (C-C motif chemokine ligand 5, CCL5) and eotaxin (C-C motif chemokine ligand 11, CCL11), as well as cell-free hemoglobin, and 8-isoprostane $F_{2\alpha}$. Not to be limited by theory, it is thought that RANTES and eotaxin are normally sequestered by binding to the DARC (atypical chemokine receptor 1, ACKR1) and oxidative stress damages DARC and releases the bound chemokines. Thus, while overall content of the chemokines does not change, the effective concentration (e.g., freely diffusible and unbound) increases and is then available to affect a transfused patient. As will be understood, the presence of these active chemokines (acting in a dose dependent manner) can be detrimental to trauma and other patients receiving two or more transfusions. These findings demonstrate an unexpected benefit of anaerobically stored blood, in addition to the desirable efficient oxygen delivery associated with elevated 2,3-DPG values, and provides a potential reduction in some of the components of the storage lesion resultant from pRBC oxidative damage during storage. These cytokines are known to be negatively associated with patient outcome in some patient populations. Accordingly, the discovery that unbound cytokine accumulation can be reduced provides for improved methods of treating patients susceptible to cytokines.

The present disclosure provides for, and includes, improving the survival of a patient in need of multiple transfusions by providing stored red blood cells that have been oxygen reduced (OR-stored RBCs) to a patient in need thereof receiving a medical procedure. Not to be limited by theory, it is believed that increased levels of cytokines have adverse effects on recipient patients that increases morbidity. In an aspect, the stored red blood cells are oxygen reduced (OR). In a further aspect, the stored red blood cells are both oxygen and carbon dioxide reduced (OCR). As shown in the examples, in OCR samples, the levels of ATP are decreased and maintained at lower levels for at least 15 days, while in OR samples, the levels of ATP are increased compared to conventionally stored samples (see FIG. 4A). As shown in the examples, in OCR samples, the levels of 2,3-DPG are increased and maintained at high levels for at least 15 days, while in OR samples, 2,3-DPG levels are increased over conventional storing but not as high as 2,3-DPG levels of OCR samples (see FIG. 4B). Further, as shown in the examples, hemolysis is equivalent in OR, OCR, and conventionally stored samples.

In an aspect of the present disclosure, cytokines comprise monocyte chemotactic protein-1 (MCP-1). In another aspect, cytokines comprise regulated on activation normal T cell expressed and secreted (RANTES). In another aspect, cytokines comprise angiogenin. In another aspect of the present disclosure, cytokines comprise tumor necrosis factor-alpha (TNF-α). In another aspect, cytokines comprise epidermal growth factor (EGF). In a further aspect, cytokines comprise platelet-derived growth factor (PDGF).

In an aspect of the present disclosure, the level of the factor RANTES is less than 500 pg/ml after 21 days under OR conditions. In another aspect, the level of the factor RANTES is less than 400 pg/ml after 21 days under OR conditions. In another aspect, the level of the factor RANTES is less than 300 pg/ml after 21 days under OR conditions. In another aspect, the level of the factor RANTES is more than 100 pg/ml after 21 days under OR conditions. In a further aspect, the level of the factor RANTES is from 0 to 300 pg/ml after 21 days under OR conditions.

In an aspect of the present disclosure, the level of the factor eotaxin is less than 150 pg/ml after 21 days under OR conditions. In another aspect, the level of the factor eotaxin is less than 100 pg/ml after 21 days under OR conditions. In another aspect, the level of the factor eotaxin is from 0 to 100 pg/ml after 21 days under OR conditions. In another aspect, the level of the factor eotaxin is preferably 100 pg/ml after 21 days under OR conditions. In another aspect, the level of the factor eotaxin is more than 100 pg/ml after 21 days under OR conditions. In a further aspect, the level of the factor eotaxin is from 0 to 300 pg/ml after 21 days under OR conditions.

In aspects according to the present disclosure, the OR-stored RBCs are selected from the group consisting of oxygen reduced leukoreduced whole blood (OR-LRWB), oxygen reduced leukoreduced whole blood with platelets (OR-LRWB+PLT), oxygen reduced leukoreduced packed red blood cells (OR-LRpRBC), oxygen reduced leukoreduced packed red blood cells with platelets (OR-LRpRBC+PLT), oxygen and carbon dioxide reduced leukoreduced whole blood (OCR-LRWB), oxygen and carbon dioxide reduced leukoreduced whole blood with platelets (OCR-LRWB+PLT), oxygen and carbon dioxide reduced leukoreduced packed red blood cells (OCR-LRpRBC), oxygen and carbon dioxide reduced leukoreduced packed red blood cells with platelets (OCR-LRpRBC+PLT), and combinations thereof. In other aspects, wherein said OR-stored RBCs comprise oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT).

In an aspect, a patient in need of multiple transfusions is a trauma patient. In another aspect, a patient in need of multiple transfusions is a transplant patient. In another aspect, a patient in need of multiple transfusions is a cardiac surgery patient. In another aspect, a patient in need of multiple transfusions is an obstetrics patient. In another aspect, a patient in need of multiple transfusions is a gastrointestinal (GI) surgery patient. In a further aspect, a patient is an orthopedic surgery patient.

In an aspect, a patient in need of multiple transfusions is a trauma patient. In another aspect, a patient in need of multiple transfusions is a hemorrhagic trauma patient. In a further aspect, a patient in need of multiple transfusions is a blunt trauma patient.

In an aspect, the reduction of cytokines in oxygen reduced stored packed red blood cells provides for improved treatment of cancer patients in need of blood transfusions. It is known in the art that cytokines are associated with negative patient outcome for patients receiving perioperative blood transfusions for surgical treatments of cancer patients. In an aspect, the oxygen depleted, cytokine reduced blood products are provided to a cancer patient prior to undergoing surgery. In another aspect, the oxygen depleted, cytokine reduced blood products are provided to a cancer patient during surgery. In another aspect, the oxygen depleted, cytokine reduced blood products are provided to a cancer patient following surgery.

In aspects according to the present disclosure, the oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) has higher levels of 2,3-DPG compared to conventionally stored leukoreduced whole blood (WB) and provides for improved oxygen delivery. Under anaerobic conditions, 2,3-DPG levels can be maintained in whole blood for up to 4 weeks. In an aspect, the 2,3-DPG levels are maintained above 50% of physiologic levels for up to four weeks. In aspects according to the present disclosure, improved 2,3-DPG levels are maintained for at 2 weeks. In other aspects, 2,3-DPG levels are maintained for three weeks. In an aspect, the 2,3-DPG level of the oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) is at least 80% or higher than the 2,3-DPG level of the blood at day zero. In another aspect, the 2,3-DPG level of the oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) is at least 5 to 20 DPG μmol/gHb.

Also provided for and included in the present disclosure is oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) that have depleted whole blood (OR-WB) that has reduced levels of biological response modifiers (BRMs) relative to conventionally stored whole blood. In certain aspects, the BRM present in oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) is about half the level of conventionally stored blood after 21 days. In an aspect, the oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) has levels of cytokines that are relatively unchanged after 10 days in storage under anaerobic conditions. In another aspect, the cytokine level is relatively unchanged after 30 days of storage. In another aspect, the cytokine level is relatively unchanged after 40 days of storage. As used herein, "relatively unchanged" means that the concentration of cytokine, normalized to hemoglobin levels is within 1 standard deviation of the initial normalized concentration of cytokine.

In certain aspects, the oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) has reduced levels of the cytokine eotaxin compared to conventionally stored whole blood. In an aspect, the level of eotaxin in oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) is about half the level of eotaxin present in conventionally stored blood after 21 days, normalized to the hemoglobin concentration. In an aspect, the level of eotaxin in oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) is about 25% or less of the level of eotaxin present in conventionally stored blood after 40 days.

In certain aspects, the oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) has reduced levels of the cytokine RANTES (regulated on activation, normal T cell expressed and secreted) compared to conventionally stored whole blood. In an aspect, the level of RANTES in oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) is about half the level of RANTES present in conventionally stored blood after 21 days, normalized to the hemoglobin concentration. In an aspect, the level of RANTES in oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) is about 25% or less of the level of RANTES present in conventionally stored blood after 40 days.

In certain aspects, the oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) has reduced levels of monocyte chemotactic protein-1 (MCP-1) compared to conventionally stored whole blood. In an aspect, the level of MCP-1 in oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) is about half the level of MCP-1 present in conventionally stored blood after 21 days, normalized to the hemoglobin concentration. In an aspect, the level of MCP-1 in oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) is about 25% or less of the level of MCP-1 present in conventionally stored blood after 40 days.

In certain aspects, the oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) has reduced levels of angiogenin compared to conventionally stored whole blood. In an aspect, the level of angiogenin in oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) is about half the level of angiogenin present in conventionally stored blood after 21 days, normalized to the hemoglobin concentration. In an aspect, the level of angiogenin in oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) is about 25% or less of the level of angiogenin present in conventionally stored blood after 40 days.

In certain aspects, the oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) has reduced levels of tumor necrosis factor-alpha (TNF-α) compared to conventionally stored whole blood. In an aspect, the level of TNF-α in oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) is about half the level of TNF-α present in conventionally stored blood after 21 days, normalized to the hemoglobin concentration. In an aspect, the level of TNF-α in oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) is about 25% or less of the level of TNF-α present in conventionally stored blood after 40 days.

In certain aspects, the oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) has reduced levels of epidermal growth factor (EGF) compared to conventionally stored whole blood. In an aspect, the level of EGF in oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) is about half the level of EGF present in conventionally stored blood after 21 days, normalized to the hemoglobin concentration. In an aspect, the level of EGF in oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) is about 25% or less of the level of EGF present in conventionally stored blood after 40 days.

In certain aspects, the oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) has reduced levels of soluble CD40 ligand (sCD40L) compared to conventionally stored whole blood. In an aspect, the level of sCD40L in oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) is about half the level of sCD40L present in conventionally stored blood after 21 days, normalized to the hemoglobin concentration. In an aspect, the level of sCD40L in oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) is about 25% or less of the level of sCD40L present in conventionally stored blood after 40 days.

In certain aspects, the oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) has reduced levels of platelet-derived growth factor (PDGF) compared to conventionally stored whole blood. In an aspect, the level of PDGF in oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) is about half the level of PDGF present in conventionally stored blood after 21 days, normalized to the hemoglobin concentration. In an aspect, the level of PDGF in oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) is about 25% or less of the level of PDGF present in conventionally stored blood after 40 days.

The present disclosure provides for, and includes, oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) that provides a reduced inflammatory response when transfused into a patient compared to conventionally stored oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT).

The present disclosure provides for, and includes, oxygen reduced leukoreduced whole blood (OR-LRWB) that provides blood products having higher RBC deformability compared to conventionally stored blood products. In certain aspects, the blood product is a whole blood product. In another aspect, the blood product is leukoreduced whole blood. In another aspect, the blood product is leukoreduced and platelet reduced whole blood. In a further aspect, the blood product is leukoreduced packed red blood cells or leuko- and platelet-reduced packed red blood cells.

The present disclosure provides for, and includes, oxygen reduced leukoreduced whole blood (OR-LRWB) that has coagulation parameters that are at least 75% of the coagulation parameter of conventionally stored whole blood as measured by thromboelastography (TEG). In an aspect, the TEG coagulation parameter of the oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) is equivalent to conventionally stored blood. In yet another aspect, oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) has a TEG coagulation parameter that is greater than the TEG coagulation parameter of conventionally stored blood. In an aspect, the TEG Angle is more than 40°. In another aspect, the TEG kinetics (K) is less than 5 mins. In another aspect the TEG K is between 1 to 5 mins. In another aspect, the TEG maximum amplitude (TEG MA) is more than 50 mm. In another aspect, the TEG maximum amplitude (TEG MA) is less than 70 mm. In another aspect, the TEG maximum amplitude (TEG MA) is between 30 to 65 mm. In another aspect, the TEG reaction time (TEG R) is less than 10 mins. In another aspect, the TEG reaction time (TEG R) is less than 8 mins. In another aspect, the TEG reaction time (TEG R) is at least 3 mins. In a further aspect, the TEG reaction time (TEG R) is between 4 to 8 mins.

The present disclosure provides for, and includes, oxygen reduced leukoreduced whole blood (OR-LRWB) that has coagulation parameters that are at least 75% of the coagulation parameter of conventionally stored whole blood as measured by prothrombin time (PT). In an aspect, the PT of the oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) is equivalent to conventionally stored blood. In yet another aspect, oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) has a PT that is greater than the PT of conventionally stored blood. In a further aspect, oxygen reduced leukoreduced whole blood (OR-LRWB) has a PT of less than 15 seconds. In another aspect, oxygen reduced leukoreduced whole blood (OR-LRWB) has a PT of more than 5 seconds. In another aspect, oxygen reduced leukoreduced whole blood (OR-LRWB) or has a PT of 10 to 15 seconds.

The present disclosure provides for, and includes, oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) that has coagulation parameters that are at least 75% of the coagulation parameter of conventionally stored whole blood as measured by partial thromboplastin time (PTT). In an aspect, the PTT of the oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) is equivalent to conventionally stored blood. In yet another aspect, oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) has a PTT that is greater than the PTT of conventionally stored blood. In a further aspect, oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) has a PTT that is greater than 25 seconds. In another aspect, oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) has a PTT that is less than 40 seconds. In another aspect, oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) has a PTT that is between 32 to 42 seconds.

The present disclosure provides for, and includes, oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) that have whole blood (OR-WB) that has coagulation parameters that are at least 75% of the coagulation parameter of conventionally stored whole blood as measured by the level of fibrinogen activity. In an aspect, the fibrinogen activity of the oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) is equivalent to conventionally stored blood. In yet another aspect, oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) has a fibrinogen activity that is greater than the fibrinogen activity of conventionally stored blood. In a further aspect, oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) has a fibrinogen level that is at least 200 mg/ml. In another aspect, oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) has a fibrinogen level that is at most 400 mg/ml. In another aspect, oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) has a fibrinogen level that is from 250 to 350 mg/ml. In another aspect, oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) has a fibrinogen level that is from 250 to 300 mg/ml.

The present disclosure provides for, and includes, oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) that have whole blood (OR-WB) that has coagulation parameters that are at least 75% of the coagulation parameter of conventionally stored whole blood as measured by D-dimer analysis. In an aspect, the D-dimer value of the oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) is equivalent to conventionally stored blood. In yet another aspect, oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) has a D-dimer value that is greater than the D-dimer value of conventionally stored blood.

The present disclosure provides for, and includes, oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) that have whole blood (OR-WB) that has coagulation parameters that are at least 75% of the coagulation parameter of conventionally stored whole blood as measured by a thrombin generation assay. In an aspect, the thrombin generation value of the oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) is equivalent to conventionally stored blood. In yet another aspect, oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) has a thrombin generation value that is greater than the thrombin generation value of conventionally stored blood.

The present disclosure provides for, and includes, oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) that has platelet function parameters that are at least 75% of the platelet function parameters of conventionally stored whole blood as measured by a platelet aggregometer. In an aspect, the platelet function parameters of the oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) are equivalent to conventionally stored blood. In yet another aspect, oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) has platelet function parameters that are greater than the platelet function parameters of conventionally stored blood.

The present disclosure provides for, and includes, oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) that has levels of clotting factor that are at least 75% of the levels of clotting factor in conventionally stored blood. In an aspect, the level of clotting factors is equivalent to that of conventionally stored blood. In yet other aspects, oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) has a platelet function parameter that is greater than the platelet function parameter of conventionally stored blood. Not to be limited by theory, it is thought that oxidative degradation of clotting factors is prevented or reduced in oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) and provides for higher levels of clotting factor activity. Methods to evaluate the effect of treatments on coagulability are known in the art, for example as described by Pidcoke et al., "Primary hemostatic capacity of whole blood: a comprehensive analysis of pathogen reduction and refrigeration effects over time," *Transfusion* 53:137S-149S (2013).

The present disclosure provides for, and includes, oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) that has a level of Factor V that has a specific activity that is at least 75% of the level of Factor V activity present in conventionally stored blood. In an aspect, the specific activity of Factor V is equivalent to that of conventionally stored blood. In yet other aspects, oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) has a specific activity of Factor V that is greater than the platelet function parameter of conventionally stored blood. Methods of measuring the specific activity of Factor V are known in the art.

The present disclosure provides for, and includes, oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) that has a level of Factor V that has a specific activity that is at least 75% of the level of Factor VIII activity present in conventionally stored blood. In an aspect, the specific activity of Factor VIII is equivalent to that of conventionally stored blood. In yet other aspects, oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) has a specific activity of Factor VIII that is greater than the platelet function parameter of conventionally stored blood. Methods of measuring the specific activity of Factor VIII are known in the art. In one aspect, oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) has a specific activity of Factor V that is less than 40% after 21 days of storage.

The present disclosure provides for, and includes, oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) that has a level of antithrombin (AT) that has a specific activity that is at least 75% of the level of AT activity present in conventionally stored blood. In an aspect, the specific activity of AT is equivalent to that of conventionally stored blood. In yet other aspects, oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) has a specific activity of AT that is greater than the platelet function parameter of conventionally stored blood. Methods of measuring the specific activity of AT are known in the art.

The present disclosure provides for, and includes, oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) that has a level of Factor XIV (autoprothrombin IIA or Protein C) that has a specific activity that is at least 75% of the level of Factor XIV activity present in conventionally stored blood. In an aspect, the specific activity of Factor XIV is equivalent to that of conventionally stored blood. In yet other aspects, oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) has a specific activity of Factor XIV that is greater than the platelet function parameter of conventionally stored blood. Methods of measuring the specific activity of Factor XIV are known in the art.

The present disclosure provides for, and includes, oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) that has a level of Von Willebrand factor (vWF) that has a specific activity that is at least 75% of the level of vWF activity present in conventionally stored blood. In an aspect, the specific activity of vWF is equivalent to that of conventionally stored blood. In yet other aspects, oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) has a specific activity of vWF that is greater than the platelet function parameter of conventionally stored blood. In another aspect, oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) has a specific activity of vWF that is less than the platelet function parameter of conventionally stored blood. Methods of measuring the specific activity of vWF are known in the art.

The present disclosure provides for, and includes, methods to extend the stored shelf life of whole blood from the current 2 weeks to 3 weeks and beyond. The oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) of the present disclosure provides for patient outcomes at three weeks that are equivalent to patient outcome provided by whole blood that has been stored for two weeks under conventional conditions.

As provided herein, oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) has decreased side effects for transfusion recipients as compared to conventionally stored blood. In an aspect, oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) has a decreased inflammatory response after two weeks storage as compared to conventionally stored blood. In other aspects, the inflammatory response is reduced relative to conventionally stored blood after three weeks. In an aspect, the oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) can be stored for more than three weeks and retain the levels of inflammatory response as compared to conventionally stored blood after two weeks.

As provided herein, oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) has decreased side effects for transfusion recipients as compared to conventionally stored blood. In an aspect, oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) has a decreased immune modulation after two weeks storage as compared to conventionally stored blood. In other aspects, the immune modulation is reduced relative to conventionally stored blood after three weeks. In an aspect, the oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) can be stored for more than three weeks and retain the levels of immune modulation as compared to conventionally stored blood after two weeks.

The methods and whole blood products of the present disclosure provide improved patient outcomes when transfused. In particular, oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) provides for improved survival in cancer patients when provided in perioperative transfusions. In a certain aspect, the oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) provides for reduced mortality and improved survival when provided perioperatively to pancreatic cancer patients. Not to be limited by theory, the reduced mortality is the result of the combination of reduced levels of cytokines and improved oxygen transport and delivery that results from increased levels of 2,3-DPG and ATP.

In an aspect, the blood for transfusion to a cancer patient in need thereof has a reduced level of the cytokine regulated on activation, normal T cell expressed and secreted (RANTES). In an aspect, the RANTES level is equivalent to the level of RANTES present at the beginning of storage. In another aspect, the RANTES level of oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) is less than the level of RANTES present in conventionally stored blood. In an aspect, the level of RANTES is less than the level of RANTES present in conventionally stored blood throughout the storage period. In other aspects, RANTES does not increase during storage.

In an aspect, the blood for transfusion to a cancer patient in need thereof has a reduced level of a CC chemokine that is an eosinophil chemotactic protein, eotaxin. In an aspect, the eotaxin having a reduced level in oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) is eotaxin-1, also known as C-C motif chemokine 11. In an aspect the eotaxin level is equivalent to the level of eotaxin present at the beginning of storage. In another aspect, the eotaxin level of oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) is less than the level of eotaxin present in conventionally stored blood. In an aspect, the level of eotaxin is less than the level of eotaxin present in conventionally stored blood throughout the storage period. In other aspects, eotaxin does not increase during storage.

The methods and whole blood products of the present disclosure provide for reduced multiple organ dysfunction syndrome and improved patient outcomes when transfused. In particular, oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) provides for reduced multiple organ dysfunction syndrome in trauma patients when provided in perioperative transfusions. In a certain aspect, the oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT) provides for reduced multiple organ dysfunction syndrome in trauma patients when provided during emergency treatment.

The present disclosure provides for, and includes, a method of preparing oxygen reduced leukoreduced whole blood comprising obtaining a unit of whole blood comprising an anticoagulant, filtering the whole blood to produce leukoreduced whole blood, depleting the leukoreduced whole blood of oxygen, and storing the oxygen reduced leukoreduced whole blood under anaerobic conditions.

The present disclosure provides for, and includes, a method of preparing oxygen reduced leukoreduced whole blood that has a pre-storage oxygen saturation of ($SO_2$) of 30% or less. Whole blood obtained from a donor using venipuncture has an oxygen saturation ranging from about 30% to about 70% saturated oxygen ($SO_2$). In certain aspects, the $SO_2$ is reduced to 25% or less. In certain aspects, the $SO_2$ is reduced to 20% or less. In certain aspects, the $SO_2$ is reduced to 15% or less. In other aspects, the $SO_2$ is reduced to 10% or less. In yet other aspects, the $SO_2$ is reduced to 5% or less.

Also provided for and included in the present disclosure are compositions and methods to prepare compositions of oxygen reduced and carbon dioxide reduced leukoreduced whole blood. In certain aspects, the $SO_2$ value is 20% or less and the partial pressure of carbon dioxide is less than 60 mmHg. In other aspects, the partial pressure of carbon dioxide is between 10 and 60 mmHg. In another aspect, the partial pressure of carbon dioxide is between 20 and 40 mmHg. Also included are whole blood compositions and methods that provide for an $SO_2$ of 15% or less and a partial pressure of carbon dioxide of between 10 and 60 mmHg. In another aspect, the methods and compositions include whole blood products having an $SO_2$ of 15% or less and a partial pressure of carbon dioxide of between 20 and 40 mmHg. In yet another aspect, the blood compositions and methods of the present disclosure have an $SO_2$ of 10% or less and a partial pressure of carbon dioxide of between 10 and 60 mmHg. In other aspects, the blood compositions and methods of the present disclosure have an $SO_2$ of 10% or less and a partial pressure of carbon dioxide of between 20 and 40 mmHg. In yet further aspects, the blood compositions and methods of the present disclosure have an $SO_2$ of 5% or less and a partial pressure of carbon dioxide of between 10 and 60 mmHg. In other aspects, the blood compositions and methods of the present disclosure have an $SO_2$ of 5% or less and a partial pressure of carbon dioxide of between 20 and 40 mmHg.

Also provided for and included in the present disclosure, are compositions and methods to prepare compositions of oxygen reduced and carbon dioxide reduced leukoreduced whole blood. In certain aspects, the $SO_2$ value is 20% or less and the partial pressure of carbon dioxide is between 1 and 60 mmHg. In other aspects, the partial pressure of carbon dioxide is between 10 and 60 mmHg. In another aspect, the partial pressure of carbon dioxide is between 20 and 40 mmHg or 1 and 20 mmHg. Also included are whole blood compositions and methods that provide for an $SO_2$ of 15% or less and a partial pressure of carbon dioxide of between 10 and 60 mmHg. In certain aspects, the $SO_2$ value is 15% or less and the partial pressure of carbon dioxide is between 1 and 60 mmHg. In another aspect, the methods and compositions include whole blood products having an $SO_2$ of 15% or less and a partial pressure of carbon dioxide of between 20 and 40 mmHg or 1 and 20 mmHg. In yet another aspect, the blood compositions and methods of the present disclosure have an $SO_2$ of 10% or less and a partial pressure of carbon dioxide of between 1 and 60 mmHg or 10 and 60 mmHg. In other aspects, the blood compositions and methods of the present disclosure have an $SO_2$ of 10% or less and a partial pressure of carbon dioxide of between 20 and 40 mmHg or 1 and 20 mmHg. In yet further aspects, the blood compositions and methods of the present disclosure have an $SO_2$ of 5% or less and a partial pressure of carbon dioxide of between 1 and 60 mmHg or 10 and 60 mmHg. In other aspects, the blood compositions and methods of the present disclosure have an $SO_2$ of 5% or less and a partial pressure of carbon dioxide of between 20 and 40 mmHg or 1 and 20 mmHg.

Figure 2A:
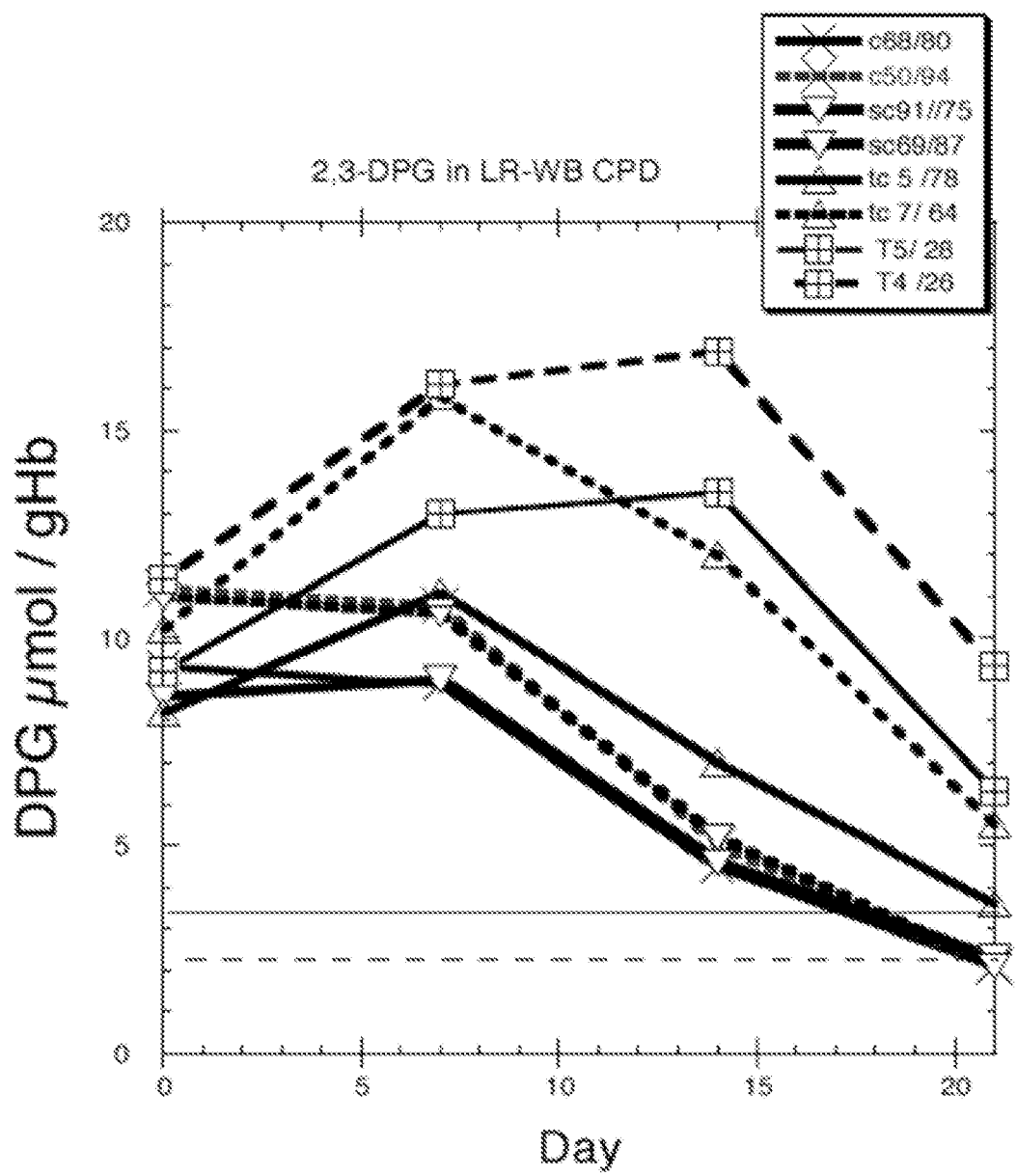
FIGS. 2A to 2G are graphs presenting the results of two experiments according to the present disclosure comparing the storage of leukoreduced whole blood collected in anticoagulant solution CPD (LRWB/CPD) under oxygen reduced, oxygen and carbon dioxide reduced and conventionally stored LRWB/CPD over a period of 21 days.
Figure 2B:
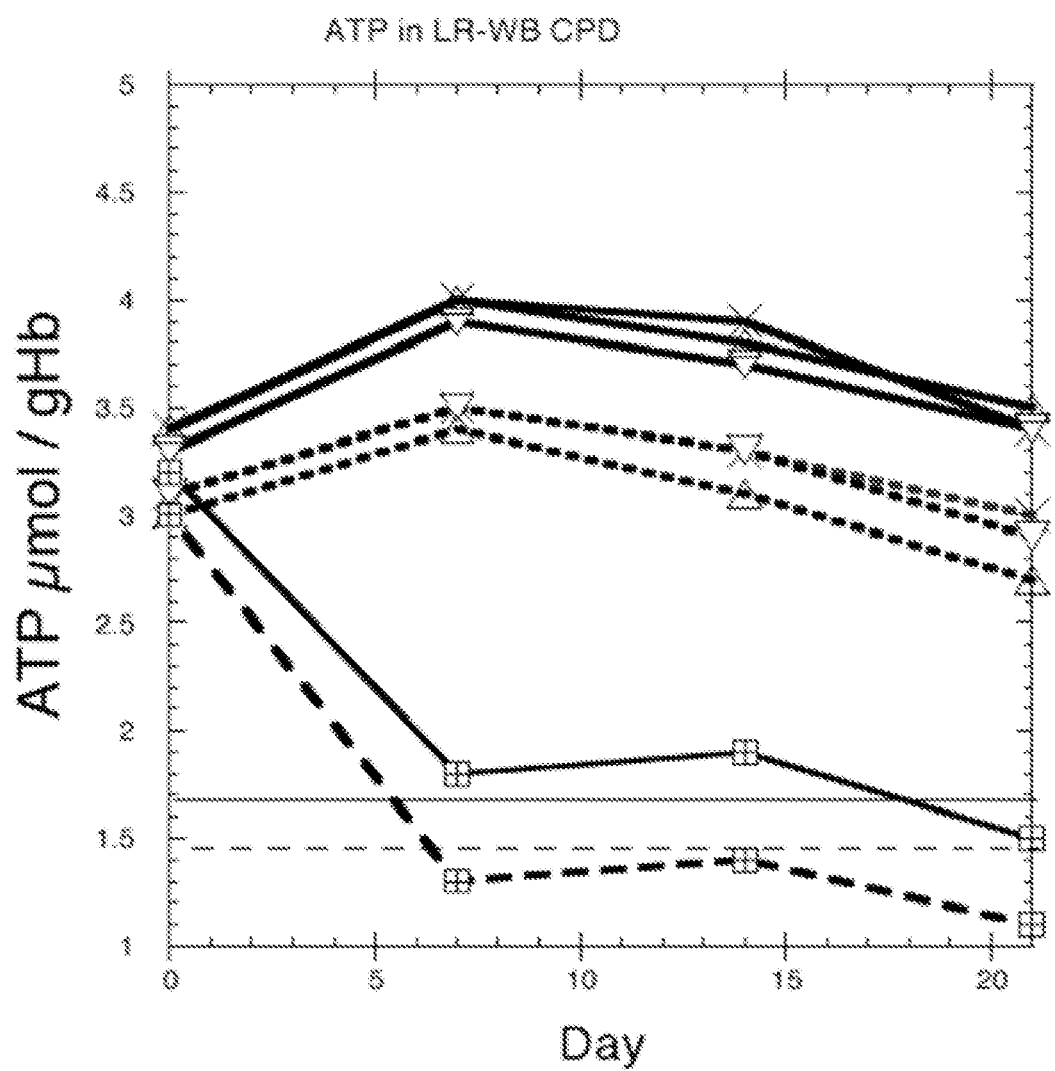
Figure 2C:
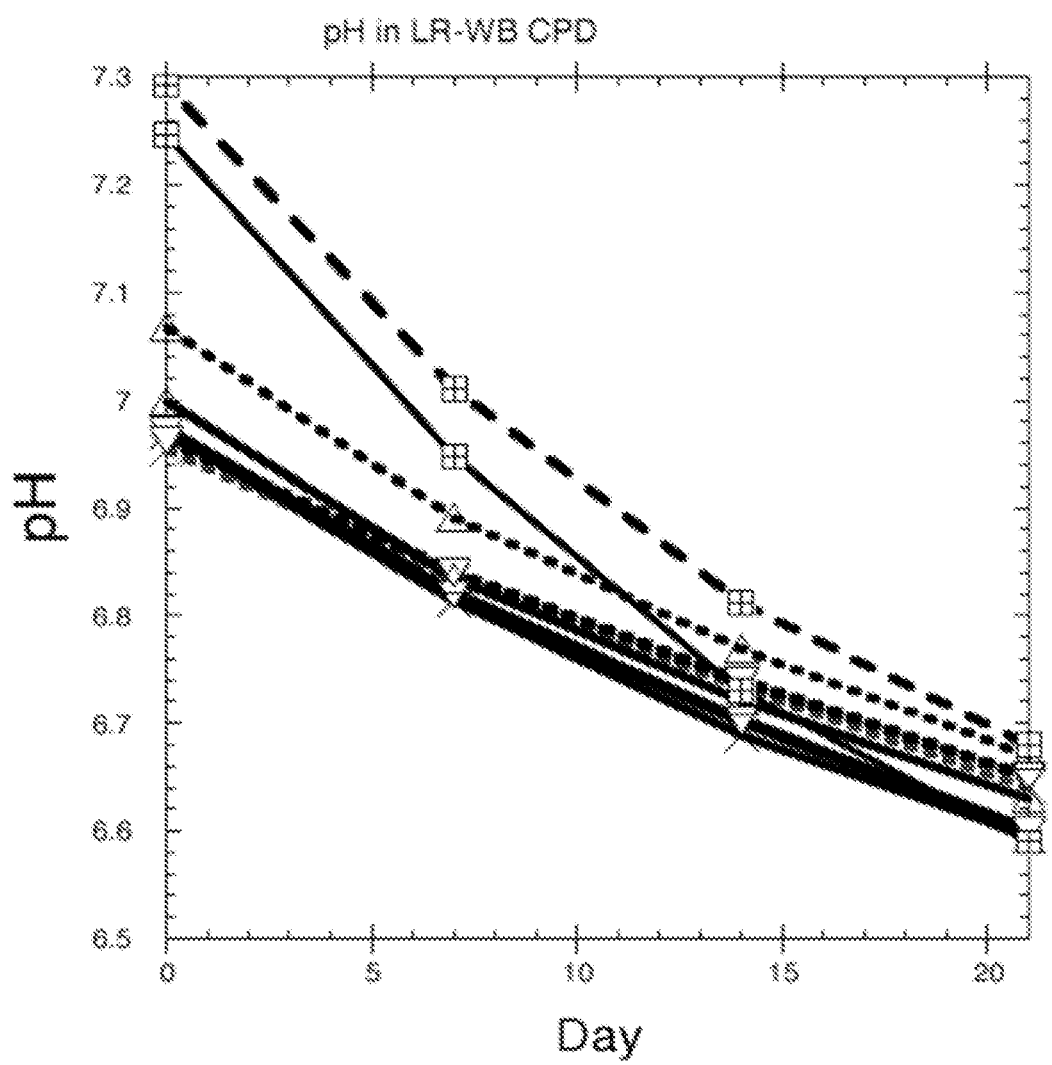
Figure 2D:
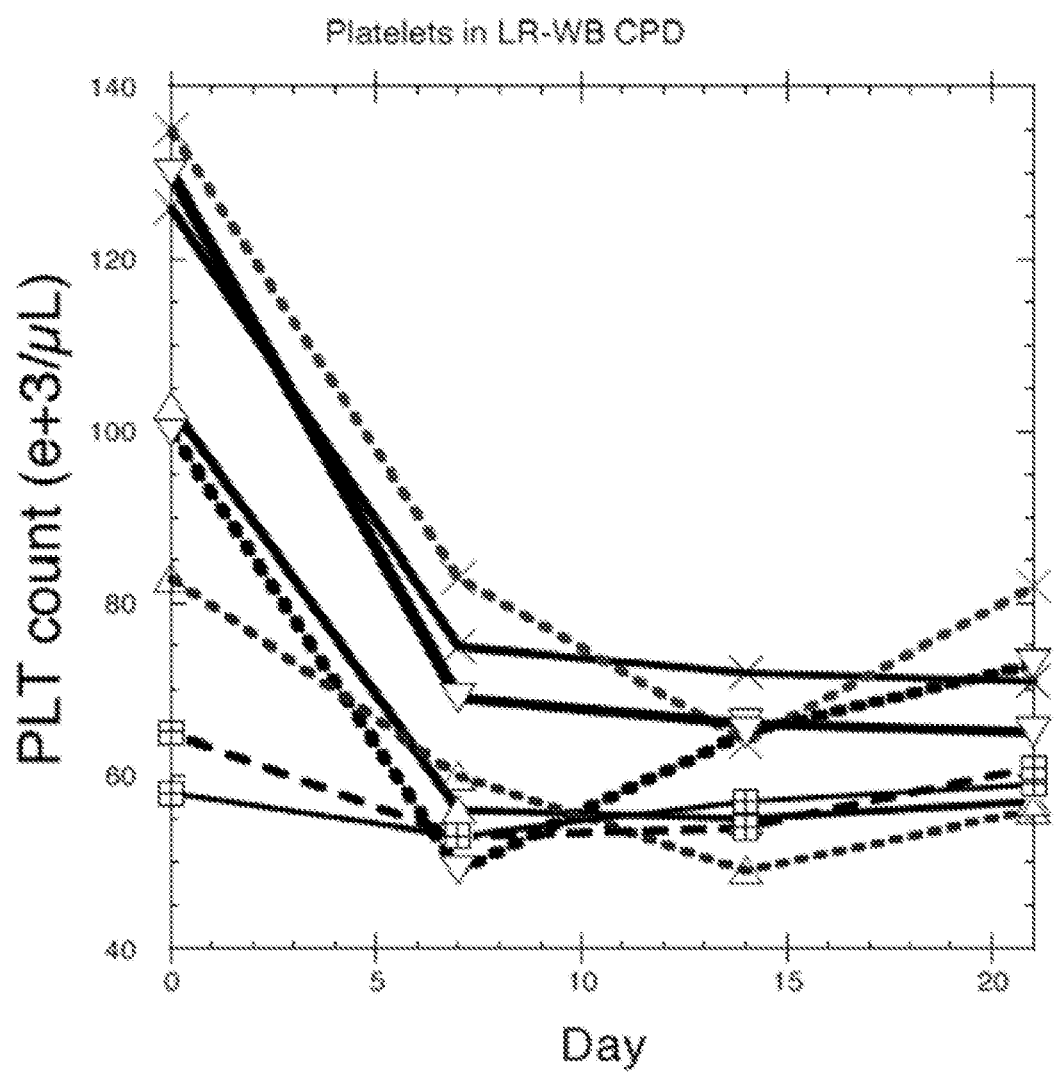
Figure 2E:
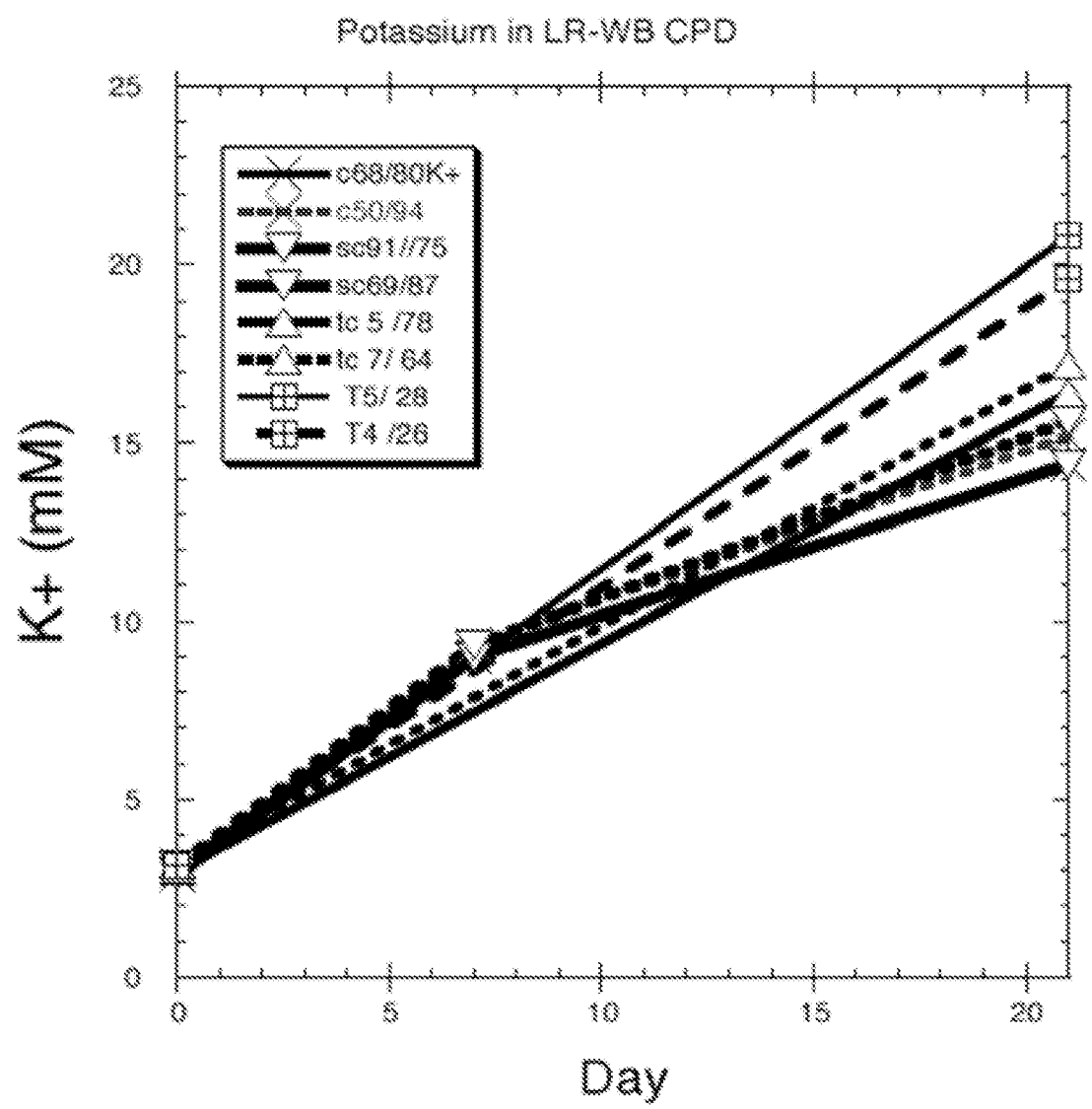
Figure 2F:
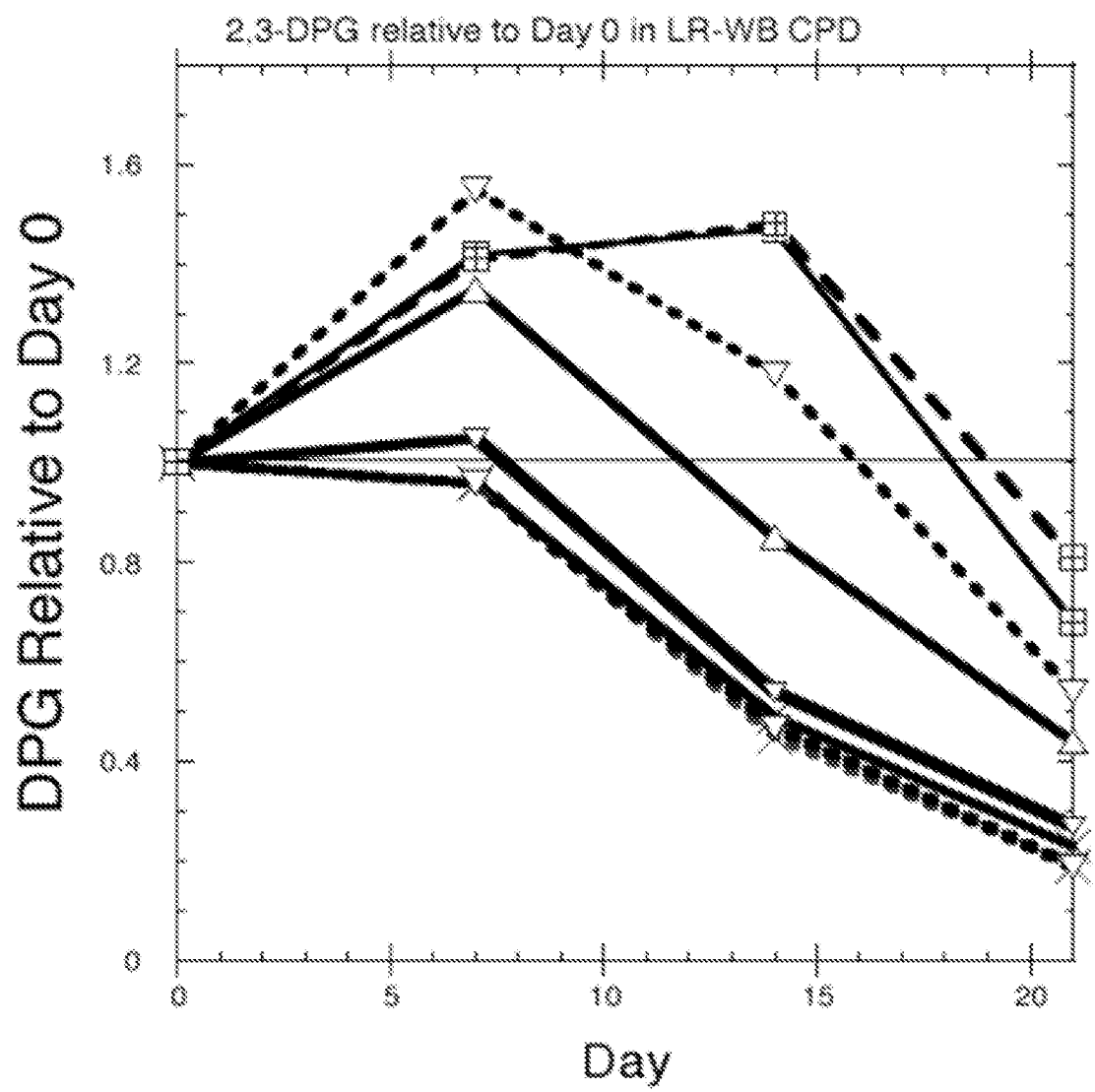
Figure 2G:
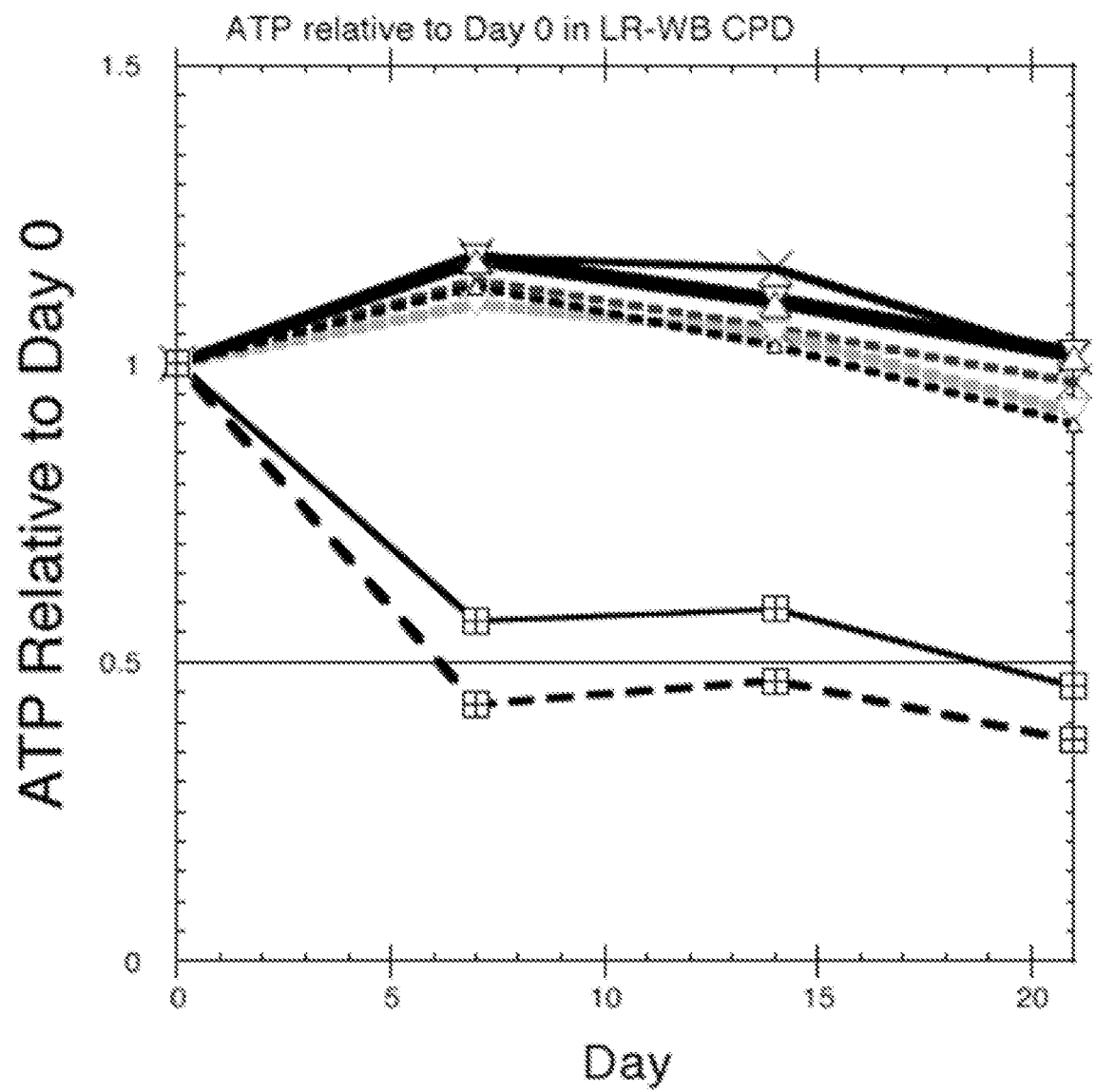
Figure 3A:
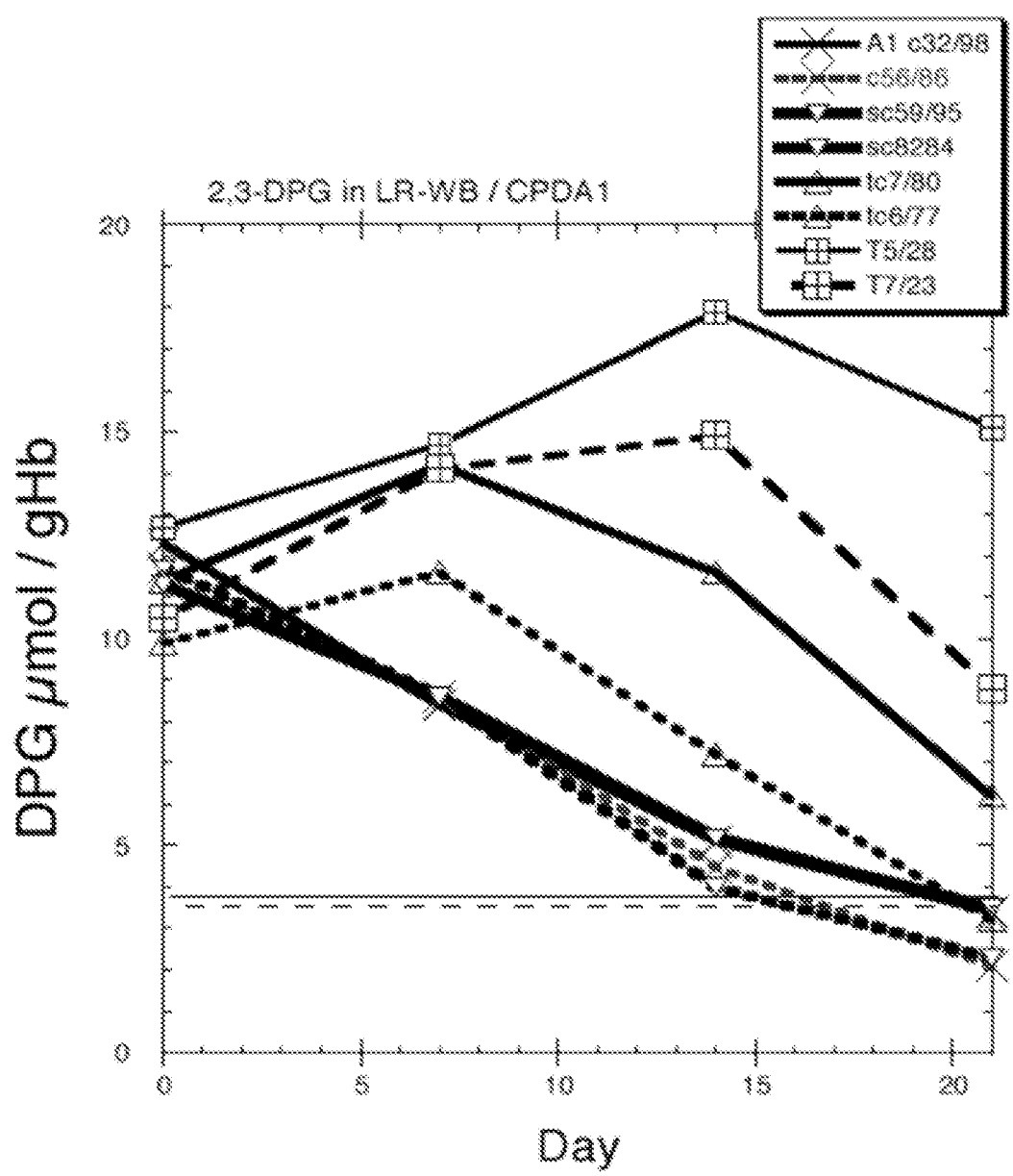
FIGS. 3A to 3D are graphs presenting the results of two experiments according to the present disclosure comparing the storage of leukoreduced whole blood collected in anticoagulant solution CPDA1 (LRWB/CPDA1) under oxygen reduced, oxygen and carbon dioxide reduced and conventionally stored LRWB/CPDA1 over a period of 21 days.
Figure 3B:
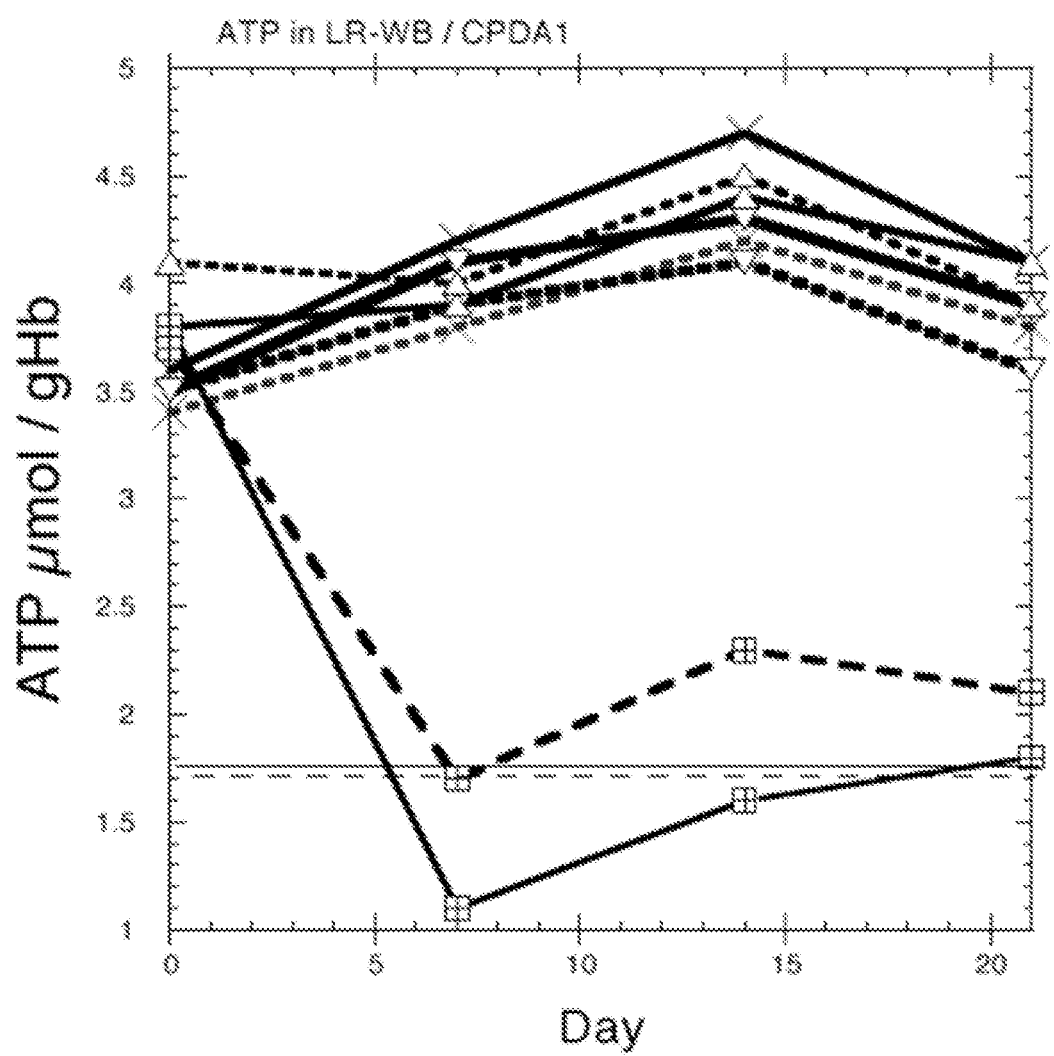
Figure 3C:
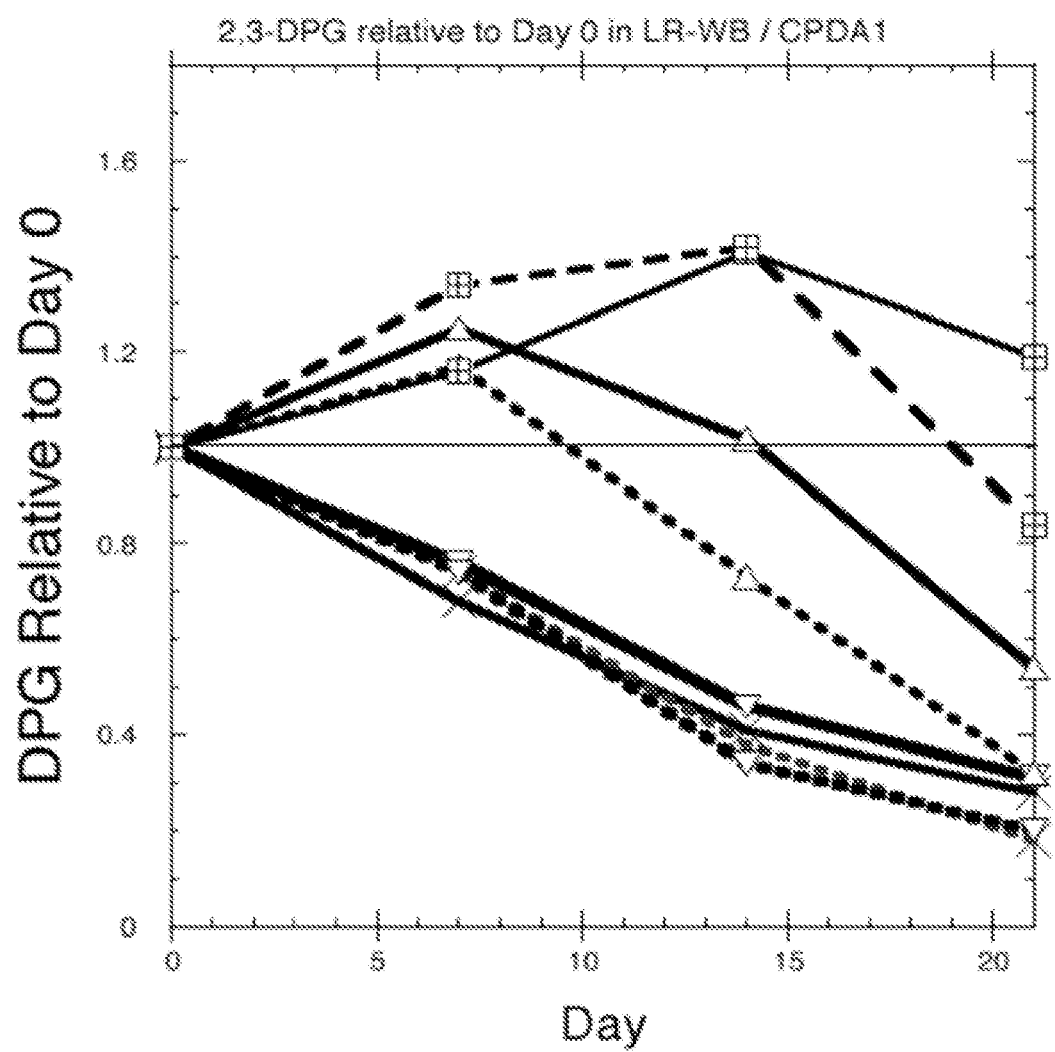
Figure 3D:
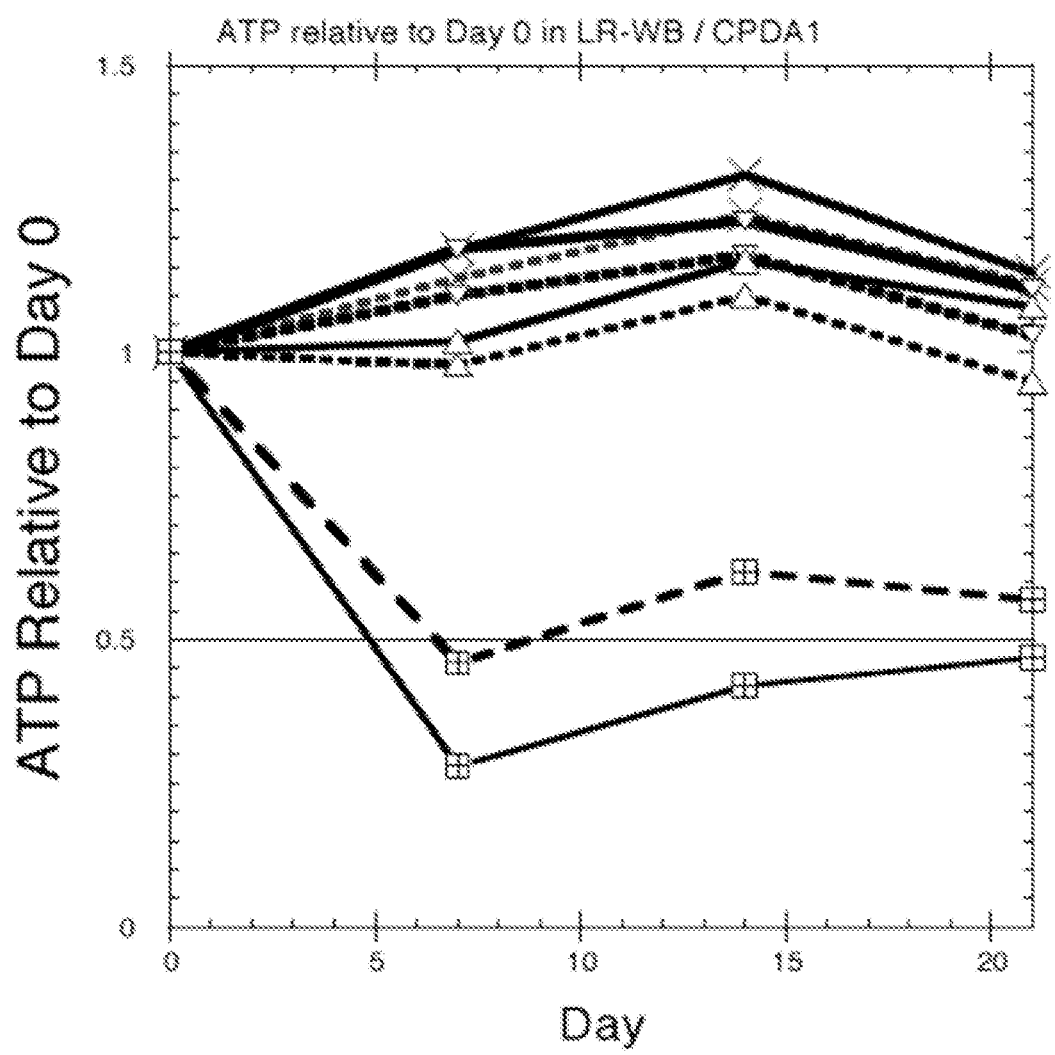

Notably, and as evidenced in FIGS. 2A, 2B, 3A and 3B, the ATP level in stored oxygen reduced blood depends on the partial pressure of $CO_2$. Specifically, depletion of oxygen to about 10% $SO_2$ and carbon dioxide to about 25 mmHg results in increased 2,3-DPG levels that persist beyond 21 days, while ATP decreases to a level of about one half of the initial value. See FIGS. 2G and 3D. Accordingly, the present disclosure provides for, and includes the depletion of oxygen to $SO_2$ levels of about 5% and the depletion of carbon dioxide to a partial pressure of about 30 to 40 mmHg to yield oxygen and carbon dioxide reduced whole blood that has increased levels of 2,3-DPG and that retains at least 50% of the initial concentration of ATP through day 20. In other aspects, the partial pressure of $CO_2$ can be adjusted to retain ATP levels that are at least 75% of the initial ATP value. Adjustment of the level of $CO_2$ can be experimentally determined by one of ordinary skill in the art in view of the present disclosure.

Prolonged hypothermic storage under conventional conditions is known to impair deformability of stored RBCs, potentially compromising their ability to perfuse microvascular networks and deliver oxygen to tissues and vital organs upon transfusion. It is thought that oxidative damage may be a primary contributor to the loss of RBC biomechanical function; therefore, storing RBCs under oxygen reduced (OR) and oxygen and carbon dioxide reduced (OCR) conditions ameliorates oxidative damage, thereby preserving native rheological properties better than conventional (aerobic) storage. For this study, we utilized an in vitro microfluidic system that recapitulates an in vivo microvascular capillary bed to demonstrate the effects of reduced oxygen on stored cells.

The present disclosure provides for, and includes, methods for managing a blood bank that improves the availability of blood products for trauma victims and patients that require multiple transfusions and provides conserving the overall blood resources. The component blood products can be prepared from stored whole blood of the present application and used for transfusions or incorporated into massive transfusion kits. In addition to the improved blood chemistries (low hemolysis, improved 2,3-DPG etc.), the methods provide for improved hemostasis and improved deformability.

In aspects according the present specification, the method provides for maintaining an inventory of blood units comprising oxygen reduced whole blood and an anticoagulant as described above, providing one or more of the blood units from the inventory for treatment of a patient and recycling the blood units from the inventory to prepare component separated oxygen reduced blood units including oxygen reduced plasma and oxygen reduced leukoreduced packed red blood cells with platelets (OR-LRpRBC+PLT). In aspects, the anticoagulant comprises citrate-phosphate-dextrose (CPD), citrate-phosphate-dextrose with adenine (CPDA-1), or CP2D.

In an aspect, the specification provides for a method for maintaining an inventory of blood units comprising oxygen and carbon dioxide reduced leukoreduced whole blood and an anticoagulant as described above, providing one or more of the blood units from the inventory for treatment of a patient and recycling the blood units from the inventory to prepare component separated oxygen reduced blood units including oxygen and carbon dioxide reduced plasma and oxygen and carbon dioxide reduced leukoreduced packed red blood cells with platelets (OCR-LRpRBC+PLT). In aspects, the anticoagulant comprises citrate-phosphate-dextrose (CPD), citrate-phosphate-dextrose with adenine (CPDA-1), or Anticoagulant Citrate Phosphate Double Dextrose (CP2D).

The specification further provides for preparing one or more massive transfusion kits as described below that include the oxygen reduced plasma, oxygen reduced leukoreduced packed red blood cells with platelets (OR-LR-pRBC+PLT), oxygen and carbon dioxide reduced plasma and oxygen and carbon dioxide reduced leukoreduced packed red blood cells with platelets (OCR-LRpRBC+PLT).

In aspects according to the invention, the unused blood in the inventory is recycled after a time period. In certain aspects where the anticoagulant is CPD, the blood units are recycled prior to three weeks of storage. In other aspects where the anticoagulant is CPDA-1, the blood units are recycled prior to five weeks of storage. In yet other aspects, the blood units are recycled after 2 weeks, or less. In an aspect, blood unit recycling occurs between 2 days and 1 week. In another aspect, recycling occurs between 2 days and two weeks. In some aspects, recycling occurs between 1 week and 2 weeks. The timing of recycling can be varied consistent with the turnover and needs of the blood facility.

While the recycling process is preferably performed under anaerobic conditions, the process may also be performed under aerobic conditions. Aerobic conditions may provide a cost savings, but may also be indicated in facilities with higher turnover. In high turnover facilities, the recovered blood components may be used soon after the recycling process and further storage of the blood under anaerobic conditions may provide little additional benefit.

The method for managing a blood bank further provide for the preparation of a massive transfusion kit as described in detail below.

The present disclosure provides for, and includes, methods to provide a supply of blood products for transfusion medicine comprising depleting oxygen from leukoreduced whole blood to prepare oxygen reduced leukoreduced whole blood (OR-LRWB+PLT), storing the oxygen reduced leukoreduced whole blood (OR-LRWB+PLT) for a time period and providing said stored blood to a patient in need thereof. In certain aspects, the leukoreduction step includes platelet reduction to produce oxygen reduced leukoreduced whole blood (OR-LRWB).

The present disclosure provides for, and includes, methods to provide a supply of blood products for transfusion medicine comprising depleting oxygen and carbon dioxide from leukoreduced whole blood to prepare oxygen and carbon dioxide reduced leukoreduced whole blood (OCR-LRWB+PLT), storing the oxygen and carbon dioxide reduced leukoreduced whole blood (OCR-LRWB+PLT) for a time period and providing said stored blood to a patient in need thereof. In certain aspects, the leukoreduction step includes platelet reduction to produce oxygen and carbon dioxide reduced leukoreduced whole blood (OCR-LRWB).

The present disclosure provides for, and includes, methods to provide a supply of blood products for transfusion medicine comprising depleting oxygen from leukoreduced whole blood to prepare oxygen reduced leukoreduced whole blood (OR-LRWB+PLT), storing the oxygen reduced leukoreduced whole blood (OR-LRWB+PLT) for a time period and preparing oxygen reduced leukoreduced packed red blood cells with platelets (OR-LRpRBC+PLT). In certain aspects, the leukoreduction step includes platelet reduction to produce oxygen reduced leukoreduced packed red blood cells (OR-LRpRBC).

The present disclosure provides for, and includes, methods to provide a supply of blood products for transfusion medicine comprising depleting oxygen and carbon dioxide from leukoreduced whole blood to prepare oxygen and carbon dioxide reduced leukoreduced whole blood (OCR-LRWB+PLT), storing the oxygen and carbon dioxide reduced leukoreduced whole blood (OCR-LRWB+PLT) for a time period and preparing oxygen and carbon dioxide reduced leukoreduced packed red blood cells with platelets (OCR-LRpRBC+PLT). In certain aspects, the leukoreduction step includes platelet reduction to produce oxygen and carbon dioxide reduced leukoreduced packed red blood cells (OCR-LRpRBC).

As provided herein, the OR-LRpRBC+PLT, OR-LRpRBC, OCR-LRpRBC+PLT, and OCR-LRpRBC may be returned to the store of blood products for supply and stored for a time period until required for use by a patient. In aspects of the present disclosure, the total time for storage, either as a whole blood product, or as a packed RBC product may be up to six weeks. In some aspects, the second storage period is between 2 to 4 weeks.

The methods for providing a supply of blood products include, and provide, for depleting either oxygen or oxygen and carbon dioxide. The oxygen levels for the methods to provide a supply of blood products are discussed in detail above. In certain aspects, the $SO_2$ value is reduced to 20% or less and the partial pressure of carbon dioxide is less than 60 mmHg. In other aspects, the partial pressure of carbon dioxide is between 10 and 60 mmHg. In another aspect, the partial pressure of carbon dioxide is between 20 and 40 mmHg. Also included are methods that provide for an $SO_2$ of 15% or less and a partial pressure of carbon dioxide of between 10 and 60 mmHg. In another aspect, the methods provide blood products having an $SO_2$ of 15% or less and a partial pressure of carbon dioxide of between 20 and 40 mmHg. In yet another aspect, the methods of the present disclosure provide blood products having an $SO_2$ of 10% or less and a partial pressure of carbon dioxide of between 10 and 60 mmHg. In other aspects, the methods for providing a supply of blood products provide for an $SO_2$ of 10% or less and a partial pressure of carbon dioxide of between 20 and 40 mmHg. In yet further aspects, the methods provide an $SO_2$ of 5% or less and a partial pressure of carbon dioxide of between 10 and 60 mmHg. In other aspects, the methods provide an $SO_2$ of 5% or less and a partial pressure of carbon dioxide of between 20 and 40 mmHg.

The present disclosure provides for, and includes, a new blood composition obtained during the blood component recovery process of OR-LRWB+PLT and OCR-LRWB+PLT. As provided above, while conventional whole blood products have an FDA approved shelf life (3 weeks for WB in CPD and 5 weeks in CPDA1), clinicians who use WB limit its shelf life from between 2 and 14 days. In conventional storage, the blood is often discarded. In the present disclosure, the OR-LRWB+PLT and OCR-LRWB+PLT can be processed using conventional component separation methods modified for retaining the blood in the OR or OCR depleted state. In general, methods are modified to incorporate oxygen and oxygen and carbon dioxide impermeable barriers to the components and incorporating features to prevent oxygen ingress. Suitable approaches can be found, for example in International Patent Application No. PCT/US2016/021794, filed Mar. 10, 2016, and International Patent Application No. PCT/US2016/029069, filed Apr. 22, 2016, both of which are hereby incorporated by reference in their entireties.

In aspects according the present disclosure, a blood composition is provided that comprises oxygen reduced packed red blood cells and platelets having less than $1\times10^5$/L white blood cells. Such compositions are obtainable from OR-LRWB+PLT and OCR-LRWB+PLT. In an aspect, the level of white blood cells is less than $1\times10^4$/L white blood cells. In aspects according to the present disclosure, the oxygen saturation of the oxygen reduced leukoreduced packed red blood cells with platelets (OR-LRpRBC+PLT) is less than 30%. In an aspect, the oxygen saturation of the oxygen reduced leukoreduced packed red blood cells with platelets (OR-LRpRBC+PLT) is less than 20%. In an aspect, the oxygen saturation of the oxygen reduced leukoreduced packed red blood cells with platelets (OR-LRpRBC+PLT) is less than 10%. In a further aspect, the oxygen saturation of the oxygen reduced leukoreduced packed red blood cells with platelets (OR-LRpRBC+PLT) is less than 5%.

The present disclosure provides for, and includes, oxygen and carbon dioxide reduced leukoreduced packed red blood cells with platelets (OCR-LRpRBC+PLT) having less than 30% $SO_2$ and a storage partial pressure of carbon dioxide of less than 60 mmHg. In an aspect, the OCR-LRpRBC+PLTs have an oxygen saturation of less than 30% and a storage partial pressure of carbon dioxide between 20 and 40 mmHg. In an aspect, the OCR-LRpRBC+PLTs have an oxygen saturation of less than 30% and a storage partial pressure of carbon dioxide between 0 and 20 mmHg. In an aspect, the OCR-LRpRBC+PLTs have an oxygen saturation of less than 20% and a storage partial pressure of carbon dioxide of less than 60 mmHg. In an aspect, the OCR-LRpRBC+PLTs have an oxygen saturation of less than 20% and a storage partial pressure of carbon dioxide between 20 and 40 mmHg. In an aspect, the OCR-LRpRBC+PLTs have an oxygen saturation of less than 20% and a storage partial pressure of carbon dioxide between 0 and 20 mmHg. In another aspect, the OCR-LRpRBC+PLTs have an oxygen saturation of less than 15% and a storage partial pressure of carbon dioxide of less than 60 mmHg. In an aspect, the OCR-LRpRBC+PLTs have an oxygen saturation of less than 15% and a storage partial pressure of carbon dioxide between 20 and 40 mmHg. In an aspect, the OCR-LRpRBC+PLTs have an oxygen saturation of less than 15% and a storage partial pressure of carbon dioxide between 0 and 20 mmHg. In another aspect, the OCR-LRpRBC+PLTs have an oxygen saturation of less than 10% and a storage partial pressure of carbon dioxide of less than 60 mmHg. In an aspect, the OCR-LRpRBC+PLTs have an oxygen saturation of less than 10% and a storage partial pressure of carbon dioxide between 20 and 40 mmHg. In an aspect, the OCR-LRpRBC+PLTs have an oxygen saturation of less than 10% and a storage partial pressure of carbon dioxide between 0 and 20 mmHg. In other aspects, the OCR-LRpRBC+PLTs has an oxygen saturation of less than 5% and a storage partial pressure of carbon dioxide of less than 60 mmHg. In an aspect, the OCR-LRpRBC+PLTs have an oxygen saturation of less than 5% and a storage partial pressure of carbon dioxide between 20 and 40 mmHg. In an aspect, the OCR-LRpRBC+PLTs have an oxygen saturation of less than 5% and a storage partial pressure of carbon dioxide between 0 and 20 mmHg.

The oxygen reduced leukoreduced packed red blood cells with platelets (OR-LRpRBC+PLT) and oxygen and carbon dioxide reduced leukoreduced whole blood with platelets (OCR-LRWB+PLT) usually further comprise an additive solution. Suitable additive solutions according to the present disclosure include AS-1, AS-3)(Nutricel®, AS-5, SAGM, PAGG-SM, PAGG-GM, MAP, AS-7, ESOL-5, EAS61, OFAS1, OFAS3, and combinations thereof. In an aspect, the additive solution is added at the time of component separation. In an aspect, the additive solution is AS-1. In another aspect, the additive solution is AS-3. In other aspects, the additive solution is SAGM.

The methods and compositions of the present disclosure provide for and include the preparation of 'massive transfusion kits' (MTKs) having improved properties to kits prepared from conventional components. The massive transfusion kits of the present disclosure can be prepared in various configurations depending on the clinical needs. The MTKs of the present disclosure are stored under oxygen free or oxygen and carbon dioxide free conditions until being prepared for use. The OR and OCR conditions can be maintained by sealing in an impermeable enclosure either with, or without, an appropriate sorbent material. The MTKs of the present disclosure may be re-oxygenated prior to use, or used directly. In general, the specification provides for massive transfusion kits optimized to deliver RBCs having improved 2,3-DPG levels. Such kits are prepared from component blood products obtained from oxygen and carbon dioxide reduced leukoreduced whole blood with platelets (OCR-LRWB+PLT). Alternatively, a kit may be prepared using component blood products obtained from oxygen reduced leukoreduced whole blood with platelets (OR-LRWB+PLT) to produce kits having higher levels of ATP. Kits prepared using the methods of the present specification provide platelets suitable for hemostasis together with the oxygen reduced stored red blood cells. Thus, massive transfusion kits of the present specification can increase the availability of platelets without additional dilution while further providing RBCs of higher quality (e.g., more deformable, more 2,3-DPG, fewer storage lesions). Importantly, the recovery of blood components from the oxygen reduced whole blood of the present disclosure increases the availability of transfusion products for trauma victims and saves and conserves a valuable and limited resource. As discussed above, conventional massive transfusion kits include a volume of plasma, a volume of pRBCs, and volume of platelets in a 1:1:1 ratio wherein the amounts of the three components correspond to a unit 'reconstituted blood' when transfused serially or in parallel to a patient in need. Reconstituted blood does not directly correspond to whole blood which does not include an additive solution and has higher levels of anti-coagulant. Further reconstituted blood typically includes a larger volume than a typical unit of whole blood. The reconstituted blood of the present disclosure is improved over the conventional reconstituted blood as it provides additional platelets in the pRBC fraction (e.g., either oxygen and carbon dioxide reduced leukoreduced packed red blood cells with platelets (OCR-LRpRBC+PLT) and oxygen reduced leukoreduced packed red blood cells with platelets (OR-LRpRBC+PLT)). Such cold stored platelets undergo modification commonly known as platelet storage lesions (PSLs) and cold stored platelets are quickly removed from circulation in the body. Importantly, cold stored platelets retain the ability to aggregate and have been reported to have increased aggregations and resistance to disaggregation. Accordingly, blood components obtained from the oxygen reduced whole blood of the present specification provide additional benefits during trauma transfusion, either alone or in combination with conventional platelets.

The present disclosure provides for, and includes, a massive transfusion kit comprising a volume of oxygen reduced leukoreduced packed red blood cells with platelets (OR-LRpRBC+PLT) or oxygen and carbon dioxide reduced leukoreduced whole blood with platelets (OCR-LRWB+PLT), or combinations thereof. In an aspect, a massive transfusion kit provides a volume of plasma and a volume of LRpRBC+PLT. In an aspect, the volume of plasma and a volume of LRpRBC+PLT is 1:1. In other aspects, the ratio of plasma to LRpRBC+PLT is between 1:1 and 1:2 by volume. In an aspect, the ratio of plasma to LRpRBC+PLT is about 1:2 by volume.

The present disclosure provides for, and includes, massive transfusion kits that include additional platelets together with the plasma and oxygen reduced leukoreduced packed red blood cells with platelets (OR-LRpRBC+PLT) or oxygen and carbon dioxide reduced leukoreduced whole blood with platelets (OCR-LRWB+PLT).

The massive transfusion kits of the present disclosure provide for a volume of plasma. The plasma of the MTKs can be either fresh plasma or thawed fresh frozen plasma (FFP). The specification provides for obtaining the plasma for MTKs from either conventional sources (e.g., non-oxygen reduced) or from oxygen reduced or oxygen and carbon dioxide reduces sources. In an aspect, the plasma for an MTK of the present disclosure may be obtained from oxygen reduced leukoreduced whole blood (OR-LRWB), oxygen reduced leukoreduced whole blood with platelets (OR-LRWB+PLT), oxygen and carbon dioxide reduced leukoreduced whole blood (OCR-LRWB), or oxygen and carbon dioxide reduced leukoreduced whole blood with platelets (OCR-LRWB+PLT). Not to be limited by theory, the plasma obtained from the oxygen reduced sources will have lower levels of storage lesions, including for example, lower levels of cytokines, isoprostane, and microparticles. As provided herein, MTKs having plasma, platelets and pRBCs according to the present specification are provided at a ratio of between 1:1:1 or 1:1:2 by volume. It will be understood to one of ordinary skill in the art that the MTKs of the present disclosure, like conventional MTKs, are designed to provide an equivalent of a unit of blood. It will be recognized that any arbitrary total volume may be selected while maintaining the recited ratios necessary to be equivalent to reconstituted blood.

EXAMPLES

Example 1: Cytokine, Cell-Free Hemoglobin, and Isoprostane Accumulations in Packed Red Blood Cells During Anaerobic Storage Fifteen pRBC units are collected from normal healthy donors. Each unit is split and stored as follows: one in standard blood bank conditions (control), the other anaerobically (test) according to methods described in Yoshida et al., "Anaerobic Storage of Red Blood Cells in a Novel Additive Solution Improves In vivo Recovery," *Transfusion* 49:458-64 (2008). At weeks 0, 1, 2, 3, and 6, samples are removed using a sterile connecting device from the PRBC units. Plasma samples are frozen for the following assays: single batch testing for 22 cytokines using the Procarta Immunoassay Magnetic Bead kit, 8-isoprostane $F_R$, via mass spectrometric assay, and cell free hemoglobin via HemoCue plasma/photometer (HemoCue AB, Angelholm, Sweden).

Figure 1B:
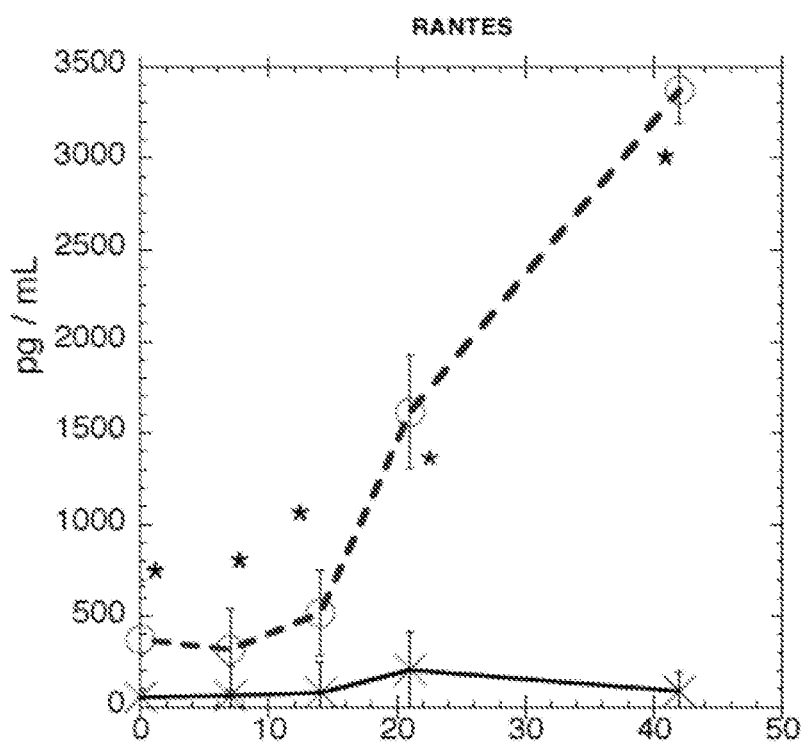
Figure 1C:
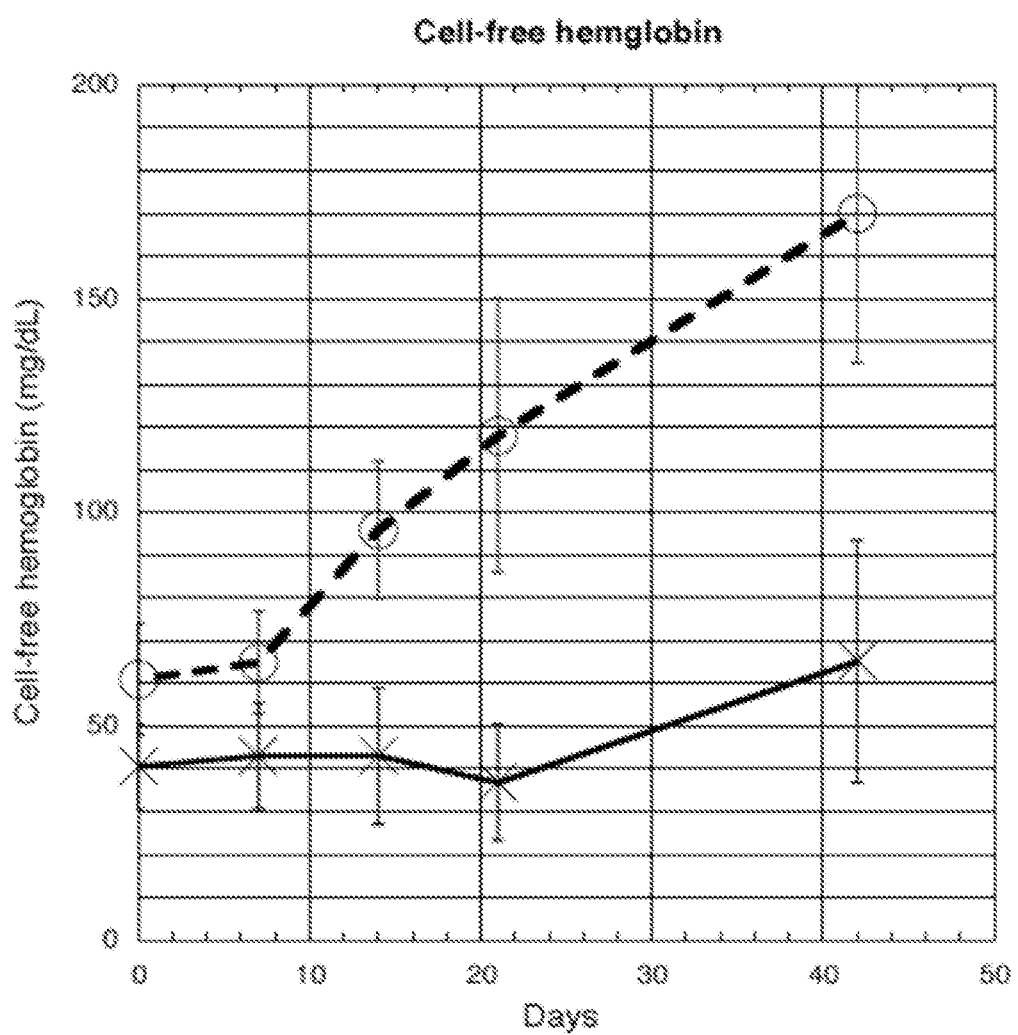
Figure 1D:
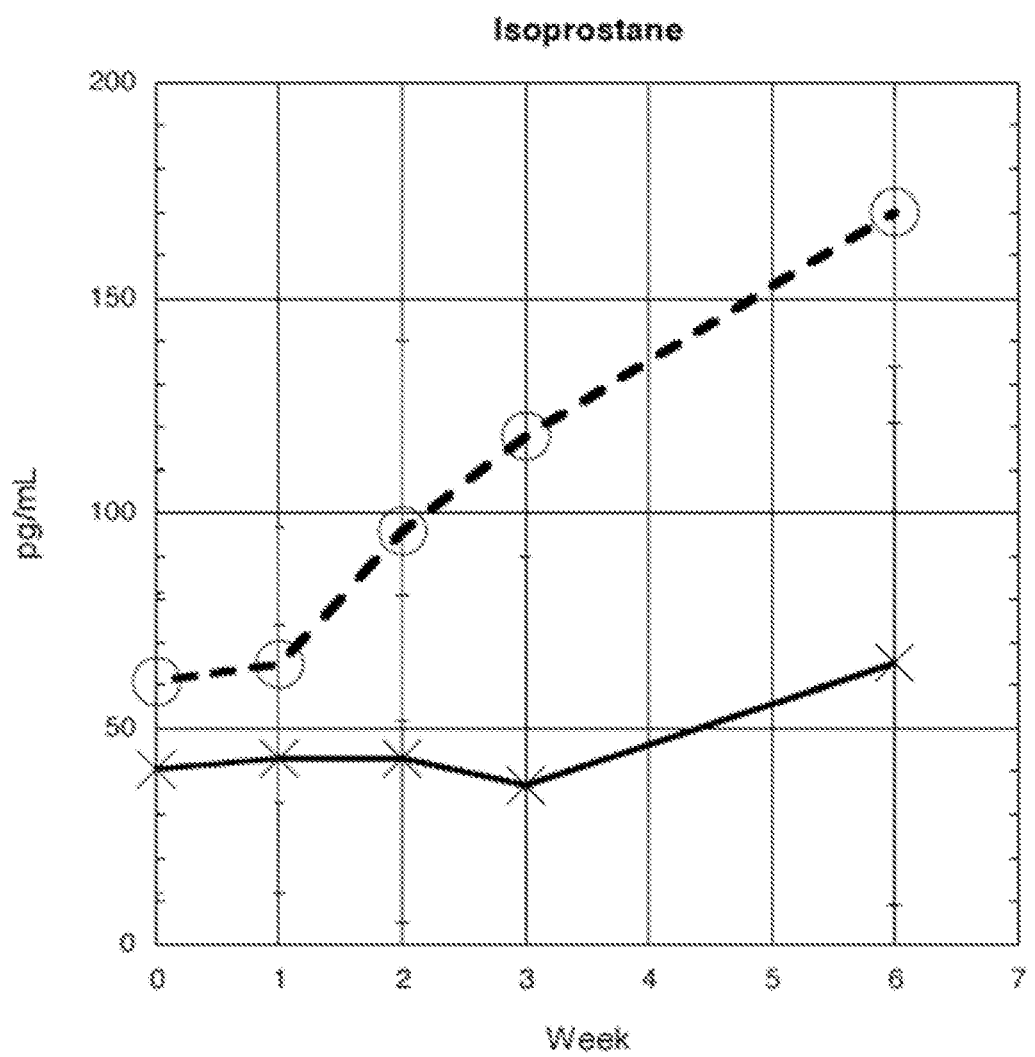

As shown in FIG. 1A, eotaxin reaches a statistically significant difference at week 2 (86.6 pg/ml-control (c), 64.9-test (t), p-value—0.00213, with statistical significance of $p<0.05$; day 42 (292-c, 112-t; p=0.000). As shown in FIG. 1B, RANTES is different at all time points, starting at day 3 (374.6-c, 55.1-t), p-=0.00000; a very large difference is observed on day 42 (3371.6-c, 88.4-t; p<0.002). As shown in FIG. 1C, differences in cell-free hemoglobin are seen at week 2 (96.0 mg/dl-c, 41.7-t), p-=0.00001; day 42 (170-c, 63-t, p=0.0002). As shown in FIG. 1D, storage day 3 shows differences in isoprostane (45.5 pg/ml-c, 32.1-t), p=0.00689; day 42 (101.9-c, 64.7-t, p=0.0048).

Example 2: Collection, Leukoreduction and Gas Depletion of Whole Blood

A unit of blood is collected from a donor patient into anticoagulant solution comprising either CPDA1 or CPDA according to standard protocols, including collection of heparin tubs. The collected blood containing anticoagulant is leukoreduced according to manufacturer's instructions less than or equal to four hours after the initial blood draw. Baseline ABL90 blood gas and metabolic parameters are determined from the donor heparin tube and the whole blood product according to standard procedures. See BSL Handbook Procedure BSL-P024: Procedure Manual and Radiometer ABL90 FLEX Gas Analyzer instructions.

An anaerobic control is prepared from each unit of leukoreduced blood by transferring 120 ml of LRWB/CPDA-1 or LRWB/CPD into a 150 mL transfer bag, labeled as appropriate and placed at room temperature (15°-30° C.).

The remainder of the LRWB LRWB/CPDA-1 or LRWB/CPD is processed for oxygen or oxygen and carbon dioxide depletion by transferring to a blood processing bag connected to a Sorin D100 and processed for 5 minutes at a flow rated of 700 ml/minute without gas to generate a BOF processing control. 120 g of the resulting BOF processed blood is transferred to a 300 ml transfer bag that has been stored under anaerobic conditions and labeled BOF processing control. The remainder of the LRWB/CPDA-1 or LRWB/CPD is processed on the Sorin D100 at a peak flow rate of 700 ml/minute with a gas flow rate of 3 L/min of a gas composition comprising 5% $CO_2$/95% $N_2$ until the blood reaches ~5% $SO_2$ measuring blood gas values on a Radiometer ABL90 FLEX Gas Analyzer at 3 to 5 minute intervals. To reduce carbon dioxide levels, the gas mixture is switched to 100% $N_2$ for 1 to 4 minutes until $SO_2$ reaches 5±1% and $pCO_2$ reaches 30±3 mmHg, monitoring blood gas values every 15-30 seconds to monitor deoxygenation rate. 120 g of the resulting oxygen and carbon dioxide reduced LRWB/CPDA-1 or LRWB/CPD is transferred to a 300 ml transfer bag previously stored under anaerobic conditions as described above and labeled ("C"). Further processing of the LRWB/CPDA-1 or LRWB/CPD is performed on the Sorin D100 at a flow rate of 700 ml/min with 99% $N_2$ and 1% $O_2$ until the LRWB/CPDA-1 or LRWB/CPD reaches an $SO_2$ of 5±1% and $pCO_2$ reaches 7±3 mmHg. 120 g of the resulting oxygen and carbon dioxide reduced LRWB/CPDA-1 or LRWB/CPD is transferred to a 300 ml transfer bag previously stored under anaerobic conditions as described above and labeled ("D"). Additional samples are processed as described above using a new Sorin D100. Immediately following the preparation of each sample, ABL90 blood gas levels are determined according to manufacturer's instructions to establish baseline $SO_2$ and $pCO_2$ levels (e.g., $T_0$). See BSL Handbook Procedures. Samples for cytokine analysis are collected and stored at −80° C. for later analysis.

All samples are analyzed as provided below at Example 6.

Example 3: Storage of Anaerobic Test Products

Oxygen reduced and oxygen and carbon dioxide reduced blood in transfer bags are wrapped in mesh, secured with elastic and placed in anaerobic canisters with 4 sorbent sachets (Mitsubishi, SS-300). Canisters are sealed and the canister purged of air using an Alicat Gas Processing System. See BSL Handbook Procedure BSL-P040: Procedure for Placing Blood Products in Anaerobic Storage in Canisters. Anaerobic and aerobic blood is placed in a Blood Bank refrigerator at 1 to 6° C. Canister gauges are monitored daily to ensure that they read 5±1 psi. Canisters that fall below 2 psi are adjusted to standard procedures. See BSL Handbook Procedure BSL-P040: Procedure for Placing Blood Products in Anaerobic Storage in Canisters.

Example 4: Sample Testing

Samples are tested at indicated time points: day zero ($T_0$) post processing, day 1, week 1, week 2, and week 3. Samples may be tested fresh or frozen for later testing as appropriate for a given test. The testing includes a complete blood count (CBC), Thromboelastography (TEG).

Prepare platelet rich plasma (PRP) for platelet aggregation immediately per manufacturer's instructions.

Perform coagulation screening and additional assays per manufacturer's instructions.

Prepare samples for cytokines immediately per manufacturer's instructions.

Example 5: ATP Sampling and Measurement

Samples are processed for ATP measurement by deproteinization and precipitation. 1 ml of sample (e.g., LRWB/CPD or LRWB/CPDA-1 or samples described above) is precipitated with 1.0 ml ice cold trichloroacetic acid (TCA) (12% w/v) and vortexed for 15 to 30 seconds and incubated on ice for 5 minutes. Tubes containing the TCA/Sample mixture are centrifuged at 3600 g for 5 minutes at 4° C.

International Patent Publication No. WO 2013/177339, published Nov. 28, 2013. High speed image sequences (~150 FPS) of the blood samples traversing artificial microvascular network (AMVN) chip are recorded. The occlusion time, the amount of time flow through the network that is obstructed by non-deformable cells and the frequency at which blood profusion through the network is interrupted (occlusion frequency) are determined.

Overall bulk perfusion rates through the AMVN system are consistently higher for $O_2$ and $CO_2$ controlled blood compared to aerobically stored units and the total occlusion time is consistently lower for oxygen reduced RBCs (Table 1). These results suggest that reduction of oxygen levels in LR-RBC units mitigates the deterioration of the biomechanical properties of the red blood cell during hypothermic storage.

The oxygen depletion and storage process significantly reduces the rate at which the rheological properties of RBCs deteriorate during hypothermic storage, and is capable of preserving more physiologically relevant biomechanical properties of the red cells during storage. The improved deformability of the RBCs combined with the benefits of whole blood transfusion indicates that the preserved RBC function will improve retention of RBCs post transfusion, and increased capability of transfused RBCs to profuse the microvasculature.

TABLE 1

Perfusion rates of Blood Cells After Oxygen Reduced Storage

| | | Week 0 | Week 1 | Week 2 | Week 3 | Week 4 | Week 5 | Week 6 |
|---|---|---|---|---|---|---|---|---|
| MMCN perfusion rate (pL/s) | $O_2$ Reduced | 203.8 ± 7.4 | 182.3 ± 13.0 | 167.1 ± 18.2 | 155.2 ± 12.3 | 133.2 ± 17.0 | 131.7 ± 14.1 | 122.7 ± 10.7 |
| | Conventional | 200.4 ± 8.5 | 173.8 ± 10.6 | 160.0 ± 18.1 | 142.9 ± 8.8 | 122.3 ± 12.2 | 117.0 ± 12.5 | 106.2 ± 14.2 |
| MMCN plugging event time (%) | $O_2$ Reduced | 18.1 ± 8.5 | 36.6 ± 7.8 | 35.4 ± 10.3 | 45.9 ± 5.1 | 59.1 ± 8.5 | 60.1 ± 7.5 | 63.4 ± 2.1 |
| | Conventional | 21.3 ± 9.6 | 41.0 ± 10.0 | 42.1 ± 13.8 | 56.5 ± 2.9 | 67.3 ± 8.8 | 68.1 ± 7.6 | 71.3 ± 6.1 |
| AMVN perfusion rate (pL/s) | $O_2$ Reduced | 222.8 ± 12.5 | 206.7 ± 6.3 | 200.6 ± 3.5 | 186.4 ± 6.7 | 187.0 ± 12.7 | 176.5 ± 13.5 | 171.4 ± 13.7 |
| | Conventional | 220.0 ± 14.9 | 200.8 ± 7.4 | 194.3 ± 8.8 | 182.3 ± 3.5 | 181.8 ± 12.0 | 171.9 ± 11.2 | 162.0 ± 11.7 |

Samples are immediately processed to minimize exposure to TCA. The clarified supernate is transferred to a pre-cooled tube and snap frozen on a dry ice alcohol bath and stored at −70° C.

Example 6: Improved Deformability in Stored RBCs that have been Stored Under Oxygen Reduced Conditions Nine (9) individual units of whole blood are obtained from healthy consenting volunteers via a standard 500 mL blood donation. Donated whole blood is processed into leukoreduced red blood cell (LR-RBC) units according to standard AABB/FDA guidelines; the resulting units are then split into two halves. One half of the units are $O_2$ and $CO_2$ reduced as described in Examples 2 and 3.

The resulting samples are placed in anaerobic, hypothermic storage, while the second half is placed in conventional, aerobic hypothermic storage. Paired RBC units are stored in a blood bank refrigerator and evaluated weekly for the entire duration of 6-week storage. Prior to testing, the hematocrit of all RBC samples was adjusted to 40% using normal saline (0.9% NaCl; RBC-S). The deformability of the RBC-S at the beginning and during the study is determined as described in Example 7: Deoxygenation of Platelets does not Impede Hemostatic Performance Eight (8) units of whole blood (WB) are obtained from healthy consenting volunteers via a standard 500 mL blood donation. Donated whole blood is collected in CPDA-1 anticoagulant as described in Example 2 (Research Blood Components, Inc.) and leukoreduced with a platelet sparing filter (Imuflex® WB-SP) (LRWB; Terumo Medical Corporation). The resulting filtered units are then split into two halves. One half of the units are placed in conventional, aerobic hypothermic storage, while the second half is further divided and placed in anaerobic, hypothermic storage. The anaerobically stored units are oxygen reduced (OR-LRWB) or oxygen and carbon dioxide reduced (OCR-LRWB). The anaerobically stored units are processed with the Sorin D100 membrane oxygenator to yield anaerobic units with about 5% $SO_2$ and about 35 $mmHgpCO_2$. The resulting anaerobic units are placed in standard PVC bags and stored in anaerobic canisters comprising oxygen sorbent and Nitrogen gas. Paired leukoreduced platelet units are evaluated weekly for the entire duration of 21 day storage as described below.

Figure 4A:
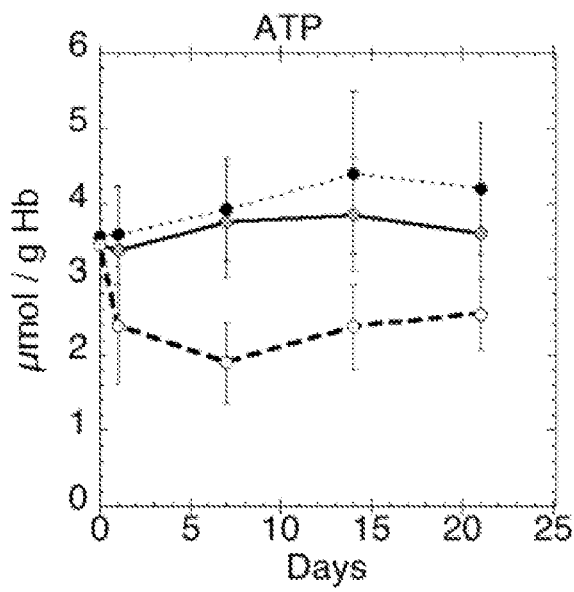
FIGS. 4A to 4C are graphs presenting the results of experiments according to the present disclosure comparing the storage of leukoreduced whole blood collected in anticoagulant solution CPDA1 (LRWB/CPDA1) under oxygen reduced (OR), oxygen and carbon dioxide reduced (OCR) and conventionally stored LRWB/CPDA1 over a period of 21 days.
Figure 4B:
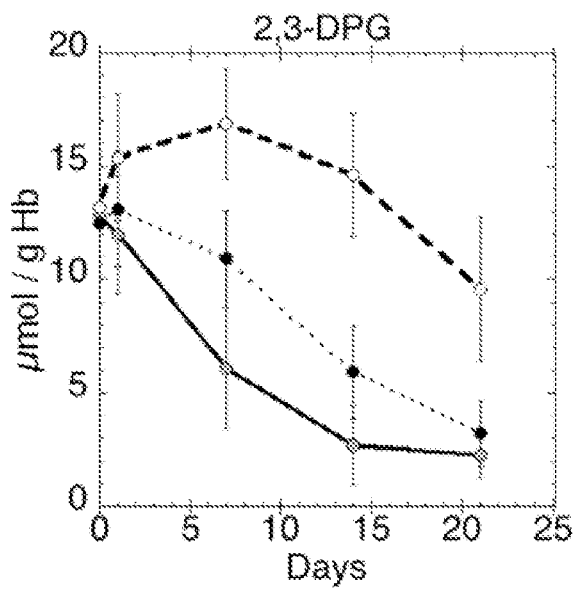
Figure 4C:
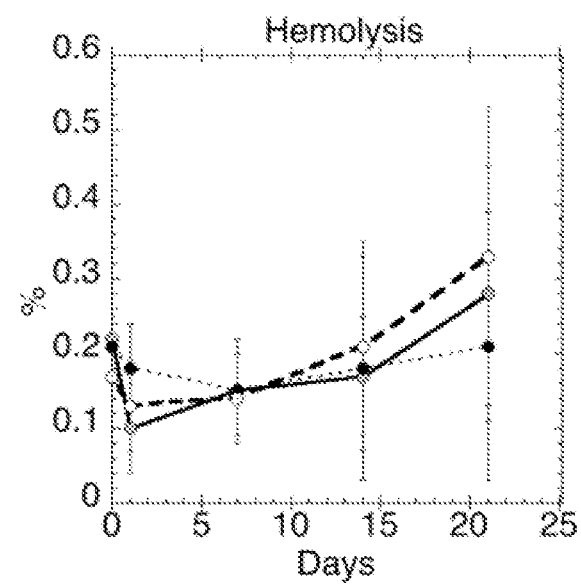
Figure 5A:
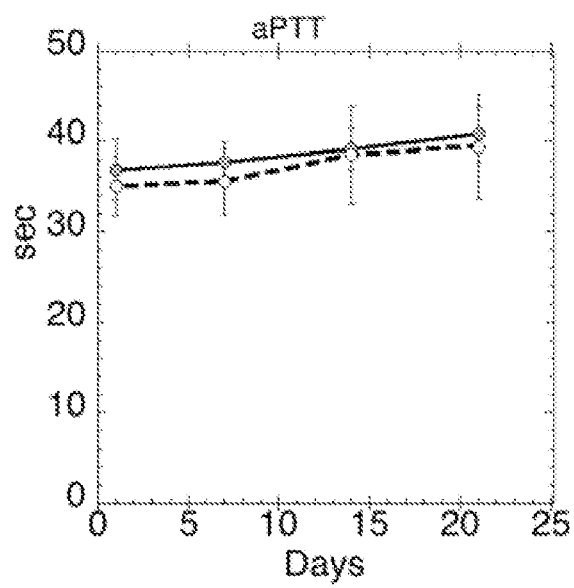
FIGS. 5A to 5D are graphs presenting the results of experiments according to the present disclosure comparing the storage of leukoreduced whole blood collected in anticoagulant solution CPDA1 (LRWB/CPDA1) under oxygen and carbon dioxide reduced and conventionally stored LRWB/CPDA1 over a period of 21 days.
Figure 5B:
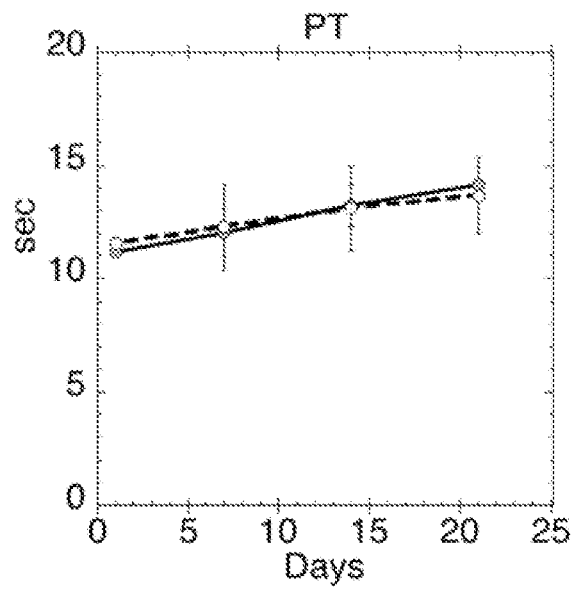
Figure 5C:
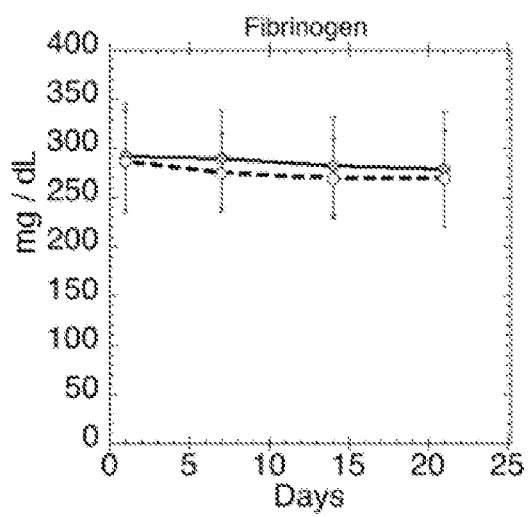
Figure 5D:
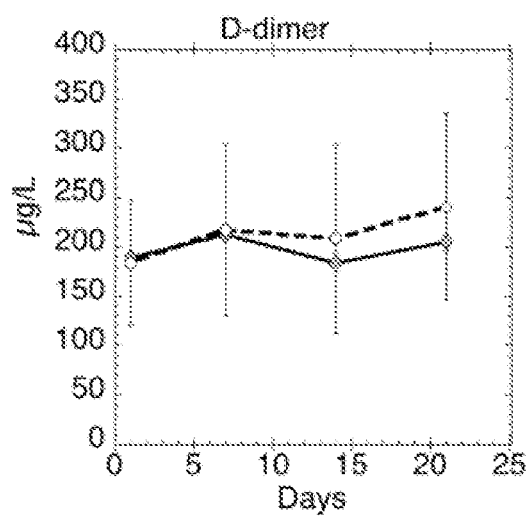
Figure 6A:
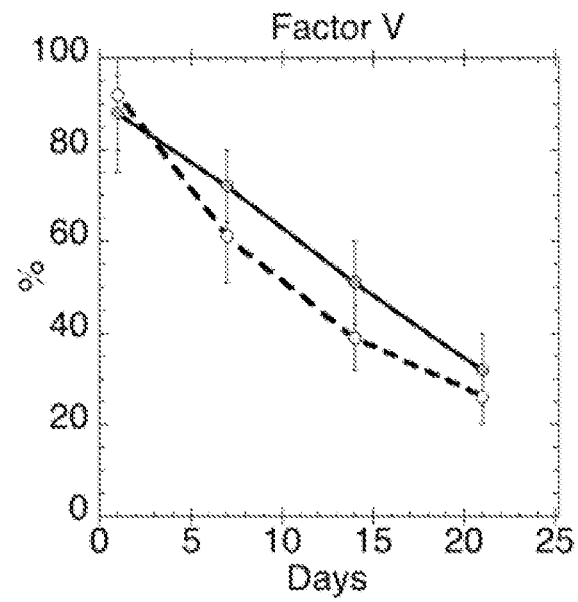
FIGS. 6A to 6E are graphs presenting the results of experiments according to the present disclosure comparing the storage of leukoreduced whole blood collected in anticoagulant solution CPDA1 (LRWB/CPDA1) under oxygen and carbon dioxide reduced and conventionally stored LRWB/CPDA1 over a period of 21 days.
Figure 6B:
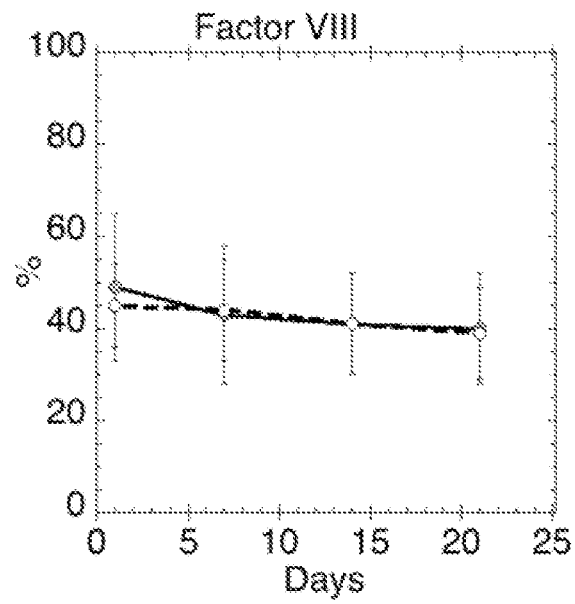
Figure 6C:
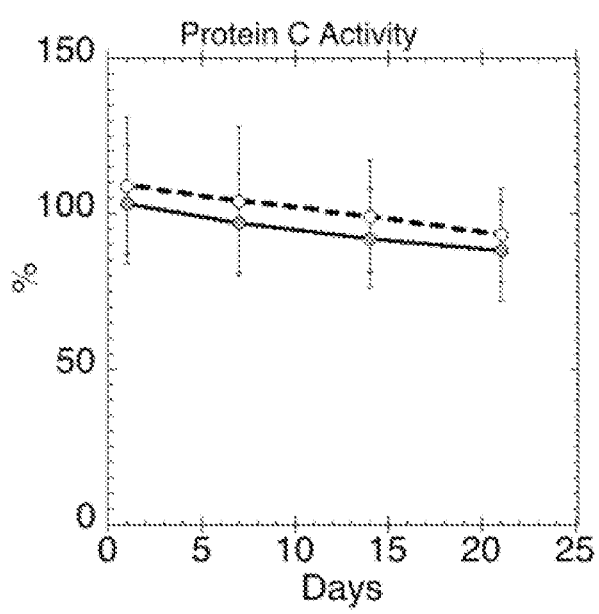
Figure 6D:
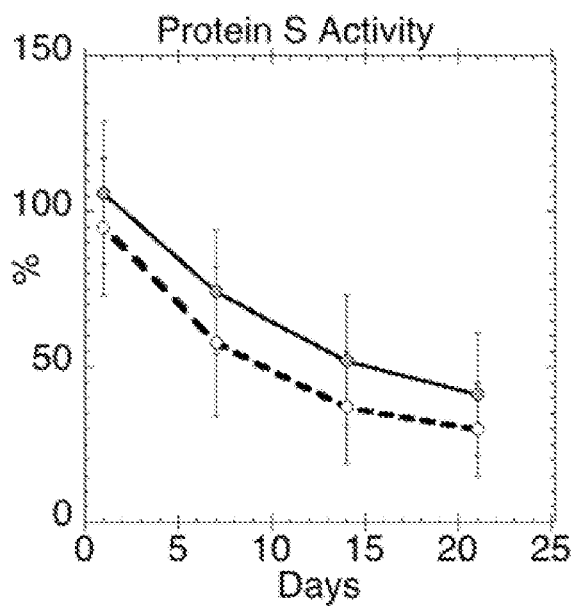
Figure 6E:
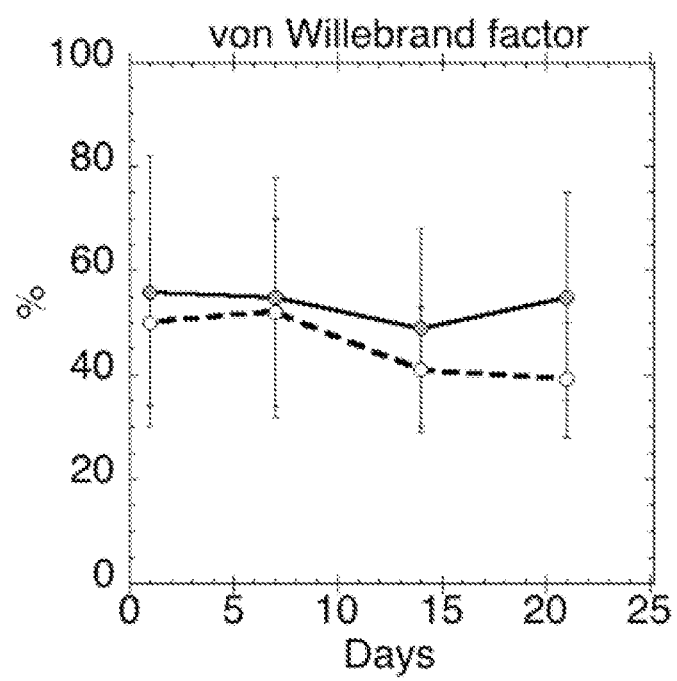
Figure 7A:
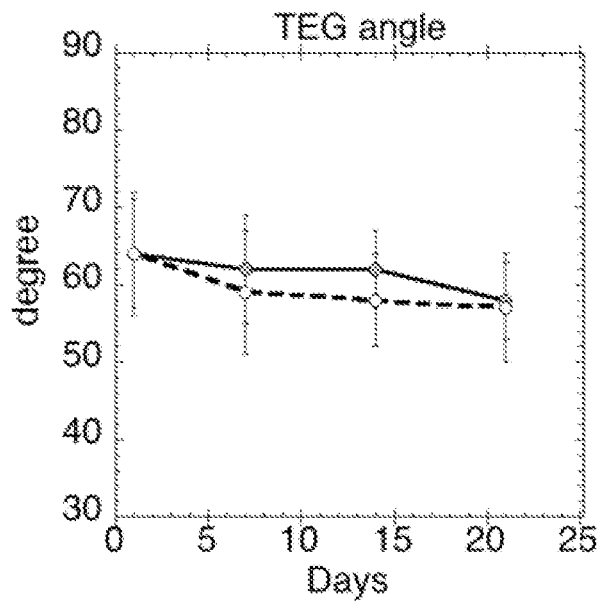
FIGS. 7A to 7D are graphs presenting the results of experiments according to the present disclosure comparing the storage of leukoreduced whole blood collected in anticoagulant solution CPDA1 (LRWB/CPDA1) under oxygen and carbon dioxide reduced (OCR) and conventionally stored LRWB/CPDA1 over a period of 21 days.
Figure 7B:
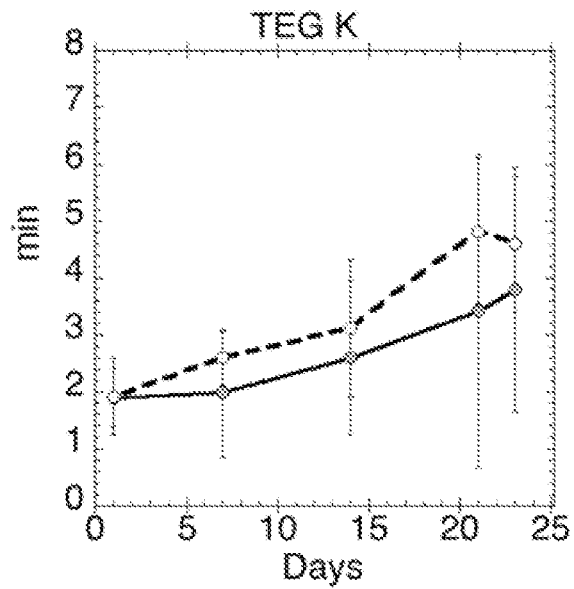
Figure 7C:
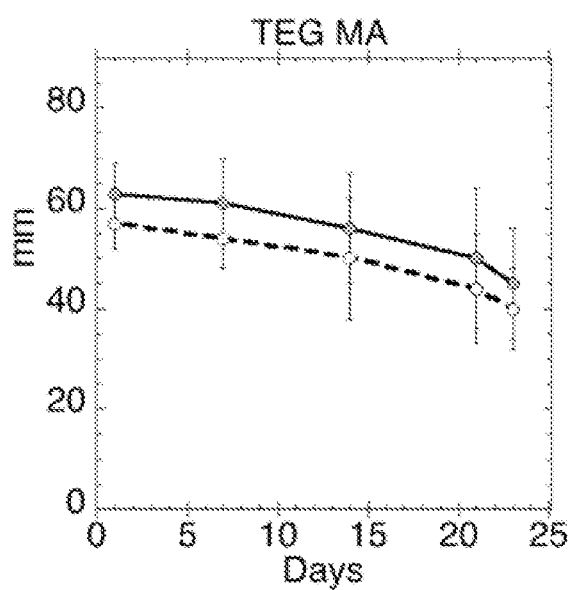
Figure 7D:
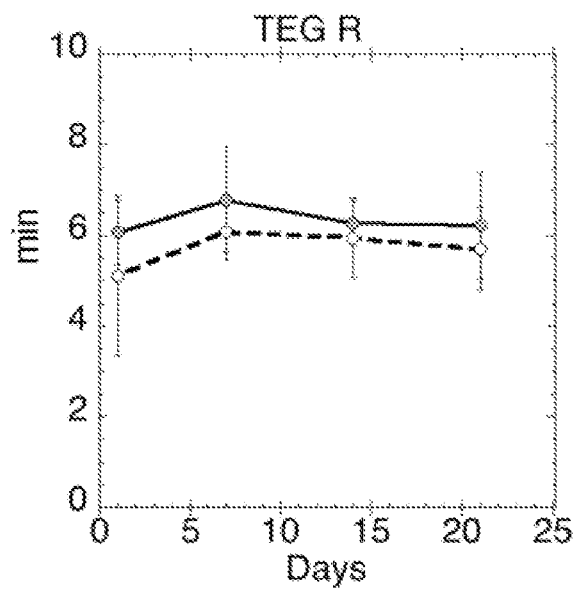

The units are evaluated for metabolic parameters including percent hemolysis (Plasma Low, Angelholm Sweden), ATP (DiaSys, Flacht, Germany), and 2,3-DPG (Sigma-Aldrich, St. Louis, Mo.) according to manufacturer's instructions. As shown in FIG. 4A, reduced levels of ATP are maintained in stored OCR-LRWB but increase in stored OR-LRWB compared to conventionally stored LRWB (solid line). As shown in FIG. 4B, increased levels of 2,3-DPG were maintained in stored OCR-LRWB and OR-LRWB compared to conventionally stored LRWB, for up to 21 days. Further, as shown in FIG. 4C, hemolysis is not significantly changed when comparing stored OR-LRWB and stored OCR-LRWB to conventionally stored LRWB (solid line).

The conventionally stored LRWB and OCR-LRWB are assessed for plasma coagulation parameters by evaluating Prothrombin Time (PT), activated Partial Prothrombin time (aPTT), and the levels of Fibrinogen and D-dimer. As shown in FIG. 5, the aPPT and PT were slightly, but not significantly prolonged in conventionally stored LRWB (solid line). Further, no evidence of coagulation activation was observed as evidence by similar fibrinogen and D-dimer levels.

The conventionally stored LRWB and OCR-LRWB are further assessed for plasma dotting factors by determining the activity levels for factors V, VIII, protein C activity, protein S activity and von Willebrand Factor (vWF). Protein C and protein S analysis are performed using the ACL TOP® (Instrumentation Laboratory) and the STA-R Evolution Coagulation Analyzer® (Diagnostica Stago, Inc.), respectively, according to the manufacturer's instructions. As shown in FIG. 6, the levels of Factor V, Factor VIII, Protein C activity, protein S activity, and vWF were not significantly changed in anaerobic, hypothermic stored OCR-LRWB (broken line) compared to conventionally stored WB (solid line).

The conventionally stored LRWB and OCR-LRWB are further assessed for coagulation using thromboelastography (TEG) with the Haemoscope Thromboelastograph® analyzer (Haemonetics) according to the manufacturer's instructions. As shown in FIGS. 7A to 7D, no significant difference was observed for propagation (TEG Angle), amplification (TEG K), maximum amplitude (TEG MA), or reaction time (TEG R) in OCR-LRWB (broken line) compared to conventionally stored LRWB (solid line).

While the present disclosure has been described with reference to particular embodiments, it will be understood by those skilled in the art that various changes may be made and equivalents may be substituted for elements thereof without departing from the scope of the present disclosure. In addition, many modifications may be made to adapt a particular situation or material to the teachings of the present disclosure without departing from the scope of the present disclosure.

Therefore, it is intended that the present disclosure not be limited to the particular embodiments disclosed as the best mode contemplated for carrying out the present disclosure, but that the present disclosure will include all embodiments falling within the scope and spirit of the appended claims.

The invention claimed is:

1. A method for improving survival of a patient in need of multiple transfusions comprising transfusing stored oxygen and carbon dioxide reduced leukoreduced whole blood with platelets (OCR-LRWB+PLT) comprising an anticoagulant to a patient in need of receiving multiple whole blood transfusions.

2. The method of claim 1, wherein said OCR-LRWB+PLT comprise reduced unbound levels of the factor RANTES compared to conventionally stored leukoreduced whole blood with platelets (LRWB+PLT).

3. The method of claim 2, wherein said level of RANTES is less than 500 pg/ml after 21 days of storage under deoxygenated conditions.

4. The method of claim 3, wherein said level of RANTES is less than 300 pg/ml after 21 days of storage under deoxygenated conditions.

5. The method of claim 1, wherein said OCR-LRWB+PLT comprise reduced levels of the factor eotaxin compared to conventionally stored leukoreduced whole blood with platelets (LRWB+PLT).

6. The method of claim 5, wherein said level of eotaxin is less than 150 pg/ml after 21 days of storage under deoxygenated conditions.

7. The method of claim 1, wherein said patient in need of multiple transfusions is a trauma patient, transplant patient, cardiac surgery patient, obstetrics patient, GI surgery patient, cancer patient, or orthopedic surgery patient.

8. The method of claim 7, wherein said trauma patient is a hemorrhagic trauma patient or blunt trauma patient.

9. A method of reducing an inflammatory response in a patient in need of a blood transfusion comprising transfusing oxygen and carbon dioxide reduced and leukoreduced whole blood with platelets (OCR-LRWB+PLT) to said patient in need thereof, wherein said OCR-LRWB+PLT has reduced levels of inflammatory cytokines after storage under anaerobic conditions compared to conventionally stored leukoreduced whole blood with platelets (LRWB+PLT).

10. The method of claim 9, wherein said reduced level of inflammatory cytokine is a reduced level of the cytokine eotaxin or RANTES, compared to conventionally stored leukoreduced whole blood with platelets (LRWB+PLT).

11. The method of claim 1, wherein said anticoagulant is CPD, CPDA1, ACD, or ACD-A.

* * * * *